United States Patent
Fretzen et al.

(10) Patent No.: US 8,748,573 B2
(45) Date of Patent: Jun. 10, 2014

(54) FORMULATIONS COMPRISING LINACLOTIDE

(75) Inventors: Angelika Fretzen, Somerville, MA (US); Steven Witowski, Melrose, MA (US); Alfredo Grossi, Somerville, MA (US); Hong Zhao, Somerville, MA (US); Mahendra Dedhiya, Pomona, NY (US); Yun Mo, Commack, NY (US)

(73) Assignee: Ironwood Pharmaceuticals, Inc., Cambridge, MA (US)

( * ) Notice: Subject to any disclaimer, the term of this patent is extended or adjusted under 35 U.S.C. 154(b) by 319 days.

(21) Appl. No.: 12/851,330

(22) Filed: Aug. 5, 2010

(65) Prior Publication Data

US 2011/0059903 A1  Mar. 10, 2011

Related U.S. Application Data

(60) Provisional application No. 61/231,725, filed on Aug. 6, 2009.

(51) Int. Cl.
*C07K 7/08* (2006.01)
*C07K 7/06* (2006.01)

(52) U.S. Cl.
USPC .......................................... 530/327; 530/328

(58) Field of Classification Search
None
See application file for complete search history.

(56) References Cited

U.S. PATENT DOCUMENTS

| | | | |
|---|---|---|---|
| 4,544,568 A * | 10/1985 | Heyland et al. | 426/650 |
| 4,992,419 A * | 2/1991 | Woog et al. | 514/7.7 |
| 5,221,495 A * | 6/1993 | Cao | 510/321 |
| 5,451,410 A | 9/1995 | Milstein et al. | |
| 5,593,696 A | 1/1997 | McNally et al. | |
| 5,654,278 A * | 8/1997 | Sørensen | 514/11.3 |
| 5,904,935 A | 5/1999 | Eckenhoff et al. | |
| 6,068,850 A | 5/2000 | Stevenson et al. | |
| 6,124,261 A | 9/2000 | Stevenson et al. | |
| 6,541,606 B2 | 4/2003 | Margolin et al. | |
| 6,734,162 B2 | 5/2004 | Van Antwerp et al. | |
| 6,828,303 B2 | 12/2004 | Kim et al. | |
| 6,979,437 B2 | 12/2005 | Bartus et al. | |
| 6,995,200 B2 * | 2/2006 | Krohnke | 524/128 |
| 7,056,942 B2 * | 6/2006 | Hildesheim et al. | 514/411 |
| 7,141,254 B2 * | 11/2006 | Bhaskaran et al. | 424/754 |
| 7,304,036 B2 | 12/2007 | Currie et al. | |
| 7,351,798 B2 | 4/2008 | Margolin et al. | |
| 7,371,727 B2 | 5/2008 | Currie et al. | |
| 7,494,979 B2 | 2/2009 | Currie et al. | |
| 7,704,947 B2 | 4/2010 | Currie et al. | |
| 7,745,409 B2 | 6/2010 | Currie et al. | |
| 7,767,644 B2 | 8/2010 | Schumann et al. | |
| 7,772,188 B2 | 8/2010 | Currie et al. | |
| 7,910,546 B2 | 3/2011 | Currie et al. | |
| 8,080,526 B2 | 12/2011 | Currie et al. | |
| 8,101,579 B2 | 1/2012 | Currie et al. | |
| 8,110,553 B2 | 2/2012 | Currie et al. | |
| 2003/0003563 A1 | 1/2003 | Vinkemeier et al. | |
| 2003/0069182 A1 | 4/2003 | Rinella | |
| 2003/0073628 A1 * | 4/2003 | Shailubhai et al. | 514/12 |
| 2003/0104996 A1 * | 6/2003 | Li et al. | 514/12 |
| 2003/0175230 A1 | 9/2003 | Dubief | |
| 2004/0265242 A1 | 12/2004 | Bartus et al. | |
| 2004/0266989 A1 | 12/2004 | Currie et al. | |
| 2005/0020811 A1 * | 1/2005 | Currie et al. | 530/327 |
| 2007/0122354 A1 | 5/2007 | Hastedt et al. | |
| 2007/0154406 A1 | 7/2007 | Moon et al. | |
| 2007/0202165 A1 | 8/2007 | Heuer et al. | |
| 2009/0110729 A1 * | 4/2009 | Giovannone et al. | 424/474 |
| 2009/0253634 A1 | 10/2009 | Currie et al. | |
| 2009/0305993 A1 | 12/2009 | Currie | |
| 2010/0048489 A1 * | 2/2010 | Fretzen et al. | 514/14 |
| 2010/0221329 A1 | 9/2010 | Shailubhai et al. | |
| 2012/0009225 A1 | 1/2012 | Fretzen et al. | |
| 2012/0039949 A1 | 2/2012 | Fretzen et al. | |
| 2012/0213846 A1 | 8/2012 | Fretzen et al. | |
| 2013/0190239 A1 | 7/2013 | Fretzen et al. | |
| 2013/0273169 A1 | 10/2013 | Fretzen et al. | |

FOREIGN PATENT DOCUMENTS

| | | |
|---|---|---|
| JP | 64-009938 | 1/1989 |
| JP | 2003-201256 | 7/2003 |
| WO | WO9012029 | 10/1990 |
| WO | WO9104743 | 4/1991 |
| WO | WO 97/03692 * | 2/1997 |
| WO | WO9704796 | 2/1997 |
| WO | WO9800152 | 1/1998 |
| WO | WO9800157 | 1/1998 |
| WO | WO0004880 | 2/2000 |
| WO | WO0032172 | 6/2000 |
| WO | WO0226248 | 4/2002 |
| WO | WO02078683 | 10/2002 |
| WO | WO03014304 | 2/2003 |

(Continued)

OTHER PUBLICATIONS

Vippagunta et al ('Crystalline solids' Adv Drug Delivery Rev. v48 2001 pp. 3-26).*
Lechuga-ballesteros et al ('Trileucine improves aerosol performance and stability of spray-dried powders for inhalation' Journal of Pharmaceutical Sciences v97(1) Jan. 2008 pp. 287-302).*
Reporter's guide to irritable bowel syndrome retrieved from http://www.aboutibs.org/pdfs/ReportersGuideIBS.pdf on Nov. 28, 2012 total of 18 pages where the main text is numbered as pp. 1-14.*
Cook et al 'Chronic constipation:overview and challenges' Neurogastroenterolgy and motility v21(supplement 2) 2009 pp. 1-8.*
Definition of lyophilization retrieved from http://medical.yourdictionary.com/lyophilization on May 1, 2013, 2 pages*
Ahmed, Hashim and Shah, Navnit., " Formulations of Low Dose Medicines—Theory and Practice." American Pharmaceutical Review, 3(3): 1-4, 2000.

(Continued)

*Primary Examiner* — Karlheinz R Skowronek
*Assistant Examiner* — Mindy Newman
(74) *Attorney, Agent, or Firm* — Honigman Miller Schwartz & Cohn; Kelly T. Murphy; Jonathan P. O'Brien

(57) ABSTRACT

The present invention relates to stable compositions comprising linaclotide, as well as to various methods and processes for the preparation and use of the compositions.

10 Claims, No Drawings

(56) References Cited

FOREIGN PATENT DOCUMENTS

| | | |
|---|---|---|
| WO | WO02062369 A3 | 8/2003 |
| WO | WO2004052343 | 6/2004 |
| WO | WO2005014025 | 2/2005 |
| WO | WO2005042029 | 5/2005 |
| WO | WO2005087797 | 9/2005 |
| WO | WO2007044375 | 4/2007 |
| WO | WO2008006125 | 1/2008 |
| WO | WO2008021133 | 2/2008 |
| WO | WO2008027854 | 3/2008 |
| WO | WO2008106429 | 9/2008 |
| WO | WO2008151257 | 12/2008 |
| WO | WO2010065751 | 6/2010 |
| WO | WO2011019819 | 2/2011 |

OTHER PUBLICATIONS

Andresen et al., "Effect of 5 Days Linaclotide on Transit and Bowel Function in Females With Constipation-Predominant Irritable Bowel Syndrome." Gastroenterology, 133 (3): 761-768, 2007.

Andresen et al., "Linaclotide Acetate." Drugs of the Future, 33(7): 570-576, 2008.

Aventis Pharmaceuticals, Inc. (2002). DDAVP (desmopressin acetate) tablet, [Product Label]. Bridgewater, NJ 08807, USA.

Bedu-Addo, F. et al., "Preformulation Development of Recombinant Pegylated Staphylokinase SY161 Using Statistical Design." AAPS PharmSci (http://www.aapspharmsci.org), 4(4) article 19, Jan. 11, 2002.

Bedu-Addo, F.K. et al., "Use of Biophysical Characterization in Preformulation Development of a Heavy-Chain Fragment of Botulinum Serotype B: Evalulation of Suitable Purification Process Conditions." Pharmceutical Research, 21(8): 1353-1361, 2004.

Camilleri et al., "Challenges to the Therapeutic Pipeline for Irritable Bowel Syndrome: End Points and Regulatory Hurdles." Gastroenterology, 135(6): 1877-1891, 2008.

Capasso et al., "Deamidation via Cyclic Imide of Asparaginyl Peptides: Dependence on Salts, Buffers and Organic Solvents." Peptide Research, 4(4): 234-238, 1991.

Carpenter et al., "Rational Design of Stable Lyophilized Protein Formulations: Some Practical Advice." Pharmaceutical Research, 14(8): 969-975, 1997.

Chourasia, M.K. and Jain, S.K., "Pharmaceutical approaches to colon targeted drug delivery systems." J Pharm Pharmaceut Sci (www.ualberta.ca/-csps), 6(1): 33-66, 2003.

Cleland et al., "The Development of Stable Protein Formulations: A Close Look at Protein Aggregation, Deamidation, and Oxidation." Critical Reviews in Therapeutic Drug Carrier Systems, 10(4): 307-377, 1993.

Elan Pharmaceuticals, Inc. (2004). PRIALT (ziconotide) injection, solution, [Product Label]. San Diego, CA 92121, USA.

Fix, J.A., "Oral Controlled Release Technology for Peptides: Status and Future Prospects." Pharmaceutical Research, 13(12): 1760-1764, 1996.

Fu et al., "Protein Stability in Controlled-Release Systems." Nature Biotechnology, 18: 24-25, 2000.

"International Nonproprietary Names for Pharmaceutical Substances (INN)." WHO Drug Information, 21(3): 247-264, 2007.

Kirby, "Oil-Based Formulations for Oral Delivery of Therapeutic Peptides." Journal of Liposome Research, 10(4): 391-407, 2000.

Mehta, N.M., "Oral Delivery and Recombinant Production of Peptide Hormones. Part I: Making Oral Delivery Possible: Enteric-coated capsules or tablets with additional excipients enable intestinal delivery." Bio-Pharm International (www.biopharm-mag.com), Jun. 1-6, 2004.

Mehta, N.M., "Oral Delivery and Recombinant Production of Peptide Hormones. Part II: Recombinant Production of Therapeutic Peptides." Bio-Pharm International (www.biopharm-mag.com), Jun. 7-9, 2004.

Microbia, Forest. "iviicrobia and Forest Laboratories Announce Preliminary Results of Linaclotide Phase 2B Studies." Communications of Microbia: pages 1-4, 2008.

Oliyai et al., "Chemical Pathways of Peptide Degradation. VII. Solid State Chemical Instability of an Aspartyl Residue in a Model Hexapeptide." Pharmaceutical Research, 11(6): 901-908, 1994.

Oliyai et al., "Solid State Chemical Instability of an Asparaginyl Residue in a Model Hexapeptide." Journal of Pharmaceutical Science & Technology, 48(3): 167-173, 1994.

Patel, K. and Borchardt, R.T., "Chemical Pathways of Peptide Degradation. III. Effect of Primary Sequence on the Pathways of Deamidation of Asparaginyl Residues in Hexapeptides." Pharmaceutical Research, 7(8): 787-793, 1990.

Patel, K. and Borchardt, R.T., "Deamidation of Asparaginyl Residues in Proteins: A Potential Pathway for Chemical Degradation of Proteins in Lyophilized Dosage Forms." Journal of Parenteral Science & Technology, 44(6): 300-301, 1990.

Sejourne, F. et al., "Development of a Novel Bioactive Formulation of Vasoactive Intestinal Peptide in Sterically Stabilized Liposomes." Pharmaceutical Research, 14(3): 362-365, 1997.

Constantino, H.R, et al., "Moisture-Induced Aggregation of Lyophilized Insulin". Pharmaceutical Research, 11(1): 21-29, 1994.

Dulbecco et al., "Plaque formation and isolation of pure liner with poliomyelitis viruses." Journal of Experimental Medicine, 99(2): 167-182, 1954.

Grenha et al., "Chitosan nanoparticles are compatible with respiratory epithelial cells in vitro." European Journal of Pharmaceutical Sciences, 31: 73-84, 2007.

Shailubhai et al., "Uroguanylin treatment suppresses polyp formation in the Apc(Min/+) mouse and induces apoptosis in human colon adenocarcinoma cells via cyclic GMP." Cancer Res., 60:5151-5157, 2000.

Langer, R. "Drug delivery and targeting", Nature; 392 (Supp): 5-10, 1998.

* cited by examiner

US 8,748,573 B2

FORMULATIONS COMPRISING LINACLOTIDE

CLAIM OF PRIORITY

This application claims priority under 35 USC §119(e) to U.S. Provisional Patent Application Ser. No. 61/231,725, filed on Aug. 6, 2009, the entire contents of which is hereby incorporated by reference.

SEQUENCE LISTING

This application incorporates by reference in its entirety the Sequence Listing entitled "IW080US1_ST25.txt" (2.20 kilobytes), which was created Feb. 19, 2013 and filed electronically herewith.

FIELD OF THE INVENTION

The present invention relates to stable formulations comprising linaclotide, processes for making the compositions and methods of treating conditions using the compositions.

BACKGROUND OF THE INVENTION

U.S. Pat. Nos. 7,304,036 and 7,371,727 disclose peptides that act as agonists of the guanylate cyclase C (GC-C) receptor for the treatment of gastrointestinal disorders. One particular peptide disclosed is linaclotide, which consists of the following amino acid sequence: Cys Cys Glu Tyr Cys Cys Asn Pro Ala Cys Thr Gly Cys Tyr (SEQ ID NO: 1). The '036 and '727 patents also disclose methods for preparing linaclotide and related peptides. The contents of these patents are incorporated herein by reference in their entirety.

There remains a need for improved formulations of linaclotide, and pharmaceutically acceptable salts thereof, having improved stability and performance properties.

The present invention seeks to provide such improved formulations of linaclotide, as well as processes for making the formulations and methods of treating gastrointestinal disorders by administering the formulations.

SUMMARY OF THE INVENTION

In some embodiments, a stable pharmaceutical composition comprising linaclotide and a pharmaceutically acceptable carrier is provided.

In some embodiments, a pharmaceutical composition of linaclotide is provided, wherein the composition comprises a stabilizing amount of a polymer, a stabilizing amount of a sterically hindered primary amine, a stabilizing amount of a cation, or a combination or mixture thereof.

In some embodiments, an immediate release pharmaceutical composition comprising linaclotide, or a pharmaceutically acceptable salt thereof is provided.

In some embodiments, a method of treating a gastrointestinal disorder comprising administering to a patient in need thereof, a therapeutically effective amount of the compositions is provided.

DETAILED DESCRIPTION OF THE INVENTION

Stable formulations of linaclotide are provided herein. In addition, methods of using the formulations to treat gastrointestinal disorders, including irritable bowel syndrome ("IBS") (for example, constipation-predominant IBS) and/or constipation (for example, chronic constipation), and processes for making the compositions are provided.

It has been found, in some embodiments, that the stability of linaclotide compositions can be increased or improved by including in the compositions a suitable amount of a polymer component, a sterically hindered primary amine (e.g., amino acid) component, and/or a cation (e.g., metal cation) component. These components increase or enhance the stability of a linaclotide composition, for example, by preventing, lessening, and/or decreasing degradation of linaclotide within the composition (for example, due to moisture-driven degradation reactions, e.g., hydrolysis, deamidation, and/or multimerization reactions). For instance, it has been found in some embodiments that addition or inclusion of a suitable amount of a cation (e.g., $Mg^{2+}$, $Ca^{2+}$, $Zn^{2+}$) in the composition increases the stability of the composition against oxidative degradation of linaclotide. Moreover, it has been found in some embodiments that inclusion of a suitable amount of a sterically hindered primary amine (e.g., leucine) in the composition increases the stability of the composition against the formation of formaldehyde imine adducts of linaclotide. Moreover, it has been found in some embodiments that inclusion of both a sterically hindered primary amine (e.g., leucine) and a cation (e.g., $Ca^{2+}$) in suitable amounts in the composition increases the stability of the composition against the formation of hydrolysis products of linaclotide.

In addition, it has been found in some embodiments that inclusion of a suitable amount of a polymer (e.g., polyvinyl pyrrolidone or polyvinyl alcohol) in the composition increases the stability of the composition for example by decreasing the mobility and/or reactivity of linaclotide within the composition, e.g., by forming a complex or matrix (for example, a glassy and/or rigid matrix) with linaclotide (e.g., by vitrification reaction), by preventing or lessening hydrogen bond formation between linaclotide and water molecules, and/or by enhancing the three-dimensional structural integrity of linaclotide. In this regard, it has been found in some embodiments that combining linaclotide with specific amounts or ratios of polymer, sterically hindered primary amine and cation causes a synergistic enhancement or improvement in the stability of linaclotide within pharmaceutical compositions, for example as compared to pharmaceutical compositions not containing the polymer, sterically hindered primary amine and cation and/or the same concentrations of these components.

Suitable polymers for inclusion in the composition are, for example, polyvinyl pyrrolidone (PVP), polyvinyl alcohol (PVA), hydroxylpropyl methyl cellulose (HPMC), hydroxylpropyl cellulose (HPC), methyl cellulose, methacrylate polymers, cyclodextrin, dextran, polyacrylic acid, chitosan, guar gum, xanthan gum, polyethylene polypropylene oxide, poly(sodium vinylsulfonate), polyethylene glycol, poly(arginine), poly carbophil, polyvinyl pyrrolidone-co-vinyl acetate, a poloxamer (e.g., Pluronic® products available from BASF), or a combination or mixture thereof. In some embodiments, the composition comprises a polymer selected from PVP, PVA, methacrylate polymers, cyclodextrin, dextran, polyacrylic acid, chitosan, guar gum, xanthan gum, polyethylene polypropylene oxide, polyethylene glycol, poly(arginine), poly carbophil, polyvinyl pyrrolidone-co-vinyl acetate, a poloxamer, or a combination or mixture thereof. In some embodiments, the composition comprises PVP, PVA, or a mixture thereof. In some embodiments, the composition comprises PVP. In some embodiments, the composition comprises PVA. In some embodiments, the composition comprises methacrylate polymers, cyclodextrin, dextran, polyacrylic acid, chitosan, xanthan gum, polyethylene polypropylene oxide, poly (sodium vinylsulfonate), polyethylene glycol, poly(arginine), poly carbophil, polyvinyl pyrrolidone-co-vinyl acetate, a poloxamer (e.g., Pluronic® products available from BASF), or a combination or mixture thereof.

The composition can contain any stabilizing amount of a polymer. In some embodiments, the composition comprises between 0.01 and 10 wt. % of a polymer. In some embodiments, the composition comprises between 2.5 and 10 wt. % of a polymer. In some embodiments, the composition comprises between 0.01 and 5 wt. % of a polymer. In some embodiments, the composition comprises between 0.01 and 4 wt. % of a polymer. In some embodiments, the composition comprises between 0.1 and 3 wt. % of a polymer. In some embodiments, the composition comprises between 0.01 and 2.5 wt. % of a polymer. In some embodiments, the composition comprises between 0.1 and 2.5 wt. % of a polymer. In some embodiments, the composition comprises between 0.5 and 2.5 wt. % of a polymer. In some embodiments, the composition comprises between 1 and 2.5 wt. % of a polymer. In some embodiments, the composition comprises between 0.01 and 2 wt. % of a polymer. In some embodiments, the composition comprises between 0.1 and 2 wt. % of a polymer. In some embodiments, the composition comprises between 0.5 and 2 wt. % of a polymer. In some embodiments, the composition comprises between 1 and 2 wt. % of a polymer.

In some embodiments, the composition comprises between 0.01 and 1.5 wt. % of a polymer. In some embodiments, the composition comprises between 0.1 and 1.5 wt. % of a polymer. In some embodiments, the composition comprises between 0.5 and 1.5 wt. % of a polymer. In some embodiments, the composition comprises between 0.1 and 1.25 wt. % of a polymer. In some embodiments, the composition comprises between 0.01 and 1 wt. % of a polymer. In some embodiments, the composition comprises between 0.1 and 1 wt. % of a polymer. In some embodiments, the composition comprises between 0.5 and 1 wt. % of a polymer. In some embodiments, the composition comprises between 0.01 and 0.5 wt. % of a polymer.

Suitable sterically hindered primary amines for inclusion in the composition are, for example, naturally-occurring amino acids (e.g., alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine), synthetic amino acids (e.g., lanthionine, theanine or 1-amino cyclohexane), amino sugars (e.g., chitosan or glucosamine), or combination or mixtures thereof. In some embodiments, the composition comprises an amino acid selected from alanine, arginine, asparagine, aspartic acid, cysteine, glutamic acid, glutamine, histidine, isoleucine, leucine, lysine, methionine, phenylalanine, proline, serine, threonine, tryptophan, tyrosine, valine, or a mixture thereof. In some embodiments, the composition comprises an amino acid selected from leucine, isoleucine, asparagine, glutamine, glutamic acid, histidine, cysteine, alanine, serine, threonine, tyrosine, proline, tryptophan, or a combination or mixture thereof. In some embodiments, the composition comprises an amino acid selected from leucine, isoleucine, methionine, alanine, or a combination or mixture thereof. In some embodiments, the composition comprises an amino acid selected from leucine, isoleucine, alanine, or a combination or mixture thereof. In some embodiments, the composition comprises an amino acid selected from leucine, isoleucine, methionine, or a combination or mixture thereof. In some embodiments, the composition comprises an amino acid selected from leucine, methionine, alanine, or a combination or mixture thereof. In some embodiments, the composition comprises leucine, methionine, or a mixture thereof. In some embodiments, the composition comprises leucine, isoleucine, or a mixture thereof. In some embodiments, the composition comprises leucine, alanine, or a mixture thereof. In some embodiments, the composition comprises leucine. In some embodiments, the composition comprises isoleucine. In some embodiments, the composition comprises methionine. In some embodiments, the composition comprises alanine. In some embodiments, the composition comprises an amino acid selected from arginine, cysteine, glycine, lysine, proline, serine, or a mixture thereof. In some embodiments, the composition comprises 1-amino cyclohexane.

The composition can comprise any stabilizing amount of a sterically hindered primary amine component. For example, the composition can comprise a molar ratio of sterically hindered primary amine (e.g., amino acid) to linaclotide between 100:1 and 1:100. In some embodiments, the composition comprises a molar ratio of sterically hindered primary amine to linaclotide between 100:1 and 1:1. In some embodiments, the composition comprises a molar ratio of sterically hindered primary amine to linaclotide between 90:1 and 2:1. In some embodiments, the composition comprises a molar ratio of sterically hindered primary amine to linaclotide between 80:1 and 5:1. In some embodiments, the composition comprises a molar ratio of sterically hindered primary amine to linaclotide between 70:1 and 10:1. In some embodiments, the composition comprises a molar ratio of sterically hindered primary amine to linaclotide between 60:1 and 20:1. In some embodiments, the composition comprises a molar ratio of sterically hindered primary amine to linaclotide between 50:1 and 30:1. In some embodiments, the composition comprises a molar ratio of sterically hindered primary amine to linaclotide between 40:1 and 20:1.

In some embodiments, the composition comprises a molar ratio of sterically hindered primary amine to linaclotide between 100:1 and 20:1. In some embodiments, the composition comprises a molar ratio of sterically hindered primary amine to linaclotide between 100:1 and 25:1. In some embodiments, the composition comprises a molar ratio of sterically hindered primary amine to linaclotide between 100:1 and 30:1. In some embodiments, the composition comprises a molar ratio of sterically hindered primary amine to linaclotide between 100:1 and 40:1. In some embodiments, the composition comprises a molar ratio of sterically hindered primary amine to linaclotide between 100:1 and 50:1. In some embodiments, the composition comprises a molar ratio of sterically hindered primary amine to linaclotide between 100:1 and 60:1. In some embodiments, the composition comprises a molar ratio of sterically hindered primary amine to linaclotide between 100:1 and 70:1.

In some embodiments, the composition comprises a molar ratio of sterically hindered primary amine to linaclotide of at least 5:1. In some embodiments, the composition comprises a molar ratio of sterically hindered primary amine to linaclotide of at least 10:1. In some embodiments, the composition comprises a molar ratio of sterically hindered primary amine to linaclotide of at least 20:1. In some embodiments, the composition comprises a molar ratio of sterically hindered primary amine to linaclotide of at least 25:1. In some embodiments, the composition comprises a molar ratio of sterically hindered primary amine to linaclotide of at least 30:1. In some embodiments, the composition comprises a molar ratio of sterically hindered primary amine to linaclotide of at least 40:1. In some embodiments, the composition comprises a molar ratio of sterically hindered primary amine to linaclotide between 5:1 and 1:1. In some embodiments, the composition comprises a molar ratio of sterically hindered primary amine to linaclotide between 1:100 and 1:1.

In some embodiments, the composition comprises about 0.5 to about 10% by weight of a sterically hindered primary amine relative to the total weight of the pharmaceutical composition (e.g., solid oral dosage form or bead). In some embodiments, the composition comprises about 0.5 to about 7% by weight of a sterically hindered primary amine. In some embodiments, the composition comprises about 0.5 to about 5% by weight of a sterically hindered primary amine. In some embodiments, the composition comprises about 0.5 to about 4% by weight of a sterically hindered primary amine. In some embodiments, the composition comprises about 0.5 to about 3% by weight of a sterically hindered primary amine. In some embodiments, the composition comprises about 0.5 to about 2% by weight of a sterically hindered primary amine. In some embodiments, the composition comprises about 0.75 to about 5% by weight of a sterically hindered primary amine. In some embodiments, the composition comprises about 0.75 to about 4% by weight of a sterically hindered primary amine. In some embodiments, the composition comprises about 0.75 to about 3% by weight of a sterically hindered primary amine. In some embodiments, the composition comprises about 0.75 to about 2% by weight of a sterically hindered primary amine. In some embodiments, the composition comprises about 1 to about 5% by weight of a sterically hindered primary amine. In some embodiments, the composition comprises about 1 to about 4% by weight of a sterically hindered primary amine. In some embodiments, the composition comprises about 1 to about 3% by weight of a sterically hindered primary amine. In some embodiments, the composition comprises about 1 to about 2% by weight of a sterically hindered primary amine.

Any suitable cation(s) can be included in the composition, for example, any suitable metal cation or organic cation. In some embodiments, the composition comprises a metal cation selected from calcium, potassium, magnesium, zinc, aluminum, iron, tin, manganese, chromium, cobalt, nickel, barium, sodium, or a combination or mixture thereof. In some embodiments, the composition comprises a metal cation selected from iron, tin, chromium, cobalt, nickel, barium, or a combination or mixture thereof. In some embodiments, the composition comprises a metal cation selected from calcium, potassium, magnesium, zinc, aluminum, manganese, chromium, cobalt, nickel, barium, sodium, or a combination or mixture thereof. In some embodiments, the composition comprises a metal cation selected from aluminum, calcium, potassium, sodium, magnesium, manganese, zinc, or a combination or mixture thereof. In some embodiments, the composition comprises a metal cation selected from calcium, magnesium, manganese, zinc, or a combination or mixture thereof. In some embodiments, the composition comprises a divalent metal cation. In some embodiments, the composition comprises a divalent metal cation selected from $Ca^{2+}$, $Mg^{2+}$, $Zn^{2+}$, $Mn^{2+}$, or a combination or mixture thereof. In some embodiments, the composition comprises $Mg^{2+}$. In some embodiments, the composition comprises $Ca^{2+}$. In some embodiments, the composition comprises $Zn^{2+}$. In some embodiments, the composition comprises aluminum. Moreover, the metal cation can be added to the composition in any suitable form, for example any pharmaceutically acceptable salt with any appropriate counterion. Suitable metal salts include, for example, calcium chloride, calcium carbonate, calcium acetate, magnesium chloride, magnesium acetate, zinc acetate, zinc chloride, or mixtures thereof. In some embodiments, the composition comprises calcium chloride, magnesium chloride, zinc acetate, or any combination or mixture thereof. In some embodiments, the composition comprises calcium chloride. In some embodiments, the composition comprises magnesium chloride. In some embodiments, the composition comprises zinc acetate.

Suitable organic cations include, for example, ammonium hydroxide, D-arginine, L-arginine, t-butylamine, calcium acetate hydrate, calcium carbonate, calcium DL-malate, calcium hydroxide, choline, ethanolamine, ethylenediamine, glycine, L-histidine, L-lysine, magnesium hydroxide, N-methyl-D-glucamine, L-ornithine hydrochloride, potassium hydroxide, procaine hydrochloride, L-proline, pyridoxine, L-serine, sodium hydroxide, DL-tryptophan, tromethamine, L-tyrosine, L-valine, carnitine, taurine, creatine malate, arginine alpha keto glutarate, ornithine alpha keto glutarate, spermine acetate, spermidine chloride, or combinations or mixtures thereof. In some embodiments, the organic cation is selected from the group consisting of N-methyl D-glucamine, choline, arginine, lysine, procaine, tromethamine (TRIS), spermine, N-methyl-morpholine, glucosamine, N,N-bis 2-hydroxyethyl glycine, diazabicycloundecene, creatine, arginine ethyl ester, amantadine, rimantadine, ornithine, taurine, citrulline, or a combination or mixture thereof.

The composition can comprise any stabilizing amount of a cation. For example, the composition can comprise a molar ratio of cation to linaclotide between 100:1 and 1:100. In some embodiments, the composition comprises a molar ratio of cation to linaclotide between 100:1 and 1:1. In some embodiments, the composition comprises a molar ratio of cation to linaclotide between 90:1 and 2:1. In some embodiments, the composition comprises a molar ratio of cation to linaclotide between 80:1 and 5:1. In some embodiments, the composition comprises a molar ratio of cation to linaclotide between 70:1 and 10:1. In some embodiments, the composition comprises a molar ratio of cation to linaclotide between 60:1 and 20:1. In some embodiments, the composition comprises a molar ratio of cation to linaclotide between 50:1 and 30:1. In some embodiments, the composition comprises a molar ratio of cation to linaclotide between 40:1 and 20:1. In some embodiments, the composition comprises a molar ratio of cation to linaclotide between 100:1 and 20:1. In some embodiments, the composition comprises a molar ratio of cation to linaclotide between 100:1 and 25:1. In some embodiments, the composition comprises a molar ratio of cation to linaclotide between 100:1 and 30:1. In some embodiments, the composition comprises a molar ratio of cation to linaclotide between 100:1 and 40:1. In some embodiments, the composition comprises a molar ratio of cation to linaclotide between 100:1 and 50:1. In some embodiments, the composition comprises a molar ratio of cation to linaclotide between 100:1 and 60:1. In some embodiments, the composition comprises a molar ratio of cation to linaclotide between 100:1 and 70:1.

In some embodiments, the composition comprises a molar ratio of cation to linaclotide of at least 5:1. In some embodiments, the composition comprises a molar ratio of cation to linaclotide of at least 10:1. In some embodiments, the composition comprises a molar ratio of cation to linaclotide of at least 20:1. In some embodiments, the composition comprises a molar ratio of cation to linaclotide of at least 25:1. In some embodiments, the composition comprises a molar ratio of cation to linaclotide of at least 30:1. In some embodiments, the composition comprises a molar ratio of cation to linaclotide of at least 40:1. In some embodiments, the composition comprises a molar ratio of cation to linaclotide of at least 60:1. In some embodiments, the composition comprises a molar ratio of cation to linaclotide between 5:1 and 1:1. In some embodiments, the composition comprises a molar ratio of cation to linaclotide between 1:100 and 1:1.

In some embodiments, the composition comprises about 0.5 to about 5% by weight of the cation or salt thereof. In some embodiments, the composition comprises about 0.5 to about 4% by weight of the cation or salt thereof. In some embodiments, the composition comprises about 0.5 to about 2% by weight of the cation or salt thereof. In some embodiments, the composition comprises about 0.5 to about 1.5% by weight of the cation or salt thereof. In some embodiments, the composition comprises about 0.5 to about 1.25% by weight of the cation or salt thereof. In some embodiments, the composition comprises about 0.5 to about 1% by weight of the cation or salt thereof. In some embodiments, the composition comprises about 0.6 to about 1.5% by weight of the cation or salt thereof. In some embodiments, the composition comprises about 0.6 to about 1.25% by weight of the cation or salt thereof. In some embodiments, the composition comprises about 0.6 to about 1% by weight of the cation or salt thereof.

In some embodiments, the composition comprises two or more stabilizing agents. For example, the composition can include a stabilizing amount of a polymer and a stabilizing amount of a sterically hindered primary amine. Moreover, the composition can include a stabilizing amount of a polymer and a stabilizing amount of a cation (e.g., metal cation). In addition, the composition can include a stabilizing amount of a sterically hindered primary amine and a stabilizing amount of a cation (e.g., metal cation). In some embodiments, the composition comprises a stabilizing amount of a polymer, a stabilizing amount of a sterically hindered primary amine, and a stabilizing amount of a cation.

In some embodiments, the composition comprises a stabilizing amount (e.g., about 0.1-2.5 wt. %) of PVP and a stabilizing amount (e.g., a molar ratio of amino acid to linaclotide between 100:1 and 30:1 or between 60:1 and 30:1) of an amino acid selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, or a mixture thereof. In some embodiments, the composition comprises a stabilizing amount of PVP and a stabilizing amount of an amino acid selected from alanine, arginine, asparagine, aspartic acid, cysteine, glutamic acid, glutamine, histidine, isoleucine, leucine, lysine, methionine, phenylalanine, proline, serine, threonine, tryptophan, tyrosine, valine, or a mixture thereof. In some embodiments, the composition comprises a stabilizing amount of PVP and a stabilizing amount of leucine, isoleucine, methionine, alanine, or a combination or mixture thereof. In some embodiments, the composition comprises a stabilizing amount of PVP and a stabilizing amount of leucine. In some embodiments, the composition comprises a stabilizing amount of PVP and a stabilizing amount of arginine, cysteine, glycine, lysine, proline, serine, or a mixture thereof.

In some embodiments, the composition comprises a stabilizing amount (e.g., about 0.1-2.5 wt. %) of PVA and a stabilizing amount (e.g., a molar ratio of amino acid to linaclotide between 100:1 and 30:1 or between 60:1 and 30:1) of an amino acid selected from alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, or a mixture thereof. In some embodiments, the composition comprises a stabilizing amount of PVA and a stabilizing amount of an amino acid selected from alanine, arginine, asparagine, aspartic acid, cysteine, glutamic acid, glutamine, histidine, isoleucine, leucine, lysine, methionine, phenylalanine, proline, serine, threonine, tryptophan, tyrosine, valine, or a mixture thereof. In some embodiments, the composition comprises a stabilizing amount of PVA and a stabilizing amount of leucine, isoleucine, methionine, alanine, or a combination or mixture thereof. In some embodiments, the composition comprises a stabilizing amount of PVA and a stabilizing amount of leucine. In some embodiments, the composition comprises a stabilizing amount of PVA and a stabilizing amount of arginine, cysteine, glycine, lysine, proline, serine, or a mixture thereof.

In some embodiments, the composition comprises a stabilizing amount (e.g., about 0.1-2.5 wt. %) of PVP and a stabilizing amount (e.g., a molar ratio of cation to linaclotide between 100:1 and 30:1 or between 100:1 and 60:1) of a cation (e.g., metal cation). In some embodiments, the composition comprises a stabilizing amount of PVP and a stabilizing amount of a divalent metal cation. In some embodiments, the composition comprises a stabilizing amount of PVP and a stabilizing amount of $Mg^{2+}$, $Ca^{2+}$, $Zn^{2+}$ or a salt thereof or a combination or mixture thereof. In some embodiments, the composition comprises a stabilizing amount of PVP and a stabilizing amount of $Ca^{2+}$ or a salt thereof. In some embodiments, the composition comprises a stabilizing amount of PVP and a stabilizing amount of $Mg^{2+}$ or a salt thereof. In some embodiments, the composition comprises a stabilizing amount of PVP and a stabilizing amount of $Zn^{2+}$ or a salt thereof.

In some embodiments, the composition comprises a stabilizing amount (e.g., about 0.1-0.5 wt. %) of PVP and a stabilizing amount (e.g., a molar ratio of cation to linaclotide between 100:1 and 30:1 or between 100:1 and 60:1) of a cation (e.g., metal cation).

In some embodiments, the composition comprises a stabilizing amount (e.g., about 0.1-2.5 wt. %) of PVA and a stabilizing amount (e.g., a molar ratio of cation to linaclotide between 100:1 and 30:1 or between 100:1 and 60:1) of a cation (e.g., metal cation). In some embodiments, the composition comprises a stabilizing amount of PVA and a stabilizing amount of a divalent metal cation. In some embodiments, the composition comprises a stabilizing amount of PVA and a stabilizing amount of $Mg^{2+}$, $Ca^{2+}$, $Zn^{2+}$ or a salt thereof or a combination or mixture thereof. In some embodiments, the composition comprises a stabilizing amount of PVA and a stabilizing amount of $Ca^{2+}$ or a salt thereof. In some embodiments, the composition comprises a stabilizing amount of PVA and a stabilizing amount of $Mg^{2+}$ or a salt thereof. In some embodiments, the composition comprises a stabilizing amount of PVA and a stabilizing amount of $Zn^{2+}$ or a salt thereof.

In some embodiments, the composition comprises a stabilizing amount (e.g., about 0.1-0.5 wt. %) of PVA and a stabilizing amount (e.g., a molar ratio of cation to linaclotide between 100:1 and 30:1 or between 100:1 and 60:1) of a cation (e.g., metal cation).

In some embodiments, the composition comprises a stabilizing amount (e.g., a molar ratio of amino acid to linaclotide between 100:1 and 30:1, between 60:1 and 30:1, or even between 50:1 and 30:1) of an amino acid selected from leucine, isoleucine, methionine, alanine; and a stabilizing amount (e.g., a molar ratio of cation to linaclotide between 100:1 and 30:1 or between 100:1 and 60:1) of a divalent metal cation selected from $Mg^{2+}$, $Ca^{2+}$, $Zn^{2+}$ or a salt thereof or a combination or mixture thereof. In some embodiments, the composition comprises a stabilizing amount of an amino acid selected from leucine, isoleucine; and a stabilizing amount of a divalent metal cation selected from $Mg^{2+}$, $Ca^{2+}$ or a salt thereof or a combination or mixture thereof. In some embodiments, the composition comprises a stabilizing amount of an amino acid selected from leucine or methionine; and a stabilizing amount of a divalent metal cation selected from $Ca^{2+}$, $Zn^{2+}$ or a salt thereof or a combination or mixture thereof.

In some embodiments, the composition comprises a stabilizing amount of leucine and a stabilizing amount of $Ca^{2+}$ or a salt thereof. In some embodiments, the composition comprises a stabilizing amount of a cation and a stabilizing amount of a sterically hindered primary amine. In some embodiments, the composition comprises a cation and a sterically hindered primary amine in a molar ratio of cation: sterically hindered primary amine (e.g., $Ca^{2+}$:leucine) of at least 1.5:1, e.g., at least 2:1, at least 2.5:1, at least 3:1, at least 4:1, or even at least 5:1 (for example, a molar ratio between 1.5:1 and 5:1, e.g., between 2:1 and 4:1, and between 1.5:1 and 2:1).

In some embodiments, the composition comprises (i) a stabilizing amount of PVP or PVA, (ii) a stabilizing amount of leucine, isoleucine, methionine, alanine, and (iii) a stabilizing amount of $Mg^{2+}$, $Ca^{2+}$, $Zn^{2+}$ or a salt thereof or a combination or mixture thereof. In some embodiments, the composition comprises a stabilizing amount of PVP, a stabilizing amount of leucine, and a stabilizing amount of a metal cation. In some embodiments, the composition comprises a stabilizing amount of PVP, a stabilizing amount of leucine, and a stabilizing amount of $Ca^{2+}$ or a salt thereof.

In some embodiments, the composition comprises a stabilizing amount of PVP, a stabilizing amount of leucine, and a stabilizing amount of $Mg^{2+}$ or a salt thereof. In some embodiments, the composition comprises a stabilizing amount of PVP, a stabilizing amount of leucine, and a stabilizing amount of $Zn^{2+}$ or a salt thereof. In some embodiments, the composition comprises a stabilizing amount of PVA, a stabilizing amount of leucine, and a stabilizing amount of $Ca^{2+}$ or a salt thereof. In some embodiments, the composition comprises a stabilizing amount of PVA, a stabilizing amount of leucine, and a stabilizing amount of $Mg^{2+}$ or a salt thereof. In some embodiments, the composition comprises a stabilizing amount of PVA, a stabilizing amount of leucine, and a stabilizing amount of $Zn^{2+}$ or a salt thereof.

In some embodiments, the composition comprises (i) between 0.01 and 5 wt. % of a polymer, (ii) a sterically hindered primary amine (e.g., an amino acid) in a molar ratio of primary amine to linaclotide between 100:1 and 10:1, and (iii) a cation (e.g., a metal cation) in a molar ratio of cation to linaclotide between 100:1 and 40:1. In some embodiments, the composition comprises (i) between 0.1 and 3 wt. % of a polymer, (ii) a sterically hindered primary amine (e.g., an amino acid) in a molar ratio of primary amine to linaclotide 100:1 and 30:1 (e.g., between 60:1 and 30:1 or even between 50:1 and 30:1), and (iii) a cation (e.g., a metal cation) in a molar ratio of cation to linaclotide between 100:1 and 60:1.

In some embodiments, the composition comprises (i) between 0.01 and 5 wt. % of a polymer selected from PVP and PVA, (ii) an amino acid selected from leucine, isoleucine, alanine, and methionine in a molar ratio of amino acid to linaclotide between 100:1 and 10:1, and (iii) a metal cation selected from $Ca^{2+}$, $Mg^{2+}$, and $Zn^{2+}$ in a molar ratio of cation to linaclotide between 100:1 and 40:1.

In some embodiments, the composition comprises (i) between 0.1 and 3 wt. % of a polymer selected from PVP and PVA, (ii) an amino acid selected from leucine, isoleucine, alanine, and methionine in a molar ratio of amino acid to linaclotide 100:1 and 30:1 (e.g., between 60:1 and 30:1), and (iii) a metal cation selected from $Ca^{2+}$, $Mg^{2+}$, and $Zn^{2+}$ in a molar ratio of cation to linaclotide between 100:1 and 60:1. In some embodiments, the composition comprises (i) between 0.01 and 5 wt. % (e.g., between 0.1 and 3 wt. % or even between 0.1 and 2.5 wt. %) of PVP or PVA, (ii) leucine in a molar ratio of leucine to linaclotide between 100:1 and 30:1 (e.g., between 60:1 and 30:1 or even between 50:1 and 30:1), and (iii) $Ca^{2+}$ in a molar ratio of $Ca^{2+}$ to linaclotide between 100:1 and 60:1.

In some embodiments, the composition comprises (i) between 0.01 and 5 wt. % (e.g., between 0.1 and 3 wt. % or even between 0.1 and 2.5 wt. %) of PVP, PVA or HPMC, (ii) leucine in a molar ratio of leucine to linaclotide between 60:1 and 10:1 (e.g., between 50:1 and 10:1 or even between 40:1 and 20:1), and (iii) $Ca^{2+}$ (or salt thereof) in a molar ratio of $Ca^{2+}$ (or salt thereof) to linaclotide between 100:1 and 40:1 (e.g., between 80:1 and 40:1 or between 70:1 and 50:1). In some embodiments, the composition comprises (i) between 0.01 and 5 wt. % (e.g., between 0.1 and 3 wt. % or even between 0.1 and 2.5 wt. %) of HPMC, (ii) leucine in a molar ratio of leucine to linaclotide between 60:1 and 10:1 (e.g., between 50:1 and 10:1 or even between 40:1 and 20:1), and (iii) $Ca^{2+}$ (or salt thereof) in a molar ratio of $Ca^{2+}$ (or salt thereof) to linaclotide between 100:1 and 40:1 (e.g., between 80:1 and 40:1 or between 70:1 and 50:1).

In some embodiments, the composition comprises (i) between 0.01 and 0.5 wt. % of a polymer, (ii) a sterically hindered primary amine (e.g., an amino acid) in a molar ratio of primary amine to linaclotide between 100:1 and 10:1, and (iii) a cation (e.g., a metal cation) in a molar ratio of cation to linaclotide between 100:1 and 40:1. In some embodiments, the composition comprises (i) between 0.01 and 5 wt. % of a polymer, (ii) a sterically hindered primary amine (e.g., an amino acid) in a molar ratio of primary amine to linaclotide between 100:1 and 50:1, and (iii) a cation (e.g., a metal cation) in a molar ratio of cation to linaclotide between 100:1 and 40:1. In some embodiments, the composition comprises (i) between 0.01 and 0.5 wt. % of a polymer selected from PVP and PVA, (ii) an amino acid selected from leucine, isoleucine, alanine, and methionine in a molar ratio of amino acid to linaclotide between 100:1 and 10:1, and (iii) a metal cation selected from $Ca^{2+}$, $Mg^{2+}$, and $Zn^{2+}$ in a molar ratio of cation to linaclotide between 100:1 and 40:1. In some embodiments, the composition comprises (i) between 0.01 and 5 wt. % of a polymer selected from PVP and PVA, (ii) an amino acid selected from leucine, isoleucine, alanine, and methionine in a molar ratio of amino acid to linaclotide between 100:1 and 50:1, and (iii) a metal cation selected from $Ca^{2+}$, $Mg^{2+}$, and $Zn^{2+}$ in a molar ratio of cation to linaclotide between 100:1 and 40:1.

In some embodiments, the composition comprises linaclotide (e.g., between 0.1 and 1% by weight, between 0.1 and 0.5% by weight or between 0.2 and 0.4% by weight of linaclotide), $Ca^{2+}$ or a salt thereof in a concentration between 1.2 and 1.8% by weight, leucine in a concentration between 0.5 and 0.9% by weight, and optionally between 0.5 and 0.9% by weight (e.g., between 0.6 and 0.75% by weight) of HPMC. In some embodiments, the composition comprises linaclotide (e.g., between 0.1 and 1% by weight, between 0.1 and 0.5% by weight or between 0.2 and 0.4% by weight of linaclotide), $Ca^{2+}$ or a salt thereof in a concentration between 1.4 and 1.65% by weight, leucine in a concentration between 0.5 and 0.8% by weight, and optionally between 0.5 and 0.9% by weight (e.g., between 0.6 and 0.75% by weight) of HPMC. In some embodiments, the composition comprises linaclotide (e.g., between 0.1 and 1% by weight, between 0.1 and 0.5% by weight or between 0.2 and 0.4% by weight of linaclotide), $Ca^{2+}$ or a salt thereof in a concentration between 1.45 and 1.65% by weight, leucine in a concentration between 0.6 and 0.75% by weight, and optionally between 0.5 and 0.9% by weight (e.g., between 0.6 and 0.75% by weight) of HPMC.

In some embodiments, the pharmaceutical composition comprises linaclotide, leucine in a molar ratio of leucine to linaclotide between 70:1 and 10:1 and $Ca^{2+}$ or a salt thereof in a molar ratio of $Ca^{2+}$ or a salt thereof to linaclotide between 100:1 and 30:1. In further embodiments, the composition comprises a molar ratio of $Ca^{2+}$ or a salt thereof to linaclotide between 100:1 and 40:1. In some embodiments, the composition comprises a molar ratio of leucine to linaclotide between 60:1 and 20:1 and a molar ratio of $Ca^{2+}$ or a salt thereof to linaclotide between 100:1 and 40:1. In some embodiments, the composition comprises a molar ratio of leucine to linaclotide between 40:1 and 20:1. In some embodiments, the composition comprises a molar ratio of leucine to linaclotide between 40:1 and 20:1. In some embodiments, the composition comprises a molar ratio of $Ca^{2+}$ or a salt thereof to leucine between 1.5:1 and 5:1. In still further embodiments, the composition releases at least 60% of the linaclotide contained therein within 15 minutes of entering a use environment. In some embodiments, the composition releases at least 70% of the linaclotide contained therein within 15 minutes of entering a use environment. In some embodiments, the composition releases at least 80% of the linaclotide contained therein within 15 minutes of entering a use environment. In some further embodiments, the composition comprises between 100 μg and 300 μg of linaclotide. In some embodiments, the composition comprises about 266 μg of linaclotide. In some embodiments, the composition comprises about 133 μg of linaclotide. In some embodiments, the composition further comprises hydroxypropyl methyl cellulose. In some embodiments, the composition is a capsule. In some embodiments, the composition is a tablet.

In some embodiments, the pharmaceutical composition comprises linaclotide, leucine in a molar ratio of leucine to linaclotide between 70:1 and 10:1, and $Ca^{2+}$ or a salt thereof in a molar ratio of $Ca^{2+}$ or a salt thereof to leucine between 1.5:1 and 5:1. In further embodiments, the composition comprises leucine in a molar ratio to linaclotide between 50:1 and 10:1. In some embodiments, the composition comprises leucine in molar ratio to linaclotide between 40:1 and 20:1.

The composition may also comprise any suitable pharmaceutically acceptable carrier or medium. Suitable pharmaceutically acceptable carriers include, for example, any solvents, dispersants, pH buffering agents, coatings, absorption promoting agents, controlled release agents, and one or more inert excipients (e.g., filling agents, starches, polyols, granulating agents, microcrystalline cellulose, diluents, lubricants, binders, disintegrating agents), or the like. In addition, the compositions can contain any desired additional components, additives, and/or species, for example, surface active additives, dispersing additives, humectants, suspending agents, solubilizers, buffering agents, disintegrants, preservatives, colorants, flavorants, and the like. In some embodiments, the composition comprises one or more ion species that interact with linaclotide.

The composition can also comprise any suitable pH buffering agent. In some embodiments, the pH buffering agent is present in the composition in an amount sufficient to achieve the isoelectric point of linaclotide. In some embodiments, the composition can have any desired pH. In some embodiments, the composition has a pH of 2 to 5 (for example, a pH of 2 to 4.5, a pH of 2 to 4, a pH of 2.5 to 4, a pH of 2.5 to 3.5, a pH of 2.5 to 3, or even a pH of 3).

The composition may also comprise any one or more filling agents. Suitable filling agents include, but are not limited to, starch, calcium carbonate, calcium sulfate, hydroxylpropylmethyl cellulose, fructose, methyl cellulose, dextrates, dextrose, lactitol, maltose, sucrose, sorbitol, isomalt, pregelatinized starch, dicalcium phosphate, microcrystalline cellulose, mannitol, gelatin, trehalose, erythritol, maltitol, lactose, glucose, or a combination thereof, or a mixture thereof. In some embodiments, the filling agent is isomalt. In some embodiments, the filling agent is gelatin. In some embodiments, the filling agent is mannitol. In some embodiments, the filling agent is pregelatinized starch. In some embodiments, the filling agent is microcrystalline cellulose. In some embodiments, the composition comprises a tablet filler and a granule filler.

The composition can comprise any suitable concentration of filling agent. In some embodiments, for example, the composition comprises one or more filling agents in a concentration of 0.1-95% by weight, relative to the total weight of the composition. In some embodiments, for example, the composition comprises one or more filling agents in a concentration of 1-90 wt. % of filling agent(s), relative to the total weight of the composition. In some embodiments, for example, the composition comprises one or more filling agents in a concentration of 10-90 wt. % of filling agent(s), relative to the total weight of the composition. In some embodiments, for example, the composition comprises one or more filling agents in a concentration of 20-90 wt. % of filling agent(s), relative to the total weight of the composition. In some embodiments, for example, the composition comprises one or more filling agents in a concentration of 30-80 wt. % of filling agent(s), relative to the total weight of the composition. In some embodiments, the composition comprises one or more filling agents in a concentration of at least 20 wt. %, for example, at least 40 wt. %, at least 60 wt. %, or at least 80 wt. %, relative to the total weight of the composition.

Suitable disintegrants include, for example, agar-agar, calcium carbonate, microcrystalline cellulose, croscarmellose sodium, crospovidone, povidone, polacrilin potassium, sodium starch glycolate, potato or tapioca starch, other starches, pre-gelatinized starch, clays, other algins, other celluloses, gums, and mixtures thereof. In some embodiments, the disintegrant is crospovidone. In some embodiments, the disintegrant is croscarmellose sodium.

Suitable lubricants include, for example, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil and soybean oil), zinc stearate, ethyl oleate, ethyl laurate, agar, syloid silica gel (AEROSIL 200, W.R. Grace Co., Baltimore, Md. USA), a coagulated aerosol of synthetic silica (Evonik Degussa Co., Plano, Tex. USA), a pyrogenic silicon dioxide (CAB-O-SIL, Cabot Co., Boston, Mass. USA), and mixtures thereof.

Suitable anti-caking additives include, for example, calcium silicate, magnesium silicate, silicon dioxide, colloidal silicon dioxide, talc, and mixtures thereof.

Suitable anti-microbial additives that may be used, e.g., as a preservative for the linaclotide compositions, include, for example, benzalkonium chloride, benzethonium chloride, benzoic acid, benzyl alcohol, butyl paraben, cetylpyridinium chloride, cresol, chlorobutanol, dehydroacetic acid, ethylparaben, methylparaben, phenol, phenylethyl alcohol, phenoxyethanol, phenylmercuric acetate, phenylmercuric nitrate, potassium sorbate, propylparaben, sodium benzoate, sodium dehydroacetate, sodium propionate, sorbic acid, thimersol, thymo, and mixtures thereof.

Suitable coating additives include, for example, sodium carboxymethyl cellulose, cellulose acetate phthalate, ethylcellulose, gelatin, pharmaceutical glaze, hydroxypropyl cellulose, hydroxypropyl methylcellulose, hydroxypropyl methyl cellulose phthalate, methylcellulose, polyethylene glycol, polyvinyl acetate phthalate, shellac, sucrose, titanium dioxide, carnauba wax, microcrystalline wax, and mixtures thereof. In some embodiments, coating additives are selected from sodium carboxymethyl cellulose, cellulose acetate phthalate, ethylcellulose, gelatin, pharmaceutical glaze, hydroxypropyl cellulose, methylcellulose, polyethylene glycol, polyvinyl acetate phthalate, shellac; sucrose, titanium dioxide, carnauba wax, microcrystalline wax, and mixtures thereof. In certain embodiments, suitable additives for the linaclotide composition include one or more of sucrose, talc, magnesium stearate, crospovidone or BHA. In certain embodiments, suitable coating additives for the linaclotide composition include one or more of magnesium stearate, crospovidone or BHA.

In some embodiments, the composition comprises linaclotide and a hydrolysis product, e.g., a hydrolysis product comprising or having a structure of:

(SEQ ID NO: 2)

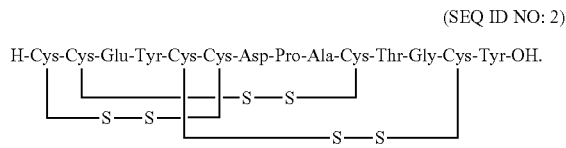

The composition can contain any desired concentration of the hydrolysis product. In some embodiments, the composition comprises less than 10 wt. % of the hydrolysis product. In some embodiments, the composition comprises less than 7 wt. % of the hydrolysis product. In some embodiments, the composition comprises less than 6 wt. % of the hydrolysis product. In some embodiments, the composition comprises less than 5 wt. % of the hydrolysis product. In some embodiments, the composition comprises less than 4 wt. % of the hydrolysis product. In some embodiments, the composition comprises less than 3 wt. % of the hydrolysis product. In some embodiments, the composition comprises less than 2 wt. % of the hydrolysis product. In some embodiments, the composition comprises less than 1 wt. % of the hydrolysis product. In some embodiments, the composition comprises between 0.01 and 10 wt. % of the hydrolysis product. In some embodiments, the composition comprises between 0.1 and 7 wt. % of the hydrolysis product. In some embodiments, the composition comprises between 0.1 and 5 wt. % of the hydrolysis product. In some embodiments, the composition comprises between 0.05 and 5 wt. % of the hydrolysis product. In some embodiments, the composition comprises between 0.5 and 5 wt. % of the hydrolysis product. In some embodiments, the composition comprises between 1 and 5 wt. % of the hydrolysis product. In some embodiments, the composition comprises between 0.1 and 4 wt. % of the hydrolysis product. In some embodiments, the composition comprises between 0.5 and 4 wt. % of the hydrolysis product. In some embodiments, the composition comprises between 1 and 4 wt. % of the hydrolysis product. In some embodiments, the composition comprises between 0.1 and 3 wt. % of the hydrolysis product. In some embodiments, the composition comprises between 0.5 and 3 wt. % of the hydrolysis product. In some embodiments, the composition comprises between 1 and 3 wt. % of the hydrolysis product. In some embodiments, the composition comprises between 0.1 and 2.5 wt. % of the hydrolysis product. In some embodiments, the composition comprises between 0.5 and 2.5 wt. % of the hydrolysis product. In some embodiments, the composition comprises between 1 and 2.5 wt. % of the hydrolysis product. In some embodiments, the composition comprises between 0.05 and 2 wt. % of the hydrolysis product. In some embodiments, the composition comprises between 0.1 and 2 wt. % of the hydrolysis product. In some embodiments, the composition comprises between 0.5 and 2 wt. % of the hydrolysis product. In some embodiments, the composition comprises between 1 and 2 wt. % of the hydrolysis product. In some embodiments, the composition comprises between 0.1 and 1.5 wt. % of the hydrolysis product. In some embodiments, the composition comprises between 0.5 and 1.5 wt. % of the hydrolysis product. In some embodiments, the composition comprises between 0.1 and 1 wt. % of the hydrolysis product. In some embodiments, the composition comprises between 0.5 and 1 wt. % of the hydrolysis product.

In some embodiments, the composition comprises linaclotide and a formaldehyde imine product, e.g., a formaldehyde imine product comprising or having a structure of:

(SEQ ID NO: 3)

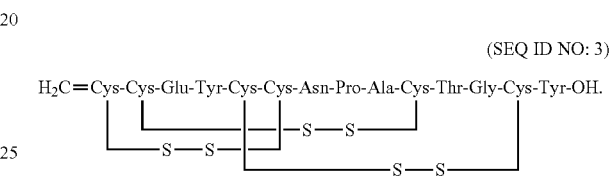

The composition can contain any desired concentration of the formaldehyde imine product. In some embodiments, the composition comprises less than 10 wt. % of the formaldehyde imine product. In some embodiments, the composition comprises less than 7 wt. % of the formaldehyde imine product. In some embodiments, the composition comprises less than 6 wt. % of the formaldehyde imine product. In some embodiments, the composition comprises less than 5 wt. % of the formaldehyde imine product. In some embodiments, the composition comprises less than 4 wt. % of the formaldehyde imine product. In some embodiments, the composition comprises less than 3 wt. % of the formaldehyde imine product. In some embodiments, the composition comprises less than 2 wt. % of the formaldehyde imine product. In some embodiments, the composition comprises less than 1 wt. % of the formaldehyde imine product. In some embodiments, the composition comprises between 0.01 and 10 wt. % of the formaldehyde imine product. In some embodiments, the composition comprises between 0.1 and 7 wt. % of the formaldehyde imine product. In some embodiments, the composition comprises between 0.1 and 5 wt. % of the formaldehyde imine product. In some embodiments, the composition comprises between 0.05 and 5 wt. % of the formaldehyde imine product. In some embodiments, the composition comprises between 0.5 and 5 wt. % of the formaldehyde imine product. In some embodiments, the composition comprises between 1 and 5 wt. % of the formaldehyde imine product. In some embodiments, the composition comprises between 0.1 and 4 wt. % of the formaldehyde imine product. In some embodiments, the composition comprises between 0.5 and 4 wt. % of the formaldehyde imine product. In some embodiments, the composition comprises between 1 and 4 wt. % of the formaldehyde imine product. In some embodiments, the composition comprises between 0.1 and 3 wt. % of the formaldehyde imine product. In some embodiments, the composition comprises between 0.5 and 3 wt. % of the formaldehyde imine product. In some embodiments, the composition comprises between 1 and 3 wt. % of the formaldehyde imine product. In some embodiments, the composition comprises between 0.1 and 2.5 wt. % of the formaldehyde imine product. In some embodiments, the composition comprises between 0.5 and 2.5 wt. % of the formaldehyde imine product. In some embodiments, the composition comprises between 1 and 2.5 wt. % of the formaldehyde imine product. In some embodiments, the composition comprises between 0.1 and 2 wt. % of the formaldehyde imine product. In some embodiments, the composition comprises between 0.05 and 2 wt. % of the formaldehyde imine product. In some embodiments, the composition comprises between 0.5 and 2 wt. % of the formaldehyde imine product. In some embodiments, the composition comprises between 1 and 2 wt. % of the formaldehyde imine product. In some embodiments, the composition comprises between 0.1 and 1.5 wt. % of the formaldehyde imine product. In some embodiments, the composition comprises between 0.5 and 1.5 wt. % of the formaldehyde imine product. In some embodiments, the composition comprises between 0.1 and 1 wt. % of the formaldehyde imine product. In some embodiments, the composition comprises between 0.5 and 1 wt. % of the formaldehyde imine product.

In some embodiments, the composition comprises linaclotide and an oxidation product, e.g., an oxidation product comprising or having a structure of:

(SEQ ID NO: 4)

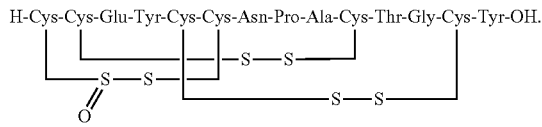

Alternatively, or in addition, the composition comprises linaclotide and an oxidation product having the depicted structure but wherein oxidation occurs at any one or more of the six depicted cysteinyl sulfurs. The composition can contain any desired concentration of the oxidation product. In some embodiments, the composition comprises less than 10 wt. % of the oxidation product. In some embodiments, the composition comprises less than 7 wt. % of the oxidation product. In some embodiments, the composition comprises less than 6 wt. % of the oxidation product. In some embodiments, the composition comprises less than 5 wt. % of the oxidation product. In some embodiments, the composition comprises less than 4 wt. % of the oxidation product. In some embodiments, the composition comprises less than 3 wt. % of the oxidation product. In some embodiments, the composition comprises less than 2 wt. % of the oxidation product. In some embodiments, the composition comprises less than 1 wt. % of the oxidation product. In some embodiments, the composition comprises between 0.01 and 10 wt. % of the oxidation product. In some embodiments, the composition comprises between 0.01 and 7 wt. % of the oxidation product. In some embodiments, the composition comprises between 0.01 and 5 wt. % of the oxidation product. In some embodiments, the composition comprises between 0.05 and 5 wt. % of the oxidation product. In some embodiments, the composition comprises between 0.5 and 5 wt. % of the oxidation product. In some embodiments, the composition comprises between 1 and 5 wt. % of the oxidation product. In some embodiments, the composition comprises between 0.1 and 4 wt. % of the oxidation product. In some embodiments, the composition comprises between 0.5 and 4 wt. % of the oxidation product. In some embodiments, the composition comprises between 1 and 4 wt. % of the oxidation product. In some embodiments, the composition comprises between 0.1 and 3 wt. % of the oxidation product. In some embodiments, the composition comprises between 0.5 and 3 wt. % of the oxidation product. In some embodiments, the composition comprises between 1 and 3 wt. % of the oxidation product. In some embodiments, the composition comprises between 0.1 and 2.5 wt. % of the oxidation product. In some embodiments, the composition comprises between 0.5 and 2.5 wt. % of the oxidation product. In some embodiments, the composition comprises between 1 and 2.5 wt. % of the oxidation product. In some embodiments, the composition comprises between 0.05 and 2 wt. % of the oxidation product. In some embodiments, the composition comprises between 0.1 and 2 wt. % of the oxidation product. In some embodiments, the composition comprises between 0.5 and 2 wt. % of the oxidation product. In some embodiments, the composition comprises between 1 and 2 wt. % of the oxidation product. In some embodiments, the composition comprises between 0.1 and 1.5 wt. % of the oxidation product. In some embodiments, the composition comprises between 0.5 and 1.5 wt. % of the oxidation product. In some embodiments, the composition comprises between 0.1 and 1 wt. % of the oxidation product. In some embodiments, the composition comprises between 0.5 and 1 wt. % of the oxidation product.

In some embodiments, the composition comprises linaclotide and an acetylation product, e.g. an acetylation product comprising or having:

(SEQ ID NO: 5)

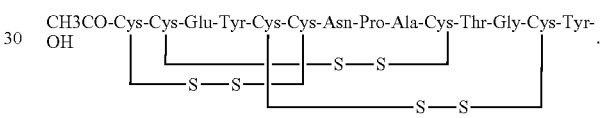

The composition can contain any desired concentration of the acetylation product. In some embodiments, the composition comprises less than 10 wt. % of the acetylation product. In some embodiments, the composition comprises less than 7 wt. % of the acetylation product. In some embodiments, the composition comprises less than 6 wt. % of the acetylation product. In some embodiments, the composition comprises less than 5 wt. % of the acetylation product. In some embodiments, the composition comprises less than 4 wt. % of the acetylation product. In some embodiments, the composition comprises less than 3 wt. % of the acetylation product. In some embodiments, the composition comprises less than 2 wt. % of the acetylation product. In some embodiments, the composition comprises less than 1 wt. % of the acetylation product. In some embodiments, the composition comprises between 0.01 and 10 wt. % of the acetylation product. In some embodiments, the composition comprises between 0.1 and 7 wt. % of the acetylation product. In some embodiments, the composition comprises between 0.1 and 5 wt. % of the acetylation product. In some embodiments, the composition comprises between 0.5 and 5 wt. % of the acetylation product. In some embodiments, the composition comprises between 1 and 5 wt. % of the acetylation product. In some embodiments, the composition comprises between 0.1 and 4 wt. % of the acetylation product. In some embodiments, the composition comprises between 0.5 and 4 wt. % of the acetylation product. In some embodiments, the composition comprises between 1 and 4 wt. % of the acetylation product. In some embodiments, the composition comprises between 0.1 and 3 wt. % of the acetylation product. In some embodiments, the composition comprises between 0.5 and 3 wt. % of the acetylation product. In some embodiments, the composition comprises between 1 and 3 wt. % of the acetylation product. In some embodiments, the composition comprises between 0.1 and 2.5 wt. % of the acetylation product. In some embodiments, the composition comprises between 0.5 and 2.5 wt. % of the acetylation product. In some embodiments, the composition comprises between 1 and 2.5 wt. % of the acetylation product. In some embodiments, the composition comprises between 0.1 and 2 wt. % of the acetylation product. In some embodiments, the composition comprises between 0.5 and 2 wt. % of the acetylation product. In some embodiments, the composition comprises between 1 and 2 wt. % of the acetylation product. In some embodiments, the composition comprises between 0.1 and 1.5 wt. % of the acetylation product. In some embodiments, the composition comprises between 0.5 and 1.5 wt. % of the acetylation product. In some embodiments, the composition comprises between 0.1 and 1 wt. % of the acetylation product. In some embodiments, the composition comprises between 0.5 and 1 wt. % of the acetylation product.

In some embodiments, the composition comprises linaclotide and any desired concentration of multimers. In some embodiments, the composition comprises less than 10 wt. % of multimer(s). In some embodiments, the composition comprises less than 7 wt. % of multimer(s). In some embodiments, the composition comprises less than 6 wt. % of multimer(s). In some embodiments, the composition comprises less than 5 wt. % of multimer(s). In some embodiments, the composition comprises less than 4 wt. % of multimer(s). In some embodiments, the composition comprises less than 3 wt. % of multimer(s). In some embodiments, the composition comprises less than 2 wt. % of multimer(s). In some embodiments, the composition comprises less than 1 wt. % of multimer(s). In some embodiments, the composition comprises between 0.01 and 10 wt. % of multimer(s). In some embodiments, the composition comprises between 0.1 and 7 wt. % of multimer(s). In some embodiments, the composition comprises between 0.1 and 5 wt. % of multimer(s). In some embodiments, the composition comprises between 0.5 and 5 wt. % of multimer(s). In some embodiments, the composition comprises between 1 and 5 wt. % of multimer(s). In some embodiments, the composition comprises between 0.1 and 4 wt. % of multimer(s). In some embodiments, the composition comprises between 0.5 and 4 wt. % of multimer(s). In some embodiments, the composition comprises between 1 and 4 wt. % of multimer(s). In some embodiments, the composition comprises between 0.1 and 3 wt. % of multimer(s). In some embodiments, the composition comprises between 0.5 and 3 wt. % of multimer(s). In some embodiments, the composition comprises between 1 and 3 wt. % of multimer(s). In some embodiments, the composition comprises between 0.1 and 2.5 wt. % of multimer(s). In some embodiments, the composition comprises between 0.5 and 2.5 wt. % of multimer(s). In some embodiments, the composition comprises between 1 and 2.5 wt. % of multimer(s). In some embodiments, the composition comprises between 0.1 and 2 wt. % of multimer(s). In some embodiments, the composition comprises between 0.5 and 2 wt. % of multimer(s). In some embodiments, the composition comprises between 1 and 2 wt. % of multimer(s). In some embodiments, the composition comprises between 0.1 and 1.5 wt. % of multimer(s). In some embodiments, the composition comprises between 0.5 and 1.5 wt. % of multimer(s). In some embodiments, the composition comprises between 0.1 and 1 wt. % of multimer(s). In some embodiments, the composition comprises between 0.5 and 1 wt. % of multimer(s).

In some embodiments, the composition comprises an effective amount of linaclotide and any desired amount of reduced form linaclotide. As used herein, the term "reduced form linaclotide" refers to linaclotide having no disulfide bonds between cysteine amino acids. In some embodiments, the composition comprises less than 10 wt. % of reduced form linaclotide. In some embodiments, the composition comprises less than 7 wt. % of reduced form linaclotide. In some embodiments, the composition comprises less than 6 wt. % of reduced form linaclotide. In some embodiments, the composition comprises less than 5 wt. % of reduced form linaclotide. In some embodiments, the composition comprises less than 4 wt. % of reduced form linaclotide. In some embodiments, the composition comprises less than 3 wt. % of reduced form linaclotide. In some embodiments, the composition comprises less than 2 wt. % of reduced form linaclotide. In some embodiments, the composition comprises less than 1 wt. % of reduced form linaclotide. In some embodiments, the composition comprises between 0.01 and 10 wt. % of reduced form linaclotide. In some embodiments, the composition comprises between 0.1 and 7 wt. % of reduced form linaclotide. In some embodiments, the composition comprises between 0.1 and 5 wt. % of reduced form linaclotide. In some embodiments, the composition comprises between 0.5 and 5 wt. % of reduced form linaclotide. In some embodiments, the composition comprises between 1 and 5 wt. % of reduced form linaclotide. In some embodiments, the composition comprises between 0.1 and 4 wt. % of reduced form linaclotide. In some embodiments, the composition comprises between 0.5 and 4 wt. % of reduced form linaclotide. In some embodiments, the composition comprises between 1 and 4 wt. % of reduced form linaclotide. In some embodiments, the composition comprises between 0.1 and 3 wt. % of reduced form linaclotide. In some embodiments, the composition comprises between 0.5 and 3 wt. % of reduced form linaclotide. In some embodiments, the composition comprises between 1 and 3 wt. % of reduced form linaclotide. In some embodiments, the composition comprises between 0.1 and 2.5 wt. % of reduced form linaclotide. In some embodiments, the composition comprises between 0.5 and 2.5 wt. % of reduced form linaclotide. In some embodiments, the composition comprises between 1 and 2.5 wt. % of reduced form linaclotide. In some embodiments, the composition comprises between 0.1 and 2 wt. % of reduced form linaclotide. In some embodiments, the composition comprises between 0.5 and 2 wt. % of reduced form linaclotide. In some embodiments, the composition comprises between 1 and 2 wt. % of reduced form linaclotide. In some embodiments, the composition comprises between 0.1 and 1.5 wt. % of reduced form linaclotide. In some embodiments, the composition comprises between 0.5 and 1.5 wt. % of reduced form linaclotide. In some embodiments, the composition comprises between 0.1 and 1 wt. % of reduced form linaclotide. In some embodiments, the composition comprises between 0.5 and 1 wt. % of reduced form linaclotide.

In some embodiments, the composition comprises an effective amount of linaclotide and any desired amount of scrambled form linaclotide. As used herein, the term "scrambled form linaclotide" refers to linaclotide having disulfide bonds between $Cys_1$ and $Cys_{10}$, between $Cys_1$ and $Cys_{13}$, between $Cys_1$ and $Cys_5$, between $Cys_1$ and $Cys_2$, between $Cys_2$ and $Cys_6$, between $Cys_2$ and $Cys_{13}$, between $Cys_2$ and $Cys_5$, between $Cys_5$ and $Cys_6$, and/or between $Cys_5$ and $Cys_{10}$. In some embodiments, the composition comprises less than 10 wt. % of scrambled form linaclotide. In some embodiments, the composition comprises less than 7 wt. % of scrambled form linaclotide. In some embodiments, the composition comprises less than 6 wt. % of scrambled form linaclotide. In some embodiments, the composition comprises less than 5 wt. % of scrambled form linaclotide. In some embodiments, the composition comprises less than 4 wt. % of scrambled form linaclotide. In some embodiments, the composition comprises less than 3 wt. % of scrambled form linaclotide. In some embodiments, the composition comprises less than 2 wt. % of scrambled form linaclotide. In some embodiments, the composition comprises less than 1 wt. % of scrambled form linaclotide. In some embodiments, the composition comprises between 0.01 and 10 wt. % of scrambled form linaclotide. In some embodiments, the composition comprises between 0.1 and 7 wt. % of scrambled form linaclotide. In some embodiments, the composition comprises between 0.1 and 5 wt. % of scrambled form linaclotide. In some embodiments, the composition comprises between 0.5 and 5 wt. % of scrambled form linaclotide. In some embodiments, the composition comprises between 1 and 5 wt. % of scrambled form linaclotide. In some embodiments, the composition comprises between 0.1 and 4 wt. % of scrambled form linaclotide. In some embodiments, the composition comprises between 0.5 and 4 wt. % of scrambled form linaclotide. In some embodiments, the composition comprises between 1 and 4 wt. % of scrambled form linaclotide. In some embodiments, the composition comprises between 0.1 and 3 wt. % of scrambled form linaclotide. In some embodiments, the composition comprises between 0.5 and 3 wt. % of scrambled form linaclotide. In some embodiments, the composition comprises between 1 and 3 wt. % of scrambled form linaclotide. In some embodiments, the composition comprises between 0.1 and 2.5 wt. % of scrambled form linaclotide. In some embodiments, the composition comprises between 0.5 and 2.5 wt. % of scrambled form linaclotide. In some embodiments, the composition comprises between 1 and 2.5 wt. % of scrambled form linaclotide. In some embodiments, the composition comprises between 0.1 and 2 wt. % of scrambled form linaclotide. In some embodiments, the composition comprises between 0.5 and 2 wt. % of scrambled form linaclotide. In some embodiments, the composition comprises between 1 and 2 wt. % of scrambled form linaclotide. In some embodiments, the composition comprises between 0.1 and 1.5 wt. % of scrambled form linaclotide. In some embodiments, the composition comprises between 0.5 and 1.5 wt. % of scrambled form linaclotide. In some embodiments, the composition comprises between 0.1 and 1 wt. % of scrambled form linaclotide. In some embodiments, the composition comprises between 0.5 and 1 wt. % of scrambled form linaclotide.

In some embodiments, the composition comprises a total degradant concentration of less than about 10 wt. %. In some embodiments, the composition comprises a total degradant concentration of less than about 8 wt. %. In some embodiments, the composition comprises a total degradant concentration of less than about 7 wt. %. In some embodiments, the composition comprises a total degradant concentration of less than about 6.5 wt. %. In some embodiments, the composition comprises a total degradant concentration of less than about 6 wt. %. In some embodiments, the composition comprises a total degradant concentration of less than about 5.5 wt. %. In some embodiments, the composition comprises a total degradant concentration of less than about 5 wt. %. In some embodiments, the composition comprises a total degradant concentration of less than about 4 wt. %. In some embodiments, the composition comprises a total degradant concentration of less than about 3 wt. %. In some embodiments, the composition comprises a total degradant concentration of less than about 2.5 wt. %. In some embodiments, the composition comprises a total degradant concentration of less than about 2 wt. %. In some embodiments, the composition comprises a total degradant concentration of less than about 1 wt. %.

The composition can comprise any effective amount of linaclotide. In some embodiments, for example, the composition comprises from 0.05 µg to 6 mg of linaclotide. In some embodiments, for example, the composition comprises from 0.1 µg to 6 mg of linaclotide. In some embodiments, for example, the composition comprises from 25 µg to 6 mg of linaclotide. In some embodiments, the composition comprises from 25 µg to 2 mg of linaclotide, for example, from 50 µg to 1 mg of linaclotide. In some embodiments, the composition comprises from 50 µg to 2 mg of linaclotide. In some embodiments, for example, the composition comprises from 0.1 µg to 90 µg of linaclotide. In some embodiments, for example, the composition comprises from 0.1 µg to 45 µg of linaclotide. In some embodiments, for example, the composition comprises from 0.1 µg to 25 µg of linaclotide. In some embodiments, the composition comprises 0.05 µg, 0.1 µg, 0.25 µg, 0.5 µg, 0.75 µg, 1 µg, 1.5 µg, 2 µg, 2.5 µg, 3 µg, 3.5 µg, 4 µg, 4.5 µg, 5 µg, 7.5 µg, 10 µg, 15 µg, 20 µg, 25 µg, 30 µg, 35 µg, 40 µg, 45 µg, 50 µg, 60 µg, 75 µg, 90 µg, 100 µg, 150 µg, 200 µg, 250 µg, 300 µg, 350 µg, 400 µg, 450 µg, 500 µg, 550 µg, 600 µg, 650 µg, 700 µg, 750 µg, 800 µg, 850 µg, 900 µg, 950 µg or 1 mg of linaclotide. In some embodiments, the composition comprises from 100 µg to 600 µg of linaclotide. In some embodiments, the composition comprises 50 µg, 100 µg, 150 µg, 200 µg, 300 µg, 400 µg, 500 µg or 600 µg of linaclotide. In some embodiments, the composition comprises 75 µg, 150 µg, 300 µg, or 600 µg of linaclotide.

In some embodiments, the composition comprises 75 µg of linaclotide. In some embodiments, the composition comprises about 133 µg of linaclotide. In some embodiments, the composition comprises 150 µg of linaclotide. In some embodiments, the composition comprises about 266 µg of linaclotide. In some embodiments, the composition comprises 300 µg of linaclotide. In some embodiments, the composition comprises 600 µg of linaclotide. In some embodiments, the composition comprises 0.1 µg, 0.25 µg, 0.5 µg, or 0.75 µg of linaclotide. In some embodiments, the composition comprises 0.1 µg of linaclotide. In some embodiments, the composition comprises 0.25 µg of linaclotide. In some embodiments, the composition comprises 0.5 µg of linaclotide. In some embodiments, for example, the composition comprises from 0.05 µg to 25 µg of linaclotide.

The composition can be in any desired form, such as, for example, any desired solid form for oral administration. Examples of suitable solid dosage forms include, without limitation, tablets, capsules, gelcaps, sachets, pellets, caplets, granules, lozenges and bulk powders. In some embodiments, the composition can be in the form selected from pellets, caplets, granules, lozenges and bulk powders.

In some embodiments, the composition is an immediate release composition (for example, an immediate release tablet or an immediate release capsule). The immediate release composition can have any desired dissolution rate. In some embodiments, the composition releases at least 80% of the linaclotide contained therein within 30 minutes of entering a use environment. In some embodiments, the composition releases at least 85% of the linaclotide contained therein within 30 minutes of entering a use environment. In some embodiments, the composition releases at least 90% of the linaclotide contained therein within 30 minutes of entering a use environment. In some embodiments, the composition releases at least 95% of the linaclotide contained therein within 30 minutes of entering a use environment. In some embodiments, the composition releases at least 50% of the linaclotide contained therein within 15 minutes of entering a use environment. In some embodiments, the composition releases at least 60% of the linaclotide contained therein within 15 minutes of entering a use environment. In some embodiments, the composition releases at least 70% of the linaclotide contained therein within 15 minutes of entering a use environment. In some embodiments, the composition releases at least 80% of the linaclotide contained therein within 15 minutes of entering a use environment. In some embodiments, the composition releases at least 85% of the linaclotide contained therein within 15 minutes of entering a use environment. In some embodiments, the composition releases at least 90% of the linaclotide contained therein within 15 minutes of entering a use environment. In some embodiments, the composition releases at least 95% of the linaclotide contained therein within 15 minutes of entering a use environment.

In some embodiments, the composition releases at least 80% of the linaclotide contained therein within 30 minutes of entering an agitated buffer solution (e.g., phosphate buffer solution) having a pH of 4.5. In some embodiments, the composition releases at least 85% of the linaclotide contained therein within 30 minutes of entering an agitated buffer solution having a pH of 4.5. In some embodiments, the composition releases at least 90% of the linaclotide contained therein within 30 minutes of entering an agitated buffer solution having a pH of 4.5. In some embodiments, the composition releases at least 95% of the linaclotide contained therein within 30 minutes of entering an agitated buffer solution having a pH of 4.5. In some embodiments, the composition releases at least 50% of the linaclotide contained therein within 15 minutes of entering an agitated buffer solution having a pH of 4.5. In some embodiments, the composition releases at least 60% of the linaclotide contained therein within 15 minutes of entering an agitated buffer solution having a pH of 4.5. In some embodiments, the composition releases at least 70% of the linaclotide contained therein within 15 minutes of entering an agitated buffer solution having a pH of 4.5. In some embodiments, the composition releases at least 80% of the linaclotide contained therein within 15 minutes of entering an agitated buffer solution having a pH of 4.5. In some embodiments, the composition releases at least 85% of the linaclotide contained therein within 15 minutes of entering an agitated buffer solution having a pH of 4.5. In some embodiments, the composition releases at least 90% of the linaclotide contained therein within 15 minutes of entering an agitated buffer solution having a pH of 4.5. In some embodiments, the composition releases at least 95% of the linaclotide contained therein within 15 minutes of entering an agitated buffer solution having a pH of 4.5. The buffer solution can be agitated using USP Apparatus II (Paddle) at 50 rpm, a USP Apparatus I at 100 rpm, or the like.

In some embodiments, the composition releases at least 80% of the linaclotide contained therein within 30 minutes of entering an agitated solution of 0.1 N HCL. In some embodiments, the composition releases at least 85% of the linaclotide contained therein within 30 minutes of entering an agitated solution of 0.1 N HCL. In some embodiments, the composition releases at least 90% of the linaclotide contained therein within 30 minutes of entering an agitated solution of 0.1 N HCL. In some embodiments, the composition releases at least 95% of the linaclotide contained therein within 30 minutes of entering an agitated solution of 0.1 N HCL. In some embodiments, the composition releases at least 50% of the linaclotide contained therein within 15 minutes of entering an agitated solution of 0.1 N HCL. In some embodiments, the composition releases at least 60% of the linaclotide contained therein within 15 minutes of entering an agitated solution of 0.1 N HCL. In some embodiments, the composition releases at least 70% of the linaclotide contained therein within 15 minutes of entering an agitated solution of 0.1 N HCL. In some embodiments, the composition releases at least 80% of the linaclotide contained therein within 15 minutes of entering an agitated solution of 0.1 N HCL. In some embodiments, the composition releases at least 85% of the linaclotide contained therein within 15 minutes of entering an agitated solution of 0.1 N HCL. In some embodiments, the composition releases at least 90% of the linaclotide contained therein within 15 minutes of entering an agitated solution of 0.1 N HCL. In some embodiments, the composition releases at least 95% of the linaclotide contained therein within 15 minutes of entering an agitated solution of 0.1 N HCL. In some embodiments, the composition releases at least 50% of the linaclotide contained therein within 5 minutes of entering an agitated solution of 0.1 N HCL. In some embodiments, the composition releases at least 60% of the linaclotide contained therein within 5 minutes of entering an agitated solution of 0.1 N HCL. In some embodiments, the composition releases at least 70% of the linaclotide contained therein within 5 minutes of entering an agitated solution of 0.1 N HCL. In some embodiments, the composition releases at least 80% of the linaclotide contained therein within 5 minutes of entering an agitated solution of 0.1 N HCL. In some embodiments, the composition releases at least 85% of the linaclotide contained therein within 5 minutes of entering an agitated solution of 0.1 N HCL. In some embodiments, the composition releases at least 90% of the linaclotide contained therein within 5 minutes of entering an agitated solution of 0.1 N HCL. In some embodiments, the composition releases at least 95% of the linaclotide contained therein within 5 minutes of entering an agitated solution of 0.1 N HCL. The solution can be agitated using. USP Apparatus II (Paddle) at 50 rpm, a USP Apparatus I at 100 rpm, or the like.

In some embodiments, the composition releases at least 80% of the linaclotide contained therein within 30 minutes of entering an agitated buffer solution having a pH of 6.8. In some embodiments, the composition releases at least 85% of the linaclotide contained therein within 30 minutes of entering an agitated buffer solution having a pH of 6.8. In some embodiments, the composition releases at least 90% of the linaclotide contained therein within 30 minutes of entering an agitated buffer solution having a pH of 6.8. In some embodiments, the composition releases at least 95% of the linaclotide contained therein within 30 minutes of entering an agitated buffer solution having a pH of 6.8. In some embodiments, the composition releases at least 80% of the linaclotide contained therein within 15 minutes of entering an agitated buffer solution having a pH of 6.8. In some embodiments, the composition releases at least 85% of the linaclotide contained therein within 15 minutes of entering an agitated buffer solution having a pH of 6.8. In some embodiments, the composition releases at least 90% of the linaclotide contained therein within 15 minutes of entering an agitated buffer solution having a pH of 6.8. In some embodiments, the composition releases at least 95% of the linaclotide contained therein within 15 minutes of entering an agitated buffer solution having a pH of 6.8. The buffer solution can be agitated using USP Apparatus II (Paddle) at 50 rpm, a USP Apparatus I at 100 rpm, or the like.

In some embodiments, the composition releases at least 80% of the linaclotide contained therein within 30 minutes of entering an agitated solution of simulated intestinal fluid without enzymes. In some embodiments, the composition releases at least 85% of the linaclotide contained therein within 30 minutes of entering an agitated solution of simulated intestinal fluid without enzymes. In some embodiments, the composition releases at least 90% of the linaclotide contained therein within 30 minutes of entering an agitated solution of simulated intestinal fluid without enzymes. In some embodiments, the composition releases at least 95% of the linaclotide contained therein within 30 minutes of entering an agitated solution of simulated intestinal fluid without enzymes. In some embodiments, the composition releases at least 80% of the linaclotide contained therein within 15 minutes of entering an agitated solution of simulated intestinal fluid without enzymes. In some embodiments, the composition releases at least 85% of the linaclotide contained therein within 15 minutes of entering an agitated solution of simulated intestinal fluid without enzymes. In some embodiments, the composition releases at least 90% of the linaclotide contained therein within 15 minutes of entering an agitated solution of simulated intestinal fluid without enzymes. In some embodiments, the composition releases at least 95% of the linaclotide contained therein within 15 minutes of entering an agitated solution of simulated intestinal fluid without enzymes. The solution can be agitated using USP Apparatus II (Paddle) at 50 rpm, a USP Apparatus I at 100 rpm, or the like.

The compositions may be prepared in any suitable manner, such as described, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition). For example, the compositions can be prepared using a method comprising: (a) providing a solution, e.g., an aqueous solution comprising linaclotide, or a pharmaceutically acceptable salt thereof, and stabilizing amount(s) of polymer, sterically hindered primary amine and/or cation component(s) and optionally other excipients; (b) applying the aqueous solution to a pharmaceutically acceptable filler to generate linaclotide-coated filler (e.g., by spraying, mixing or coating the pharmaceutically acceptable filler with the coating solution); and optionally (c) compressing the linaclotide-coated filler into tablets. The method can optionally include one or more of: (i) blending the linaclotide-coated filler with a pharmaceutically acceptable glidant, a pharmaceutically acceptable lubricant, or a pharmaceutically acceptable additive that acts as both a glidant and lubricant; (ii) blending the linaclotide-coated filler with filler that is not linaclotide-coated, (iii) blending the linaclotide-coated filler with other additives; (iv) applying a pharmaceutically acceptable coating additive to the linaclotide-coated filler; and optionally (v) compressing the linaclotide-coated filler into tablets. The final pharmaceutical composition can be placed into any suitable formulation, such as capsules (e.g., gelatin capsules) or tablets.

The composition can also be used to treat diseases, disorders, or conditions that are responsive to treatment with agonists of the GC-C receptor. The composition can be used to treat any gastrointestinal disorders and/or conditions in a patient (e.g., mammal or human) or inflammation or pain associated therewith. Suitable such gastrointestinal disorders and conditions, include, but are not limited to, irritable bowel syndrome, constipation-predominant irritable bowel syndrome, dyspepsia (including functional dyspepsia or non-ulcer dyspepsia), gastrointestinal motility disorders, functional gastrointestinal disorders, gastroesophageal reflux disease (GERD), Crohn's disease, ulcerative colitis, inflammatory bowel disease, functional heartburn, gastroparesis, chronic intestinal pseudo-obstruction (or colonic pseudo-obstruction), and disorders and conditions associated with constipation, for example, chronic constipation, opioid induced constipation, post-surgical constipation (post-operative ileus), and constipation associated with neuropathic disorders or a combination of symptoms thereof (such as a combination of irritable bowel syndrome and chronic constipation). In some embodiments, a method is provided for treating gastrointestinal disorders in a patient (e.g., mammal or human) diagnosed with one or more gastrointestinal disorders or conditions, wherein the method comprises administering an effective amount of the composition to the patient.

In another embodiment, a method is provided for increasing intestinal motility in a patient in need thereof, comprising administering an effective amount of the composition to the patient. Intestinal motility involves spontaneous coordinated dissentions and contractions of the stomach, intestines, colon and rectum to move food through the gastrointestinal tract during the digestive process.

In exemplary embodiments, the methods may comprise administering a therapeutically effective amount of the pharmaceutical composition to a patient in need thereof.

An effective amount of a composition comprising linaclotide or a pharmaceutically acceptable salt thereof required to achieve desired results (such as desired treatment and/or symptom relief) of a subject is dependent on several understood factors, such as the identity and severity of the disorder being treated, as well as the age, weight, etc., of the patient being treated.

A subject or patient in whom administration of the pharmaceutical composition is an effective therapeutic regimen for a disease or disorder is preferably a human, but can be any animal, including a laboratory animal in the context of a clinical trial or screening or activity experiment. Thus, as can be readily appreciated by one of ordinary skill in the art, the methods, compounds and compositions described herein are particularly suited for administration to any animal, particularly a mammal, and including, but by no means limited to, humans, rodents and non-rodents, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., e.g., for veterinary medical use.

In some embodiments, the effective dose range of linaclotide for adult humans is from 25 μg to 6 mg per day orally. In some embodiments, the dose range is 25 μg to 2 mg per day orally. In some embodiments, the dose range for adult humans is 50 μg to 1 mg per day orally (e.g., 50 μg, 100 μg, 150 μg, 200 μg, 250 μg, 300 μg, 350 μg, 400 μg, 450 μg, 500 μg, 550 μg, 600 μg, 650 μg, 700 μg, 750 μg, 800 μg, 850 μg, 900 μg, 950 μg or 1 mg). In some embodiments, the dose range is 100 μg to 600 μg per day orally. In some embodiments, the dose is 50 μg, 100 μg, 150 μg, 200 μg, 300 μg, 400 μg, 500 μg or 600 μg linaclotide per day orally. In some embodiments, the dose is 50 μg linaclotide per day orally. In some embodiments, the dose is 100 μg linaclotide per day orally. In some embodiments, the dose is 150 μg linaclotide per day orally. In some embodiments, the dose is 200 μg linaclotide per day orally. In some embodiments, the dose is 300 μg linaclotide per day orally. In some embodiments, the dose is 400 μg linaclotide per day orally. In some embodiments, the dose is 500 μg linaclotide per day orally. In some embodiments, the dose is 600 μg linaclotide per day orally. In some embodiments, the effective pediatric dose range of linaclotide is from 0.05 μg to 2 mg per day orally. In some embodiments, the effective pediatric dose range of linaclotide is from 0.05 μg to 100 μg per day orally. In some embodiments, the effective pediatric dose range of linaclotide is from 0.1 μg to 90 μg per day orally.

In some embodiments, the effective pediatric dose range of linaclotide is from 0.1 µg to 50 µg per day orally. In some embodiments, the effective pediatric dose range of linaclotide is from 0.1 µg to 25 µg per day orally. In some embodiments, the effective pediatric dose range of linaclotide is from 0.1 µg to 10 µg per day orally. In some embodiments, the effective pediatric dose range of linaclotide is from 0.1 µg to 5 µg per day orally. In some embodiments, the effective pediatric dose range of linaclotide is from 0.1 µg to 1 µg per day orally. In some embodiments, the effective pediatric dose range of linaclotide is from 0.1 µg to 0.5 µg per day orally. In some embodiments, the effective pediatric dose range of linaclotide is 0.1 µg per day orally. In some embodiments, the effective pediatric dose range of linaclotide is 0.25 µg per day orally. In some embodiments, the effective pediatric dose range of linaclotide is 0.5 µg per day orally. In some embodiments, the effective pediatric dose range of linaclotide is 3.5 µg per day orally. In some embodiments, the effective pediatric dose range of linaclotide is 15 µg per day orally. In some embodiments, the effective pediatric dose range of linaclotide is 45 µg per day orally. In some embodiments, the effective pediatric dose range of linaclotide is 60 µg per day orally. In some embodiments, the effective pediatric dose range of linaclotide is 90 µg per day orally. In some embodiments, the unit dosage form and daily dose are equivalent. In some embodiments, the unit dosage form is administered with food at anytime of the day, without food at anytime of the day, with food after an overnight fast (e.g., with breakfast). In some embodiments, the unit dosage form is administered once a day, twice a day or three times a day. In some embodiments, one, two or three unit dosage forms will contain the daily oral dose of linaclotide. The precise amount of compound administered to a patient will be the responsibility of the attendant physician. However, the dose employed will depend on a number of factors, including the age and sex of the patient, the precise disorder being treated, and its severity.

In some embodiments, the compositions are administered as a monotherapy. In some embodiments, the composition consists essentially of an effective amount of linaclotide. In some embodiments, the composition consists of an effective amount of linaclotide.

In other embodiments, the compositions are administered as part of a combination therapy. For example, a composition may be used in combination with other drugs or therapies that are used in the treatment, prevention, suppression, and/or amelioration of the diseases or conditions for which compounds of the invention are useful. The linaclotide can be co-administered or co-formulated with other medications. In one embodiment, the linaclotide composition can be co-administered with other medications used to treat gastrointestinal disorders including but not limited to acid suppressing agents such as Histamine-2 receptor agonists (H2As) and/or proton pump inhibitors (PPIs).

Such other drug(s) may be administered, by a route and in an amount commonly used therefore, contemporaneously or sequentially with a compound of the invention. When a compound of the present invention is used contemporaneously with one or more other drugs, a pharmaceutical unit dosage form containing such other drugs in addition to the compound of the invention may be employed. Accordingly, the pharmaceutical compositions of the present invention include those that also contain one or more other active components, in addition to a compound of invention.

Several methods can be used for evaluating the bioactivity of the linaclotide composition, including, but not limited to, immunoassays (e.g., enzyme-linked immunosorbent assay), radioimmuno assays, immunoradiometric assays, gel electrophoresis (e.g., SDS-PAGE), high performance liquid chromatography (HPLC), and/or high performance capillary electrophoresis (HPCE). In some embodiments, the bioactivity of the composition is assessed by a method comprising fixing linaclotide, incubating linaclotide with guanylate cyclase C (GCC), incubating GCC bound linaclotide with antibodies against GCC, incubating GCC antibody-bound linaclotide with fluorescently labeled antibodies against GCC antibodies, and detecting the linaclotide bound to the GCC antibodies by measuring the fluorescence intensity using a plate reader. The drug concentration can then be calculated based on the fluorescence reading of the solution.

For example, the bioactivity of the linaclotide compositions can be assessed and quantified using the following method, though other methods are available. The composition is added to a volumetric flask containing 60 ml of phosphate buffer having a pH of 4.5, and the flask is shaken for 60 minutes. 0.2 ml of the supernatant is then removed, and is added into one or more wells of a 96-well plate that is coated with GCC. The plate is sealed and incubated at 37° C. for 2 hr. At the end of incubation, the sample is removed and the plate is washed with phosphate buffered saline (PBS). The bound linaclotide is then incubated for 1 hour, at room temperature, with GCC (such as is available from Sigma-Aldrich Inc.) labeled with fluorescein isocyanate (FITC) in blocking buffer. After incubation, the well is washed with PBS. The fluorescence intensity of the end product is detected, for example, by using a plate reader. The linaclotide concentration is then calculated based on the fluorescence reading of the solution.

DEFINITIONS

As used herein, unless otherwise indicated, "linaclotide" refers to a peptide that consists of the amino acid sequence $Cys_1$ $Cys_2$ $Glu_3$ $Tyr_4$ $Cys_5$ $Cys_6$ $Asn_7$ $Pro_8$ $Ala_9$ $Cys_{10}$ $Thr_{11}$ $Gly_{12}$ $Cys_{13}$ $Tyr_{14}$ ("linaclotide"; SEQ ID NO: 1), as well as any pharmaceutically acceptable salts or hydrates thereof, any isolated and purified forms thereof, or disulfide forms thereof. "Disulfide forms" of linaclotide are defined herein as linaclotide having one, two, or three of the following disulfide bonds between cysteinyl amino acids: a disulfide bond between $Cys_1$ and $Cys_6$, a disulfide bond between $Cys_2$ and $Cys_{10}$, and/or a disulfide bond between $Cys_5$ and $Cys_{13}$. For example, disulfide forms of linaclotide can comprise disulfide bonds between $Cys_1$ and $Cys_6$ and between $Cys_2$ and $Cys_{10}$. In addition, disulfide forms of linaclotide can comprise disulfide bonds between $Cys_1$ and $Cys_6$ and between $Cys_5$ and $Cys_{13}$. Moreover, disulfide forms of linaclotide can comprise disulfide bonds between $Cys_2$ and $Cys_{10}$ and between $Cys_5$ and $Cys_{13}$.

As used herein, unless otherwise indicated, the term "isolated and purified" means at least 95 percent pure (for example, at least 96% pure, at least 97% pure, at least 98% pure, or even at least 99% pure), as measured, for example, by chromatographic purity using HPLC.

The term "released from", when referring to the release of linaclotide from the composition, unless otherwise indicated, is used herein to mean that the linaclotide no longer remains in a composition form.

As used herein, unless otherwise indicated, "stabilizing agent" refers to a polymer, sterically hindered primary amine (e.g., amino acid), or cation (e.g., metal cation) component of the composition which is included in the composition in a stabilizing amount. For example, a polymeric stabilizing agent is a polymer that is included in the composition in a stabilizing amount. Similarly, a sterically hindered primary amine stabilizing agent is a sterically hindered primary amine that is included in the composition in a stabilizing amount. Moreover, a cationic stabilizing agent is a cation that is included in the composition in a stabilizing amount.

As used herein, unless otherwise indicated, "stabilizing amount" refers to a concentration, within the composition, of a polymer, sterically hindered primary amine (e.g., amino acid), or cation component at which the component increases the stability of linaclotide in the composition, as compared to a similar composition not having a stabilizing amount of the same component.

As used herein, unless otherwise indicated, the term "entry into a use environment" means contact of the composition with saliva, gastric fluids, or enteric fluids of the patient to whom it is administered, or with a fluid intended to simulate saliva, gastric fluid, or enteric fluid for example an agitated buffer solution have a pH of 4.5, an agitated 0.1 N HCL solution, an agitated buffer solution having a pH of 6.8, or an agitated solution of simulated intestinal fluid without enzymes.

As used herein, unless otherwise indicated, the term "agitated", when used to refer to a solution means that the solution is agitated using USP Apparatus II at 50 rpm, USP Apparatus I at 100 rpm, or the like.

As used herein, unless otherwise indicated, "therapeutically effective amount" means the amount of a linaclotide or a pharmaceutically acceptable salt thereof that, when administered to a mammal for treating a state, disorder or condition, is sufficient to effect a treatment (as defined below). The "therapeutically effective amount" will vary depending on the compound, the disease and its severity and the age, sex, weight, physical condition and responsiveness of the mammal to be treated. For example, a therapeutically effective amount of linaclotide, or its pharmaceutically acceptable salt or hydrate, can be an amount effective to treat gastrointestinal disorders, including irritable bowel syndrome, constipation-predominant irritable bowel syndrome, chronic constipation, opioid induced constipation and/or dyspepsia.

As used herein, unless other indicated, "pharmaceutically acceptable" means biologically or pharmacologically compatible for in vivo use in animals or humans, and preferably means, approved by a regulatory agency of the Federal or a state government or listed in the U.S. Pharmacopeia or other generally recognized pharmacopeia for use in animals, and more particularly in humans.

As used herein, unless otherwise indicated, the term "treat", in all its verb forms, is used herein to mean to relieve, alleviate, prevent, and/or manage at least one symptom of a disorder in a subject, the disorder including, for example, a gastrointestinal disorder, such as, irritable bowel syndrome, constipation-predominant irritable bowel syndrome, chronic constipation, opioid induced constipation, dyspepsia, or a combination of symptoms thereof. Within the meaning of the present invention, the term "treat" also denotes, to arrest, delay the onset (i.e., the period prior to clinical manifestation of a disease) and/or reduce the risk of developing or worsening a disease. The term "treatment" means the act of "treating" as defined above.

As used herein, unless otherwise indicated, the term "additives" refers to a pharmaceutically acceptable additive. Pharmaceutically acceptable additives include, without limitation, binders, disintegrants, dispersing additives, lubricants, glidants, antioxidants, coating additives, diluents, surfactants, flavoring additives, humectants, absorption promoting additives, controlled release additives, anti-caking additives, anti-microbial agents (e.g., preservatives), colorants, desiccants, plasticizers and dyes.

As used herein, unless otherwise indicated, an "excipient" is any pharmaceutically acceptable additive, filler, binder or agent.

As used herein, unless otherwise indication, "stressed conditions" refer to 40° C. and 75% relative humidity (RH).

As used here, unless otherwise indicated, the terms "about" and "approximately" mean within an acceptable error range for the particular value as determined by one of ordinary skill in the art, which will depend, in part, on how the value is measured or determined, i.e., the limitations of the measurement system. For example, "about" can mean within 1 or more than 1 standard deviation, per practice in the art. Alternatively, "about" with respect to the compositions can mean plus or minus a range of up to 20%, preferably up to 10%. Alternatively, particularly with respect to biological systems or processes, the term can mean within an order of magnitude, preferably within 5-fold, and more preferably within 2-fold, of a value. Particular values are described in the application and claims, unless otherwise stated the term "about" means within an acceptable error range for the particular value.

All weight percentages (i.e., "% by weight" and "wt. %" and w/w) referenced herein, unless otherwise indicated, are measured relative to the total weight of the pharmaceutical composition.

The term "consisting essentially of", and variants thereof, when used to refer to the composition, are used herein to mean that the composition includes linaclotide and other desired pharmaceutically inactive additives, excipients, and/or components (e.g., polymers, sterically hindered primary amines, cations, filling agents, binders, carriers, excipients, diluents, disintegrating additives, lubricants, solvents, dispersants, coating additives, absorption promoting additives, hydrolysis products, formaldehyde imine products, oxidation products, acetylation products, deamidation products, multimers, controlled release additives, anti-caking additives, anti-microbial additives, preservatives, sweetening additives, colorants, flavors, desiccants, plasticizers, dyes, or the like), and no other active pharmaceutical ingredient(s).

EXAMPLES

The following examples are merely illustrative of the present invention and should not be construed as limiting the scope of the invention in any way as many variations and equivalents that are encompassed by the present invention will become apparent to those skilled in the art upon reading the present disclosure.

The following tests were employed in the examples section, unless otherwise indicated:

1) Stability of Linaclotide Compositions.

For stability evaluation, linaclotide compositions (0.15 mg theoretical, actual 0.135 mg) were packaged into a HDPE bottle with desiccant, and stored under at 40° C./75% RH ("stressed conditions"). The amount of linaclotide was assayed initially and after 3, 6, 9, 12, or 18 months of storage at stressed conditions. The concentration of linaclotide was analyzed and quantified using an HPLC method with the following mobile phase gradient: Mobile phase A: 50 mM of sodium perchlorate in a solvent containing 76% water and 24% acetonitrile and 0.1% of trifluoroacetic acid; Mobile phase B: 50 mM of sodium perchlorate in a solvent containing 5% water and 95% acetonitrile and 0.1% of trifluoroacetic acid; Flow rate: 0.6 ml/min; Column: YMC Pro C18, 150 mm×3 mm ID, 3 µm or equivalent; Column temperature: 40° C.; Fluorescence detection: excitation: 274 nm; emission: 303 nm; Injection volume: 100 µl.

2) Analysis of Total Degradants in the Pharmaceutical Composition:

Degradant analysis was performed using an HPLC method employing the following conditions: Mobile phase A: Water:acetonitrile 98:2, with 0.1% (v/v) of trifluoroacetic acid; Mobile phase B: Water:acetonitrile 5:95, with 0.1% (v/v) of trifluoroacetic acid; Flow rate: 0.6 ml/min; Column: YMC Pro C18, 150 mm×3 mm ID, 3 μm or equivalent; Column temperature: 40° C.; UV detection: excitation: 220 nm; Injection volume: 50 μl. The percentage amounts of degradants in the composition were calculated by quantifying the area of all peaks in the HPLC chromatogram to obtain the "total peak area", and dividing the peak area of each degradant by the total peak area.

3) Dissolution Test:

The dissolution performance of the composition was assessed in phosphate buffer, pH 4.5 using USP Apparatus II (Paddle, 50 rpm).

TABLE 1

Linaclotide IR Tablet, 0.15 mg/200 mg

| Components | Weight/tablet (mg) | Theoretical Weight mg/g |
|---|---|---|
| Linaclotide | 0.15 | 0.75 |
| Isomalt | 50 | 250 |
| Leucine | 0.36 | 1.8 |
| Calcium chloride dihydrate | 0.82 | 4.1 |
| PVP K30 LP | 2.2 | 11 |
| Isomalt | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

TABLE 2

Linaclotide IR tablets of different strengths

| Components | Tablet composition (mg/tablet) | | | | | | |
|---|---|---|---|---|---|---|---|
| | 0.05 | 0.75 | 0.15 | 0.14 | 0.3 | 0.6 | 0.9 |
| Linaclotide | 0.05 | 0.75 | 0.15 | 0.14 | 0.3 | 0.6 | 0.9 |
| Isomalt | 17 | 25 | 50 | 46.7 | 100 | 200 | 300 |
| Leucine | 0.12 | 0.18 | 0.36 | 0.34 | 0.72 | 1.44 | 2.16 |
| Calcium chloride | 0.27 | 0.41 | 0.82 | 0.77 | 1.64 | 3.28 | 4.92 |
| PVP K30 LP | 0.7 | 1.1 | 2.2 | 2.05 | 4.4 | 8.8 | 13.2 |
| Isomalt | 44.7 | 67.05 | 134.1 | 137.5 | 268.1 | 536.2 | 804.3 |
| crospovidone | 3.3 | 5 | 10 | 10 | 20 | 40 | 60 |
| Magnesium stearate | 0.5 | 0.75 | 1.5 | 1.5 | 3 | 6 | 9 |
| Talc | 0.3 | 0.5 | 1 | 1 | 2 | 4 | 6 |
| Total | 67 | 100 | 200 | 200 | 800 | 1600 | 2400 |

Example 1

Linaclotide Immediate Release (IR) Tablet 1000 g of HCl solution (0.0001N, pH 4) was weighed in a container and PVP (50% of theoretical weight), linaclotide, calcium chloride, and leucine were added into the HCl solution while mixing, until a clear coating solution was obtained. Isomalt and PVP (50% of theoretical weight) were charged into the bowl of the fluid bed (Glatt GCGP 3.1, Glatt, Ramsey N.J.) and mixed for 2 minutes by fluidizing the powder. The coating solution was top sprayed on the fluidized powder at a speed of 10 g/min and the granules were dried for 20 minutes at a product temperature of 40° C. The granules were discharged and sieved through a 20 mesh hand screen. The linaclotide granules, isomalt, and crospovidone were weighed, screened together through a 20 mesh hand screen, charged into a V-blender shell (available from Patterson-Kelly, East Stroudsburg, Pa.), and mixed for 20 minutes. Talc was weighed and screened through a 20 mesh hand screen, added to the V-blender and mixed for 3 minutes. Magnesium stearate was weighed, screened through a 20 mesh hand screen, added to the V-blender and mixed for 3 minutes. The blend was discharged and added into the hopper of a tablet press. The linaclotide tablets were compressed with a weight of 200 mg and hardness of 4-6 kp. The composition of resulting linaclotide IR tablets of different strengths is shown in Tables 1 and 2.

As is illustrated in Table 3, the stability and dissolution performance of the composition illustrated in Table 1 was assessed.

TABLE 3

Stability and Dissolution Performance of Linaclotide IR Tablet

| Condition | Linaclotide (mcg/tab) | Dissolution % in (pH 4.5) | | | Total Deg % |
|---|---|---|---|---|---|
| | | 15 min | 30 min | 45 min | |
| Initial | 133.4 | 79 | 98 | 98 | 1.96 |
| 40° C./75% RH, 1 month | 135 | 82 | 97 | 98 | 2.74 |
| 40° C. 75% RH, 3 months | 127.8 | 64 | 84 | 85 | 4.19 |
| 40° C./75% RH, 6 months | 124 | 81 | 81 | 81 | 5.48 |

Example 2

Linaclotide IR tablets comprising components as shown in Table 4 were prepared in the same manner as described in Example 1. The dissolution and stability performance of the linaclotide IR tablets (0.135 mg/200 mg, HDPE bottle with desiccant) was evaluated at 40° C./75% RH, as is illustrated in Table 5.

TABLE 4

Linaclotide IR tablet, 0.15 mg/200 mg

| Components | Weight/tablet (mg) | Theoretical Weight mg/g |
|---|---|---|
| Linaclotide | 0.15 | 0.75 |
| Isomalt | 50 | 250 |
| Leucine | 0.36 | 1.8 |
| Calcium chloride dihydrate | 0.82 | 4.1 |
| PVP K30 LP | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

TABLE 5

Stability and Dissolution Performance of Linaclotide IR tablet

| Condition | Total Linaclotide (mcg/tab) | Dissolution % in (pH 4.5) 15 min | 30 min | 45 min | Total Deg % |
|---|---|---|---|---|---|
| Initial | 140.1 | 84.6 | 97 | 97 | 2.35 |
| 40° C./75% RH, 1 month | 141.3 | 93.1 | 95 | 95 | 2.74 |
| 40° C./75% RH, 3 months | 136.1 | 49 | 85 | 87 | 3.54 |

Example 3

Linaclotide IR tablets comprising components as shown in Table 6 were prepared in the manner described in Example 1. The dissolution and stability of linaclotide IR tablets (0.135 mg/200 mg, HDPE bottle with desiccant) was evaluated at 40° C./75% RH, as is illustrated in Table 7.

TABLE 6

Linaclotide IR tablet, 0.15 mg/200 mg

| Components | Weight/tablet (mg) | Theoretical Weight mg/g |
|---|---|---|
| Linaclotide | 0.15 | 0.75 |
| Dicalcium phosphate | 50 | 250 |
| Leucine | 0.36 | 1.8 |
| Calcium chloride dihydrate | 0.82 | 4.1 |
| PVP K30 LP | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

TABLE 7

Stability and Dissolution Performance of Linaclotide IR tablet

| Condition | Total Linaclotide (mcg/tab) | Dissolution % in (pH 4.5) 15 min | 30 min | 45 min | Total Deg % |
|---|---|---|---|---|---|
| Initial | 144.3 | 78 | 89 | 94 | 2.46 |
| 40° C./75, 1 month | 136 | 50 | 81 | 86 | 5.53 |

Example 4

Linaclotide IR tablets comprising components as shown in Table 8 were prepared in the manner described in Example 1. The dissolution and stability of linaclotide IR tablets (0.15 mg/200 mg) was evaluated at 40° C./75% RH, as is illustrated in Table 9.

TABLE 8

Linaclotide IR tablet, 0.15 mg/200 mg

| Components | Weight/tablet (mg) | Theoretical Weight mg/g |
|---|---|---|
| Linaclotide | 0.15 | 0.75 |
| Microcrystalline cellulose | 50 | 250 |
| Leucine | 0.36 | 1.8 |
| Calcium chloride dihydrate | 0.82 | 4.1 |
| PVP K30 LP | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

TABLE 9

Stability and Dissolution Performance of Linaclotide IR tablet

| Condition | Desiccant (g) | Total Linaclotide (mcg/tab) | Dissolution % in (pH 4.5) 15 min | 30 min | 45 min | Total Deg % |
|---|---|---|---|---|---|---|
| Initial | N/A | 145.4 | 80 | 95 | 94 | 2.65 |
| 40° C./75, 1 month | 5 | 132 | 70 | 84 | 85 | 2.56 |
| 40° C./75, 3 months | 5 | 121 | 73 | 86 | 85 | 8.88 |

Example 5

Linaclotide IR tablets comprising components as shown in Table 10 were prepared in the manner described in Example 1. The dissolution and stability of linaclotide IR tablets (0.15 mg/200 mg) was evaluated at 40° C./75% RH, as is illustrated in Table 11.

TABLE 10

Linaclotide IR tablet, 0.15 mg/200 mg

| Components | Weight/tablet (mg) | Theoretical Weight mg/g |
|---|---|---|
| Linaclotide | 0.15 | 0.75 |
| Mannitol | 50 | 250 |
| Leucine | 0.36 | 1.8 |
| Calcium chloride dihydrate | 0.82 | 4.1 |
| PVP K30 LP | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

TABLE 11

Stability and Dissolution Performance of Linaclotide IR tablet

| Condition | Desiccant g | Total Linaclotide (mcg/tab) | Dissolution % in (pH 4.5) 15 min | 30 min | 45 min | Total Deg % |
|---|---|---|---|---|---|---|
| Initial | N/A | 146.5 | 84 | 96 | 98 | 1.66 |

Example 6

Linaclotide IR capsules comprising components as shown in Table 12 were prepared using a process similar to that described in Example 1 but without use of the tablet press.

TABLE 12

Linaclotide beads (600 mcg/225 mg)

| COMPONENTS | % W/W | QUANTITY/UNIT (mg) |
|---|---|---|
| Linaclotide | 0.267 | 0.600 |
| HPMC (Methocel E5 Premium LV) | 0.7 | 1.575 |
| Calcium Chloride Dihydrate | 1.54 | 3.47 |
| Leucine | 0.68 | 1.54 |
| Microcrystalline Cellulose, NF (Celphere CP305 beads) | 96.8 | 217.8 |
| Hydrochloric acid, NF (36.5-38%) | — | — |
| Purified water, USP | — | — |
| TOTAL | 100.0 | 225.0 |

The stability and dissolution of the linaclotide IR capsules (35 cap in 45 cc bottle, w/2 g desiccant) were evaluated at 40° C./75% RH, as is illustrated in Table 13.

TABLE 13

Stability of linaclotide capsule (150 mcg)

| Capsule | Condition | Assay | Total Deg % | Dissolution % 15 min | 30 min |
|---|---|---|---|---|---|
| 150 mcg, beads in size 2 gelatin capsule | Initial | 100.4 | 1.77 | 86 | 94 |
| | 40/75, 1 month | 97.4 | 1.77 | | |
| | 40/75, 2 month | 97.8 | 2.79 | 90 | 94 |
| | 40/75, 3 month | 98 | 3.46 | | |
| | 40/75, 6 month | 92.3 | 7.98 | 71 | 78 |

Example 7

Linaclotide IR tablets comprising components as shown in Table 14 were prepared as described in Example 1.

TABLE 14

Linaclotide IR tablet, 0.15 mg/200 mg

| Ingredients | Weight/tablet (mg) | Theoretical Weight mg/g |
|---|---|---|
| Linaclotide | 0.15 | 0.75 |
| Isomalt | 50 | 250 |
| Leucine | 0.36 | 1.8 |
| Calcium chloride dihydrate | 0.82 | 4.1 |
| PVP K30 LP | 2.2 | 11 |
| Isomalt | 134.1 | 670.5 |
| Croscarmellose sodium | 10 | 50 |
| Magnesium stearate | 1.5 | 7.5 |
| Talc | 1 | 5 |
| 0.0001N HCl* | — | 1100* |
| Total dry weight | 200.13 | 1000.7 |

The stability and dissolution of the linaclotide IR tablets were evaluated at 40° C./75% RH, as is illustrated in Table 15.

TABLE 15

150 mcg tablet, 35 tab in 60 cc bottle, w/5 g desiccant, with croscarmellose sodium as disintegrant

| Time | Assay* | Assay of initial % | Total Deg | Dissolution (normalized) 15' | 30' | 45' |
|---|---|---|---|---|---|---|
| initial | 77.2 | 100 | 2.27 | 100 | 100 | 100 |
| 40/75, 1 m | 74.3 | 96.2 | 2.09 | | | |
| 40/75, 2 m | 78.8 | 102 | 2.15 | | | |
| 40/75, 3 m | 76.8 | 99.5 | 1.52 | 90 | 90 | 93 |
| 30/65, 3 m | 77.3 | 100.1 | 1.19 | | | |

Example 8

Linaclotide IR capsules comprising components as shown in Table 16 may be prepared using a process similar to that described in Example 6.

TABLE 16

| Components | Wt. in gms | Wt % |
|---|---|---|
| linaclotide | 2.94 | 0.3 |
| Isomalt | 909 | 90.9 |
| Leucine | 22.9 | 2.29 |
| Calcium chloride dihydrate | 25.7 | 2.57 |
| PVP | 40 | 4 |
| 0.0001N HCl | 1000* | |
| Gelatin capsule | 18,000 | |
| TOTAL | 999.94 | 100.0 |

*water is removed during the manufacturing process

Example 9

Linaclotide IR capsules comprising components as shown in Table 17 may be prepared using a process similar to that described in Example 6.

TABLE 17

| Components | Wt. in gms | Wt % |
|---|---|---|
| linaclotide | 8.8 | 0.3 |
| Isomalt | 2805 | 93.5 |
| Leucine | 20.6 | 0.69 |
| Calcium chloride dihydrate | 46.2 | 1.54 |
| PVP | 120 | 4 |
| 0.0001N HCl | 1000* | |
| Gelatin capsule | 18,000 | |
| TOTAL | 3000.6 | 100.03 |

*water is removed during the manufacturing process

Example 10

Linaclotide IR capsules comprising components as shown in Table 18 may be prepared using a process similar to that described in Example 6.

TABLE 18

| Components | Wt. in gms | Wt % |
|---|---|---|
| linaclotide | 2.94 | 0.3 |
| Mannitol | 933 | 93.3 |
| Leucine | 11.5 | 1.15 |
| Calcium chloride dihydrate | 12.9 | 1.29 |
| PVP | 40 | 4 |
| 0.0001N HCl | 1000* | |
| Gelatin capsule | 18,000 | |
| TOTAL | 1000.34 | 100.0 |

*water is removed during the manufacturing process

Example 11

Linaclotide IR tablets comprising components as shown in Table 19 may be prepared as described in Example 1.

TABLE 19

Linaclotide IR tablet, 0.15 mg/200 mg

| Components | Weight/tablet (mg) | Theoretical Weight mg/g |
|---|---|---|
| Linaclotide | 0.15 | 0.75 |
| isomalt | 50 | 250 |
| Leucine | 0.36 | 1.8 |
| Calcium chloride | 0.82 | 4.1 |
| PVA | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 12

Linaclotide IR tablets comprising components as shown in Table 20 may be prepared as described in Example 1 using pregelatinized starch as a granular filling agent.

TABLE 20

Linaclotide IR tablet, 0.15 mg/200 mg

| Components | Weight/tablet (mg) | Theoretical Weight mg/g |
|---|---|---|
| Linaclotide | 0.15 | 0.75 |
| Pregelatinized starch | 50 | 250 |
| Leucine | 0.36 | 1.8 |
| Calcium chloride dihydrate | 0.82 | 4.1 |
| PVP K30 LP | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 13

Linaclotide IR tablets comprising components as shown in Table 21 may be prepared as described in Example 1 using trehalose as a granular filling agent.

TABLE 21

Linaclotide IR tablet, 0.15 mg/200 mg

| Components | Weight/tablet (mg) | Theoretical Weight mg/g |
|---|---|---|
| Linaclotide | 0.15 | 0.75 |
| Trehalose | 50 | 250 |
| Leucine | 0.36 | 1.8 |
| Calcium chloride dihydrate | 0.82 | 4.1 |
| PVP K30 LP | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 14

Linaclotide IR tablets comprising components as shown in Table 22 may be prepared as described in Example 1 using erythitol as a granular filling agent.

TABLE 22

Linaclotide IR tablet, 0.15 mg/200 mg

| Components | Weight/tablet (mg) | Theoretical Weight mg/g |
|---|---|---|
| Linaclotide | 0.15 | 0.75 |
| Erythitol | 50 | 250 |
| Leucine | 0.36 | 1.8 |
| Calcium chloride dihydrate | 0.82 | 4.1 |
| PVP K30 LP | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 15

Linaclotide IR tablets comprising components as shown in Table 23 may be prepared as described in Example 1 using maltitol as a granular filling agent.

TABLE 23

| Linaclotide IR tablet, 0.15 mg/200 mg | | |
|---|---|---|
| Components | Weight/tablet (mg) | Theoretical Weight mg/g |
| Linaclotide | 0.15 | 0.75 |
| Maltitol | 50 | 250 |
| Leucine | 0.36 | 1.8 |
| Calcium chloride dihydrate | 0.82 | 4.1 |
| PVP K30 LP | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 16

Linaclotide IR tablets comprising components as shown in Table 24 may be prepared as described in Example 1 using lactose as a granular filling agent.

TABLE 24

| Linaclotide IR tablet, 0.15 mg/200 mg | | |
|---|---|---|
| Components | Weight/tablet (mg) | Theoretical Weight mg/g |
| Linaclotide | 0.15 | 0.75 |
| Lactose | 50 | 250 |
| Leucine | 0.36 | 1.8 |
| Calcium chloride dihydrate | 0.82 | 4.1 |
| PVP K30 LP | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 17

Linaclotide IR tablets comprising components as shown in Table 25 may be prepared as described in Example 1 using glucose as a granular filling agent.

TABLE 25

| Linaclotide IR tablet, 0.15 mg/200 mg | | |
|---|---|---|
| Components | Weight/tablet (mg) | Theoretical Weight mg/g |
| Linaclotide | 0.15 | 0.75 |
| Glucose | 50 | 250 |
| Leucine | 0.36 | 1.8 |
| Calcium chloride dihydrate | 0.82 | 4.1 |
| PVP K30 LP | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 18

Linaclotide IR tablets comprising components as shown in Table 26 may be prepared as described in Example 1 using isoleucine as a stabilizing agent.

TABLE 26

| Linaclotide IR tablet, 0.15 mg/200 mg | | |
|---|---|---|
| Components | Weight/tablet (mg) | Theoretical Weight mg/g |
| Linaclotide | 0.15 | 0.75 |
| isomalt | 50 | 250 |
| Isoleucine | 0.36 | 1.8 |
| Calcium chloride dihydrate | 0.82 | 4.1 |
| PVP K30 LP | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 19

Linaclotide IR tablets comprising components as shown in Table 27 may be prepared as described in Example 1 using asparagine as a stabilizing agent.

TABLE 27

| Linaclotide IR tablet, 0.15 mg/200 mg | | |
|---|---|---|
| Components | Weight/tablet (mg) | Theoretical Weight mg/g |
| Linaclotide | 0.15 | 0.75 |
| isomalt | 50 | 250 |
| Asparagine | 0.36 | 1.8 |
| Calcium chloride dihydrate | 0.82 | 4.1 |
| PVP K30 LP | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 20

Linaclotide IR tablets comprising components as shown in Table 28 may be prepared as described in Example 1 using glutamine as a stabilizing agent.

TABLE 28

Linaclotide IR tablet, 0.15 mg/200 mg

| Components | Weight/tablet (mg) | Theoretical Weight mg/g |
|---|---|---|
| Linaclotide | 0.15 | 0.75 |
| isomalt | 50 | 250 |
| Glutamine | 0.36 | 1.8 |
| Calcium chloride dihydrate | 0.82 | 4.1 |
| PVP K30 LP | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 21

Linaclotide IR tablets comprising components as shown in Table 29 may be prepared as described in Example 1 using glutamic acid as a stabilizing agent.

TABLE 29

Linaclotide IR tablet, 0.15 mg/200 mg

| Components | Weight/tablet (mg) | Theoretical Weight mg/g |
|---|---|---|
| Linaclotide | 0.15 | 0.75 |
| isomalt | 50 | 250 |
| Glutamic acid | 0.36 | 1.8 |
| Calcium chloride dihydrate | 0.82 | 4.1 |
| PVP K30 LP | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 22

Linaclotide IR tablets comprising components as shown in Table 30 may be prepared as described in Example 1 using histidine as a stabilizing agent.

TABLE 30

Linaclotide IR tablet, 0.15 mg/200 mg

| Components | Weight/tablet (mg) | Theoretical Weight mg/g |
|---|---|---|
| Linaclotide | 0.15 | 0.75 |
| isomalt | 50 | 250 |
| Histidine | 0.36 | 1.8 |
| Calcium chloride dihydrate | 0.82 | 4.1 |
| PVP K30 LP | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 23

Linaclotide IR tablets comprising components as shown in Table 31 may be prepared as described in Example 1 using glycine as a stabilizing agent.

TABLE 31

Linaclotide IR tablet, 0.15 mg/200 mg

| Components | Weight/tablet (mg) | Theoretical Weight mg/g |
|---|---|---|
| Linaclotide | 0.15 | 0.75 |
| isomalt | 50 | 250 |
| Glycine | 0.36 | 1.8 |
| Calcium chloride dihydrate | 0.82 | 4.1 |
| PVP K30 LP | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 24

Linaclotide IR tablets comprising components as shown in Table 32 may be prepared as described in Example 1 using cysteine as a stabilizing agent.

TABLE 32

Linaclotide IR tablet, 0.15 mg/200 mg

| Components | Weight/tablet (mg) | Theoretical Weight mg/g |
|---|---|---|
| Linaclotide | 0.15 | 0.75 |
| isomalt | 50 | 250 |
| Cysteine | 0.36 | 1.8 |
| Calcium chloride dihydrate | 0.82 | 4.1 |
| PVP K30 LP | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 25

Linaclotide IR tablets comprising components as shown in Table 33 may be prepared as described in Example 1 using alanine as a stabilizing agent.

TABLE 33

Linaclotide IR tablet, 0.15 mg/200 mg

| Components | Weight/tablet (mg) | Theoretical Weight mg/g |
|---|---|---|
| Linaclotide | 0.15 | 0.75 |
| isomalt | 50 | 250 |
| Alanine | 0.36 | 1.8 |
| Calcium chloride dihydrate | 0.82 | 4.1 |
| PVP K30 LP | 2.2 | 11 |
| Pregelatinized starch | 134.1 | 670.5 |

TABLE 33-continued

Linaclotide IR tablet, 0.15 mg/200 mg

| Components | Weight/tablet (mg) | Theoretical Weight mg/g |
|---|---|---|
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 26

Linaclotide IR tablets comprising components as shown in Table 34 may be prepared as described in Example 1 using serine as a stabilizing agent.

TABLE 34

Linaclotide IR tablet, 0.15 mg/200 mg

| Components | Weight/tablet (mg) | Theoretical Weight mg/g |
|---|---|---|
| Linaclotide | 0.15 | 0.75 |
| isomalt | 50 | 250 |
| Serine | 0.36 | 1.8 |
| Calcium chloride dihydrate | 0.82 | 4.1 |
| PVP K30 LP | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 27

Linaclotide IR tablets comprising components as shown in Table 35 may be prepared as described in Example 1 using threonine as a stabilizing agent.

TABLE 35

Linaclotide IR tablet, 0.15 mg/200 mg

| Components | Weight/tablet (mg) | Theoretical Weight mg/g |
|---|---|---|
| Linaclotide | 0.15 | 0.75 |
| isomalt | 50 | 250 |
| Threonine | 0.36 | 1.8 |
| Calcium chloride dihydrate | 0.82 | 4.1 |
| PVP K30 LP | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 28

Linaclotide IR tablets comprising components as shown in Table 36 may be prepared as described in Example 1 using tyrosine as a stabilizing agent.

TABLE 36

Linaclotide IR tablet, 0.15 mg/200 mg

| Components | Weight/tablet (mg) | Theoretical Weight mg/g |
|---|---|---|
| Linaclotide | 0.15 | 0.75 |
| isomalt | 50 | 250 |
| Tyrosine | 0.36 | 1.8 |
| Calcium chloride dihydrate | 0.82 | 4.1 |
| PVP K30 LP | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 29

Linaclotide IR tablets comprising components as shown in Table 37 may be prepared as described in Example 1 using proline as a stabilizing agent.

TABLE 37

Linaclotide IR tablet, 0.15 mg/200 mg

| Components | Weight/tablet (mg) | Theoretical Weight mg/g |
|---|---|---|
| Linaclotide | 0.15 | 0.75 |
| isomalt | 50 | 250 |
| Proline | 0.36 | 1.8 |
| Calcium chloride dihydrate | 0.82 | 4.1 |
| PVP K30 LP | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 30

Linaclotide IR tablets comprising components as shown in Table 38 may be prepared as described in Example 1 using tryptophan as a stabilizing agent.

TABLE 38

Linaclotide IR tablet, 0.15 mg/200 mg

| Components | Weight/tablet (mg) | Theoretical Weight mg/g |
|---|---|---|
| Linaclotide | 0.15 | 0.75 |
| isomalt | 50 | 250 |
| Tryptophan | 0.36 | 1.8 |
| Calcium chloride dihydrate | 0.82 | 4.1 |
| PVP K30 LP | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 31

Linaclotide IR tablets comprising components as shown in Table 39 may be prepared as described in Example 1 using KCl as a stabilizing agent.

TABLE 39

Linaclotide IR tablet, 0.15 mg/200 mg

| Components | Weight/tablet (mg) | Theoretical Weight mg/g |
|---|---|---|
| Linaclotide | 0.15 | 0.75 |
| isomalt | 50 | 250 |
| Leucine | 0.36 | 1.8 |
| Potassium chloride | 0.82 | 4.1 |
| PVP K30 LP | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 32

Linaclotide IR tablets comprising components as shown in Table 40 may be prepared as described in Example 1 using NaCl as a stabilizing agent.

TABLE 40

Linaclotide IR tablet, 0.15 mg/200 mg

| Components | Weight/tablet (mg) | Theoretical Weight mg/g |
|---|---|---|
| Linaclotide | 0.15 | 0.75 |
| isomalt | 50 | 250 |
| Leucine | 0.36 | 1.8 |
| Sodium chloride | 0.82 | 4.1 |
| PVP K30 LP | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 33

Linaclotide IR tablets comprising components as shown in Table 41 may be prepared as described in Example 1 using $MgCl_2$ as a stabilizing agent.

TABLE 41

Linaclotide IR tablet, 0.15 mg/200 mg

| Components | Weight/tablet (mg) | Theoretical Weight mg/g |
|---|---|---|
| Linaclotide | 0.15 | 0.75 |
| isomalt | 50 | 250 |
| Leucine | 0.36 | 1.8 |
| Magnesium chloride | 0.82 | 4.1 |
| PVP K30 LP | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 34

Linaclotide IR tablets comprising components as shown in Table 42 may be prepared as described in Example 1 using $ZnCl_2$ as a stabilizing agent.

TABLE 42

Linaclotide IR tablet, 0.15 mg/200 mg

| Components | Weight/tablet (mg) | Theoretical Weight mg/g |
|---|---|---|
| Linaclotide | 0.15 | 0.75 |
| isomalt | 50 | 250 |
| Leucine | 0.36 | 1.8 |
| Zinc chloride | 0.82 | 4.1 |
| PVP K30 LP | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 35

Linaclotide IR tablets comprising components as shown in Table 43 may be prepared as described in Example 1 using $BaCl_2$ as a stabilizing agent.

TABLE 43

Linaclotide IR tablet, 0.15 mg/200 mg

| Components | Weight/tablet (mg) | Theoretical Weight mg/g |
|---|---|---|
| Linaclotide | 0.15 | 0.75 |
| isomalt | 50 | 250 |
| Leucine | 0.36 | 1.8 |
| Barium chloride | 0.82 | 4.1 |
| PVP K30 LP | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 36

Linaclotide IR tablets comprising components as shown in Table 44 may be prepared as described in Example 1 using $MnCl_2$ as a stabilizing agent.

TABLE 44

Linaclotide IR tablet, 0.15 mg/200 mg

| Components | Weight/tablet (mg) | Theoretical Weight mg/g |
|---|---|---|
| Linaclotide | 0.15 | 0.75 |
| isomalt | 50 | 250 |
| Leucine | 0.36 | 1.8 |
| Manganese chloride | 0.82 | 4.1 |
| PVP K30 LP | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 37

Linaclotide IR tablets comprising components as shown in Table 45 may be prepared as described in Example 1 using a polaxomer as a stabilizing agent.

TABLE 45

Linaclotide IR tablet, 0.15 mg/200 mg

| Components | Weight/tablet (mg) | Theoretical Weight mg/g |
|---|---|---|
| Linaclotide | 0.15 | 0.75 |
| isomalt | 50 | 250 |
| Leucine | 0.36 | 1.8 |
| Calcium chloride | 0.82 | 4.1 |
| Poloxamer (Pluronic ®) | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 38

Linaclotide IR tablets comprising components as shown in Table 46 may be prepared as described in Example 1 using gelatin as a stabilizing agent.

TABLE 46

Linaclotide IR tablet, 0.15 mg/200 mg

| Components | Weight/tablet (mg) | Theoretical Weight mg/g |
|---|---|---|
| Linaclotide | 0.15 | 0.75 |
| isomalt | 50 | 250 |
| Leucine | 0.36 | 1.8 |
| Calcium chloride | 0.82 | 4.1 |
| Gelatin | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 39

Linaclotide IR tablets comprising components as shown in Table 47 may be prepared as described in Example 1 using chitosan as a stabilizing agent.

TABLE 47

Linaclotide IR tablet, 0.15 mg/200 mg

| Components | Weight/tablet (mg) | Theoretical Weight mg/g |
|---|---|---|
| Linaclotide | 0.15 | 0.75 |
| isomalt | 50 | 250 |
| Leucine | 0.36 | 1.8 |
| Calcium chloride | 0.82 | 4.1 |
| Chitosan | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 40

Linaclotide IR tablets comprising components as shown in Table 48 may be prepared as described in Example 1 using cyclodextran as a stabilizing agent.

TABLE 48

Linaclotide IR tablet, 0.15 mg/200 mg

| Components | Weight/tablet (mg) | Theoretical Weight mg/g |
|---|---|---|
| Linaclotide | 0.15 | 0.75 |
| isomalt | 50 | 250 |
| Leucine | 0.36 | 1.8 |
| Calcium chloride | 0.82 | 4.1 |
| Cyclodextrin | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 41

Linaclotide IR tablets comprising components as shown in Table 49 may be prepared as described in Example 1 using guar gum as a stabilizing agent.

TABLE 49

Linaclotide IR tablet, 0.15 mg/200 mg

| Components | Weight/tablet (mg) | Theoretical Weight mg/g |
|---|---|---|
| Linaclotide | 0.15 | 0.75 |
| isomalt | 50 | 250 |
| Leucine | 0.36 | 1.8 |
| Calcium chloride | 0.82 | 4.1 |
| Guar gum | 2.2 | 11 |
| Pregelatinized starch | 134.1 | 670.5 |

TABLE 49-continued

Linaclotide IR tablet, 0.15 mg/200 mg

| Components | Weight/tablet (mg) | Theoretical Weight mg/g |
|---|---|---|
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 42

Linaclotide IR tablets comprising components as shown in Table 50 may be prepared as described in Example 1 using xanthan gum as a stabilizing agent.

TABLE 50

Linaclotide IR tablet, 0.15 mg/200 mg

| Components | Weight/tablet (mg) | Theoretical Weight mg/g |
|---|---|---|
| Linaclotide | 0.15 | 0.75 |
| isomalt | 50 | 250 |
| Leucine | 0.36 | 1.8 |
| Calcium chloride | 0.82 | 4.1 |
| Xanthan gum | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 43

Linaclotide IR tablets comprising components as shown in Table 51 may be prepared as described in Example 1 using dextran as a stabilizing agent.

TABLE 51

Linaclotide IR tablet, 0.15 mg/200 mg

| Components | Weight/tablet (mg) | Theoretical Weight mg/g |
|---|---|---|
| Linaclotide | 0.15 | 0.75 |
| isomalt | 50 | 250 |
| Leucine | 0.36 | 1.8 |
| Calcium chloride | 0.82 | 4.1 |
| Dextran | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 44

Linaclotide IR tablets comprising components as shown in Table 52 may be prepared as described in Example 1 using dextrin as a stabilizing agent.

TABLE 52

Linaclotide IR tablet, 0.15 mg/200 mg

| Components | Weight/tablet (mg) | Theoretical Weight mg/g |
|---|---|---|
| Linaclotide | 0.15 | 0.75 |
| isomalt | 50 | 250 |
| Leucine | 0.36 | 1.8 |
| Calcium chloride | 0.82 | 4.1 |
| Dextrin | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 45

Linaclotide IR tablets comprising components as shown in Table 53 may be prepared as described in Example 1 using polyethylene polypropylene oxide as a stabilizing agent.

TABLE 53

Linaclotide IR tablet, 0.15 mg/200 mg

| Components | Weight/tablet (mg) | Theoretical Weight mg/g |
|---|---|---|
| Linaclotide | 0.15 | 0.75 |
| isomalt | 50 | 250 |
| Leucine | 0.36 | 1.8 |
| Calcium chloride | 0.82 | 4.1 |
| Polyethylene polypropylene oxide | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 46

Linaclotide IR tablets comprising components as shown in Table 54 may be prepared as described in Example 1 using polyacrylic acid as a stabilizing agent.

TABLE 54

Linaclotide IR tablet, 0.15 mg/200 mg

| Components | Weight/tablet (mg) | Theoretical Weight mg/g |
|---|---|---|
| Linaclotide | 0.15 | 0.75 |
| isomalt | 50 | 250 |
| Leucine | 0.36 | 1.8 |
| Calcium chloride | 0.82 | 4.1 |
| Polyacrylic acid | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 47

Linaclotide IR tablets comprising components as shown in Table 55 may be prepared as described in Example 1 using hydroxylpropyl cellulose as a stabilizing agent.

TABLE 55

Linaclotide IR tablet, 0.15 mg/200 mg

| Components | Weight/tablet (mg) | Theoretical Weight mg/g |
|---|---|---|
| Linaclotide | 0.15 | 0.75 |
| isomalt | 50 | 250 |
| Leucine | 0.36 | 1.8 |
| Calcium chloride | 0.82 | 4.1 |
| Hydroxylpropyl cellulose | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 48

Linaclotide IR tablets comprising components as shown in Table 56 may be prepared as described in Example 1 using methyl cellulose as a stabilizing agent.

TABLE 56

Linaclotide IR tablet, 0.15 mg/200 mg

| Components | Weight/tablet (mg) | Theoretical Weight mg/g |
|---|---|---|
| Linaclotide | 0.15 | 0.75 |
| isomalt | 50 | 250 |
| Leucine | 0.36 | 1.8 |
| Calcium chloride | 0.82 | 4.1 |
| Methyl cellulose | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 49

Linaclotide IR tablets comprising components as shown in Table 57 may be prepared as described in Example 1 using hydroxylpropyl methylcellulose as a stabilizing agent.

TABLE 57

Linaclotide IR tablet, 0.15 mg/200 mg

| Components | Weight/tablet (mg) | Theoretical Weight mg/g |
|---|---|---|
| Linaclotide | 0.15 | 0.75 |
| isomalt | 50 | 250 |
| Leucine | 0.36 | 1.8 |
| Calcium chloride | 0.82 | 4.1 |
| Hydroxylpropyl methylcellulose | 2.2 | 11 |
| Pregelatinized starch | 134.1 | 670.5 |

TABLE 57-continued

Linaclotide IR tablet, 0.15 mg/200 mg

| Components | Weight/tablet (mg) | Theoretical Weight mg/g |
|---|---|---|
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 50

Linaclotide IR tablets comprising components as shown in Table 58 may be prepared as described in Example 1 using Poly(sodium vinylsulfonate) as a stabilizing agent.

TABLE 58

Linaclotide IR tablet, 0.15 mg/200 mg

| Components | Weight/tablet (mg) | Theoretical Weight mg/g |
|---|---|---|
| Linaclotide | 0.15 | 0.75 |
| isomalt | 50 | 250 |
| Leucine | 0.36 | 1.8 |
| Calcium chloride | 0.82 | 4.1 |
| Poly(sodium vinylsulfonate) | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 51

Linaclotide IR tablets comprising components as shown in Table 59 may be prepared as described in Example 1 using polyethylene glycol as a stabilizing agent.

TABLE 59

Linaclotide IR tablet, 0.15 mg/200 mg

| Components | Weight/tablet (mg) | Theoretical Weight mg/g |
|---|---|---|
| Linaclotide | 0.15 | 0.75 |
| isomalt | 50 | 250 |
| Leucine | 0.36 | 1.8 |
| Calcium chloride | 0.82 | 4.1 |
| Polyethylene glycol | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 52

Linaclotide IR tablets comprising components as shown in Table 60 may be prepared as described in Example 1 using poly(arginine) as a stabilizing agent.

TABLE 60

Linaclotide IR tablet, 0.15 mg/200 mg

| Components | Weight/tablet (mg) | Theoretical Weight mg/g |
|---|---|---|
| Linaclotide | 0.15 | 0.75 |
| isomalt | 50 | 250 |
| Leucine | 0.36 | 1.8 |
| Calcium chloride | 0.82 | 4.1 |
| Poly(arginine) | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 53

Linaclotide IR tablets comprising components as shown in Table 61 may be prepared as described in Example 1 using polycarbophil as a stabilizing agent.

TABLE 61

Linaclotide IR tablet, 0.15 mg/200 mg

| Components | Weight/tablet (mg) | Theoretical Weight mg/g |
|---|---|---|
| Linaclotide | 0.15 | 0.75 |
| isomalt | 50 | 250 |
| Leucine | 0.36 | 1.8 |
| Calcium chloride | 0.82 | 4.1 |
| Polycarbophil | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 54

Linaclotide IR tablets comprising components as shown in Table 62 may be prepared as described in Example 1 using polyvinyl pyrrolidone-co vinyl acetate as a stabilizing agent.

TABLE 62

Linaclotide IR tablet, 0.15 mg/200 mg

| Components | Weight/tablet (mg) | Theoretical Weight mg/g |
|---|---|---|
| Linaclotide | 0.15 | 0.75 |
| isomalt | 50 | 250 |
| Leucine | 0.36 | 1.8 |
| Calcium chloride | 0.82 | 4.1 |
| polyvinyl pyrrolidone-co vinyl acetate | 2.2 | 11 |
| Pregelatinized starch | 134.1 | 670.5 |
| Crospovidone | 10 | 50 |
| Magnesium stearate | 1.5 | 7.5 |
| Talc | 1 | 5 |
| 0.0001N HCl* | — | 1100* |
| Total dry weight | 200.13 | 1000.7 |

*Water is removed during the manufacturing process.

Example 55

Isolation and Preparation of Linaclotide Hydrolysis Product

The linaclotide hydrolysis product occurs as a transformation of Asn in the 7 position to Asp (the numbering of linaclotide starts with 1 at the N-terminal Cys). Its structure is depicted below:

(SEQ ID NO: 2)

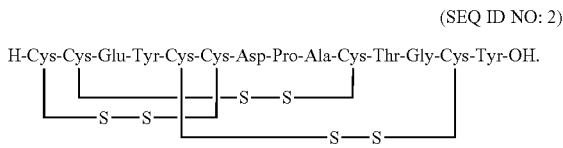

H-Cys-Cys-Glu-Tyr-Cys-Cys-Asp-Pro-Ala-Cys-Thr-Gly-Cys-Tyr-OH.

The linaclotide hydrolysis product has been independently synthesized for confirmation of identity using standard solid phase peptide synthesis techniques. The linaclotide hydrolysis product may also be prepared by other methods known in the art, e.g., by isolation from linaclotide preparations using chromatographic techniques or by recombinant expression of a nucleic acid encoding the linaclotide hydrolysis product (Cys Cys Glu Tyr Cys Cys Asp Pro Ala Cys Thr Gly Cys Tyr (SEQ ID NO: 2)), optionally followed by oxidation of the cysteine residues to form the disulfide linkages.

Example 56

Isolation and Preparation of Linaclotide Formaldehyde Imine Product

The formaldehyde imine product occurs as the addition of an imine to the N-terminal Cys ($Cys_1$) via a formaldehyde-mediated reaction. A proposed structure of the product is depicted below:

(SEQ ID NO: 3)

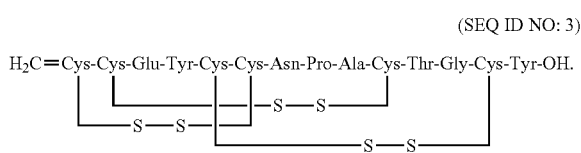

$H_2C$=Cys-Cys-Glu-Tyr-Cys-Cys-Asn-Pro-Ala-Cys-Thr-Gly-Cys-Tyr-OH.

The linaclotide formaldehyde imine product has been independently synthesized for confirmation of identity by reacting linaclotide with formaldehyde (1:5 molar ratio) in absolute ethanol at room temperature for 4 days. The formaldehyde imine product may also be prepared by other methods known in the art, e.g., by isolation from linaclotide preparations using chromatographic techniques or by chemical peptide synthesis or recombinant expression of a nucleic acid encoding linaclotide followed by formylation as described herein or by other methods known in the art, optionally followed by oxidation of the cysteine residues to form the disulfide linkages.

Example 57

Isolation and Preparation of Linaclotide Oxidation Product

The linaclotide oxidation product has a molecular weight of 1542.8. The oxidation product most likely forms as the addition of a single oxygen atom to one of the six cysteinyl sulfurs in linaclotide. One potential structure of the product is depicted below, although one of skill in the art will recognize that the oxygen atom may be attached to any of the other five sulfurs:

(SEQ ID NO: 4)

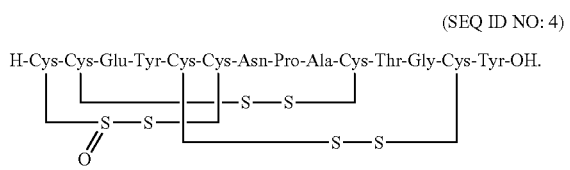

The linaclotide oxidation product has been produced by reacting linaclotide with hydrogen peroxide (3% aqueous) at room temperature or 40° C. for up to 24 hours. The resulting product is enriched in the oxidation product by 1-10%. The linaclotide oxidation product may also be prepared by other methods known in the art, e.g., by isolation from linaclotide preparations using chromatographic techniques or by chemical peptide synthesis or recombinant expression of a nucleic acid encoding linaclotide followed by oxidation of the cysteine residues to form the disulfide linkages followed by reacting linaclotide with hydrogen peroxide or similar oxidizing reagent to form the linaclotide oxidation product.

Example 58

Compositions may be prepared which have the molar ratios of stabilizing agent(s) to linaclotide set forth in Table 63.

TABLE 63

Molar Ratio of Stabilizers to Linaclotide

| Components | Molar ratio* 20 mg/g | Molar ratio 40 mg/g | Molar ratio 60 mg/g | Molar ratio 60 mg/g | Molar ratio 60 mg/g |
|---|---|---|---|---|---|
| Linaclotide | 0.75 | 0.75 | 0.75 | 0.75 | 0.75 |
| Leucine | 1.3 | 2.6 | 3.9 | 5.1 | 6.4 |
| Calcium chloride dihydrate | 1.4 | 2.9 | 4.3 | 5.8 | 7.2 |
| PVP K30 LP | 11 | 11 | 11 | 11 | 11 |
| Isomalt | 253.2 | 250.4 | 247.7 | 245 | 242.3 |
| Isomalt | 670.5 | 670.5 | 670.5 | 670.5 | 670.5 |
| Crospovidone | 50 | 50 | 50 | 50 | 50 |
| Magnesium stearate | 7.5 | 7.5 | 7.5 | 7.5 | 7.5 |
| Talc | 5 | 5 | 5 | 5 | 5 |
| 0.0001N HCl** | 1100* | 1100* | 1100* | 1100* | 1100* |
| Total dry weight | 1000.7 | 1000.7 | 1000.7 | 1000.7 | 1000.7 |

*Molar ratio 20 means molar ratio or CaCl2 to linaclotide is 20, and molar ratio of leucine to linaclotide is 20.
**Water is removed during the manufacturing process.

Example 59

Compositions may be prepared which have the molar ratios of filling agent(s) to linaclotide set forth in Table 64.

TABLE 64

Linaclotide tablet with different level of tablet filling agent

| Components | 20% filling agent mg/g | 40% filling agent mg/g | 60% filling agent mg/g | 80% filling agent mg/g | 90% filling agent mg/g |
|---|---|---|---|---|---|
| Linaclotide | 0.15 | 0.15 | 0.15 | 0.15 | 0.15 |
| Isomalt | 50 | 50 | 50 | 50 | 50 |

TABLE 64-continued

Linaclotide tablet with different level of tablet filling agent

| Components | 20% filling agent mg/g | 40% filling agent mg/g | 60% filling agent mg/g | 80% filling agent mg/g | 90% filling agent mg/g |
|---|---|---|---|---|---|
| Leucine | 0.36 | 0.36 | 0.36 | 0.36 | 0.36 |
| Calcium chloride dihydrate | 0.82 | 0.82 | 0.82 | 0.82 | 0.82 |
| PVP K30 LP | 2.2 | 2.2 | 2.2 | 2.2 | 2.2 |
| Isomalt | 14.5 | 38.8 | 90.1 | 233.5 | 700 |
| Crospovidone | 3.35 | 4 | 5 | 5.3 | 22.7 |
| Magnesium stearate | 0.5 | 0.6 | 0.7 | 0.8 | 3.4 |
| Talc | 0.3 | 0.4 | 0.5 | 0.5 | 2.3 |
| 0.0001N HCl* | — | — | — | — | — |
| Total tablet weight | 72.2 | 97.3 | 149.5 | 293.1 | 782 |

*Water is removed during the manufacturing process.

Example 60

Linaclotide Immediate Release (IR) Tablet for Pediatric Application 1000 g of HCl solution (0.0001N, pH 4) was weighed in a container and polyvinyl pyrrolidone (PVP) (50% of theoretical weight), linaclotide, calcium chloride, and leucine were added into the HCl solution while mixing, until a clear coating solution was obtained. Isomalt and PVP (50% of theoretical weight) were charged into the bowl of the fluid bed (Glatt GCGP 3.0, Glatt, Ramsey N.J.) and mixed for 2 min by fluidizing the powder. The coating solution was top sprayed on the fluidized powder at a speed of 10 g/min and the granules were dried for 20 min at a product temperature of 40° C. The granules were discharged and sieved through a 20 mesh hand screen. The linaclotide granules, isomalt, and croscarmellose sodium were weighed, screened together through a 20 mesh hand screen, charged into a V-blender shell (Patterson-Kelly, East Stroudsburg, Pa.) and mixed for 20 min. Talc was weighed and screened through a 20 mesh hand screen, added to the V-blender and mixed for 3 min. Magnesium stearate was weighed, screened through a 20 mesh hand screen, added to the V-blender and mixed for 3 min. The blend was discharged and added into the hopper of a tablet press.

The linaclotide tablets were compressed with a weight of 75 mg and hardness of 4-6 kp. The composition of resulting linaclotide IR tablets of different strengths is shown in Tables 65 and 66.

TABLE 65

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Isomalt (powder) | 48 | 640 |
| Leucine | 0.001 | 0.013 |
| Calcium chloride dihydrate | 0.003 | 0.04 |

TABLE 65-continued

Linaclotide IR tablet, 0.0005 mg/75 mg

| Ingredients | Weight/tablet (mg) | Theoretical Weight mg/g |
|---|---|---|
| PVP K30 LP | 2 | 26.7 |
| Isomalt (granulated) | 20.27 | 270.3 |
| Croscarmellose sodium | 3.75 | 50 |
| Magnesium stearate | 0.6 | 7.5 |
| Talc | 0.38 | 5.1 |
| 0.0001N HCl* | — | — |
| Total dry weight | 75 | 1000 |

*Water is removed during the manufacturing process

TABLE 66

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Isomalt (powder) | 48 | 96 | 336 | 48 | 144 | 288 | 46.3 |
| Leucine | 0.001 | 0.002 | 0.007 | 0.04 | 0.12 | 0.24 | 0.46 |
| Calcium chloride dihydrate | 0.003 | 0.006 | 0.021 | 0.09 | 0.27 | 0.54 | 1.04 |
| PVP K30 LP | 2 | 4 | 14 | 2 | 6 | 12 | 2 |
| Isomalt (granulated) | 20.27 | 40.54 | 141.89 | 20.27 | 60.81 | 121.6 | 43.75 |
| Croscarmellose sodium | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

Example 61

Pediatric linaclotide IR tablets comprising components as shown in Table 67 may be prepared as described in Example 60 using pregelatinized starch as a tablet filling agent and crospovidone as the disintegrant. The composition of resulting linaclotide IR tablets of different strengths is shown in 68.

TABLE 67

Linaclotide IR tablet, 0.0005 mg/75 mg

| Ingredients | Weight/tablet) (mg) | Theoretical Weight mg/g |
|---|---|---|
| Linaclotide | 0.0005 | 0.007 |
| Isomalt (powder) | 48 | 640 |
| Leucine | 0.001 | 0.013 |
| Calcium chloride dihydrate | 0.003 | 0.04 |
| PVP K30 LP | 2 | 26.7 |
| Pregelatinized starch | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

TABLE 68

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Isomalt (powder) | 48 | 96 | 336 | 48 | 144 | 288 | 46.3 |
| Leucine | 0.001 | 0.002 | 0.007 | 0.04 | 0.12 | 0.24 | 0.46 |
| Calcium chloride dihydrate | 0.003 | 0.006 | 0.021 | 0.09 | 0.27 | 0.54 | 1.04 |
| PVP K30 LP | 2 | 4 | 14 | 2 | 6 | 12 | 2 |
| Pregelatinized starch | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

Example 62

Pediatric linaclotide IR tablets comprising components as shown in Table 69 may be prepared as described in Example 60 using dicalcium phosphate as a granular filling agent and crospovidone as the disintegrant. The composition of resulting linaclotide IR tablets of different strengths is shown in 70.

TABLE 69

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Dicalcium phosphate | 48 | 640 |
| Leucine | 0.001 | 0.013 |
| Calcium chloride dihydrate | 0.003 | 0.04 |
| PVP K30 LP | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

TABLE 70

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Dicalcium phosphate | 48 | 96 | 336 | 48 | 144 | 288 | 46.3 |
| Leucine | 0.001 | 0.002 | 0.007 | 0.04 | 0.12 | 0.24 | 0.46 |
| Calcium chloride dihydrate | 0.003 | 0.006 | 0.021 | 0.09 | 0.27 | 0.54 | 1.04 |
| PVP K30 LP | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

Example 63

Pediatric linaclotide IR tablets comprising components as shown in Table 71 may be prepared as described in Example 62 using Microcrystalline cellulose as a granular filling agent. The composition of resulting linaclotide IR tablets of different strengths is shown in 72.

TABLE 71

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Microcrystalline cellulose | 48 | 640 |
| Leucine | 0.001 | 0.013 |
| Calcium chloride dihydrate | 0.003 | 0.04 |
| PVP K30 LP | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

TABLE 72

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Microcrystalline cellulose | 48 | 96 | 336 | 48 | 144 | 288 | 46.3 |
| Leucine | 0.001 | 0.002 | 0.007 | 0.04 | 0.12 | 0.24 | 0.46 |
| Calcium chloride dihydrate | 0.003 | 0.006 | 0.021 | 0.09 | 0.27 | 0.54 | 1.04 |
| PVP K30 LP | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

Example 64

Pediatric linaclotide IR tablets comprising components as shown in Table 73 may be prepared as described in Example 62 using Mannitol as a granular filling agent. The composition of resulting linaclotide IR tablets of different strengths is shown in 74.

TABLE 73

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Mannitol | 48 | 640 |
| Leucine | 0.001 | 0.013 |
| Calcium chloride dihydrate | 0.003 | 0.04 |
| PVP K30 LP | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

TABLE 74

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Mannitol | 48 | 96 | 336 | 48 | 144 | 288 | 46.3 |
| Leucine | 0.001 | 0.002 | 0.007 | 0.04 | 0.12 | 0.24 | 0.46 |
| Calcium chloride dihydrate | 0.003 | 0.006 | 0.021 | 0.09 | 0.27 | 0.54 | 1.04 |
| PVP K30 LP | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

Example 65

Pediatric linaclotide IR tablets comprising components as shown in Table 75 may be prepared as described in Example 64 using PVA as a stabilizing agent. The composition of resulting linaclotide IR tablets of different strengths is shown in 76.

TABLE 75

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Mannitol | 48 | 640 |
| Leucine | 0.001 | 0.013 |
| Calcium chloride dihydrate | 0.003 | 0.04 |
| Polyvinyl alcohol (PVA) | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

TABLE 76

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Mannitol | 48 | 96 | 336 | 48 | 144 | 288 | 46.3 |
| Leucine | 0.001 | 0.002 | 0.007 | 0.04 | 0.12 | 0.24 | 0.46 |
| Calcium chloride dihydrate | 0.003 | 0.006 | 0.021 | 0.09 | 0.27 | 0.54 | 1.04 |
| Polyvinyl Alcohol | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

Example 66

Pediatric linaclotide IR tablets comprising components as shown in Table 77 may be prepared as described in Example 65 using Trehalose as a granular filling agent. The composition of resulting linaclotide IR tablets of different strengths is shown in 78.

TABLE 77

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Trehalose | 48 | 640 |
| Leucine | 0.001 | 0.013 |
| Calcium chloride dihydrate | 0.003 | 0.04 |
| Polyvinyl alcohol (PVA) | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

Example 67

Pediatric linaclotide IR tablets comprising components as shown in Table 79 may be prepared as described in Example 65 using hydropropyl methyl cellulose as a stabilizing agent. The composition of resulting linaclotide IR tablets of different strengths is shown in 80.

TABLE 79

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Mannitol | 48 | 640 |
| Leucine | 0.001 | 0.013 |
| Calcium chloride dihydrate | 0.003 | 0.04 |
| Hydropropyl methyl cellulose (HPMC) | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

TABLE 78

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Trehalose | 48 | 96 | 336 | 48 | 144 | 288 | 46.3 |
| Leucine | 0.001 | 0.002 | 0.007 | 0.04 | 0.12 | 0.24 | 0.46 |
| Calcium chloride dihydrate | 0.003 | 0.006 | 0.021 | 0.09 | 0.27 | 0.54 | 1.04 |
| Polyvinyl Alcohol | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

TABLE 80

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Mannitol | 48 | 96 | 336 | 48 | 144 | 288 | 46.3 |
| Leucine | 0.001 | 0.002 | 0.007 | 0.04 | 0.12 | 0.24 | 0.46 |
| Calcium chloride dihydrate | 0.003 | 0.006 | 0.021 | 0.09 | 0.27 | 0.54 | 1.04 |
| Hydropropyl methyl cellulose (HPMC) | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

Example 68

Pediatric linaclotide IR tablets comprising components as shown in Table 81 may be prepared as described in Example 66 using Erythitol as a granular filling agent. The composition of resulting linaclotide IR tablets of different strengths is shown in 82.

TABLE 81

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Erythitol | 48 | 640 |
| Leucine | 0.001 | 0.013 |
| Calcium chloride dihydrate | 0.003 | 0.04 |
| Polyvinyl alcohol (PVA) | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

TABLE 82

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Erythitol | 48 | 96 | 336 | 48 | 144 | 288 | 46.3 |
| Leucine | 0.001 | 0.002 | 0.007 | 0.04 | 0.12 | 0.24 | 0.46 |
| Calcium chloride dihydrate | 0.003 | 0.006 | 0.021 | 0.09 | 0.27 | 0.54 | 1.04 |
| Polyvinyl Alcohol | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

Example 69

Pediatric linaclotide IR tablets comprising components as shown in Table 83 may be prepared as described in Example 68 using Maltitol as a granular filling agent. The composition of resulting linaclotide IR tablets of different strengths is shown in 84.

TABLE 83

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Maltitol | 48 | 640 |
| Leucine | 0.001 | 0.013 |
| Calcium chloride dihydrate | 0.003 | 0.04 |

TABLE 83-continued

Linaclotide IR tablet, 0.0005 mg/75 mg

| Ingredients | Weight/tablet (mg) | Theoretical Weight mg/g |
|---|---|---|
| Polyvinyl alcohol (PVA) | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

TABLE 84

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Maltitol | 48 | 96 | 336 | 48 | 144 | 288 | 46.3 |
| Leucine | 0.001 | 0.002 | 0.007 | 0.04 | 0.12 | 0.24 | 0.46 |
| Calcium chloride dihydrate | 0.003 | 0.006 | 0.021 | 0.09 | 0.27 | 0.54 | 1.04 |
| Polyvinyl Alcohol | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

Example 70

Pediatric linaclotide IR tablets comprising components as shown in Table 85 may be prepared as described in Example 69 using lactose as a granular filling agent. The composition of resulting linaclotide IR tablets of different strengths is shown in 86.

TABLE 85

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Lactose | 48 | 640 |
| Leucine | 0.001 | 0.013 |
| Calcium chloride dihydrate | 0.003 | 0.04 |
| Polyvinyl alcohol (PVA) | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

TABLE 86

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Lactose | 48 | 96 | 336 | 48 | 144 | 288 | 46.3 |
| Leucine | 0.001 | 0.002 | 0.007 | 0.04 | 0.12 | 0.24 | 0.46 |
| Calcium chloride dihydrate | 0.003 | 0.006 | 0.021 | 0.09 | 0.27 | 0.54 | 1.04 |
| Polyvinyl Alcohol | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

Example 71

Pediatric linaclotide IR tablets comprising components as shown in Table 87 may be prepared as described in Example 70 using glucose as a granular filling agent. The composition of resulting linaclotide IR tablets of different strengths is shown in 88.

TABLE 87

| Linaclotide IR tablet, 0.0005 mg/75 mg | | |
|---|---|---|
| Ingredients | Weight/tablet (mg) | Theoretical Weight mg/g |
| Linaclotide | 0.0005 | 0.007 |
| Glucose | 48 | 640 |
| Leucine | 0.001 | 0.013 |
| Calcium chloride dihydrate | 0.003 | 0.04 |
| Polyvinyl alcohol (PVA) | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

TABLE 88

| Linaclotide IR tablets of different strengths | | | | | | | |
|---|---|---|---|---|---|---|---|
| | Tablet composition of strength (mcg) | | | | | | |
| Components | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Glucose | 48 | 96 | 336 | 48 | 144 | 288 | 46.3 |
| Leucine | 0.001 | 0.002 | 0.007 | 0.04 | 0.12 | 0.24 | 0.46 |
| Calcium chloride dihydrate | 0.003 | 0.006 | 0.021 | 0.09 | 0.27 | 0.54 | 1.04 |
| Polyvinyl Alcohol | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

Example 72

Pediatric linaclotide IR tablets comprising components as shown in Table 89 may be prepared as described in Example 65 using isoleucine as a stabilizing agent. The composition of resulting linaclotide IR tablets of different strengths is shown in 90.

TABLE 89

| Linaclotide IR tablet, 0.0005 mg/75 mg | | |
|---|---|---|
| Ingredients | Weight/tablet (mg) | Theoretical Weight mg/g |
| Linaclotide | 0.0005 | 0.007 |
| Mannitol | 48 | 640 |
| Isoleucine | 0.001 | 0.013 |
| Calcium chloride dihydrate | 0.003 | 0.04 |
| Polyvinyl alcohol (PVA) | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

TABLE 90

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Mannitol | 48 | 96 | 336 | 48 | 144 | 288 | 46.3 |
| Isoleucine | 0.001 | 0.002 | 0.007 | 0.04 | 0.12 | 0.24 | 0.46 |
| Calcium chloride dihydrate | 0.003 | 0.006 | 0.021 | 0.09 | 0.27 | 0.54 | 1.04 |
| Polyvinyl Alcohol | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

Example 73

Pediatric linaclotide IR tablets comprising components as shown in Table 91 may be prepared as described in Example 72 using Asparagine as a stabilizing agent. The composition of resulting linaclotide IR tablets of different strengths is shown in 92.

TABLE 91

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Mannitol | 48 | 640 |
| Asparagine | 0.001 | 0.013 |
| Calcium chloride dihydrate | 0.003 | 0.04 |
| Polyvinyl alcohol (PVA) | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

TABLE 92

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Mannitol | 48 | 96 | 336 | 48 | 144 | 288 | 46.3 |
| Asparagine | 0.001 | 0.002 | 0.007 | 0.04 | 0.12 | 0.24 | 0.46 |
| Calcium chloride dihydrate | 0.003 | 0.006 | 0.021 | 0.09 | 0.27 | 0.54 | 1.04 |
| Polyvinyl Alcohol | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

Example 74

Pediatric linaclotide IR tablets comprising components as shown in Table 93 may be prepared as described in Example 73 using Glutamine as a stabilizing agent. The composition of resulting linaclotide IR tablets of different strengths is shown in 94.

TABLE 93

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Mannitol | 48 | 640 |
| Glutamine | 0.001 | 0.013 |
| Calcium chloride dihydrate | 0.003 | 0.04 |
| Polyvinyl alcohol (PVA) | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

TABLE 94

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Mannitol | 48 | 96 | 336 | 48 | 144 | 288 | 46.3 |
| Glutamine | 0.001 | 0.002 | 0.007 | 0.04 | 0.12 | 0.24 | 0.46 |
| Calcium chloride dihydrate | 0.003 | 0.006 | 0.021 | 0.09 | 0.27 | 0.54 | 1.04 |
| Polyvinyl Alcohol | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

Example 75

Pediatric linaclotide IR tablets comprising components as shown in Table 95 may be prepared as described in Example 74 using glycine as a stabilizing agent. The composition of resulting linaclotide IR tablets of different strengths is shown in 96.

TABLE 95

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Mannitol | 48 | 640 |
| Glycine | 0.001 | 0.013 |
| Calcium chloride dihydrate | 0.003 | 0.04 |
| Polyvinyl alcohol (PVA) | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

Example 76

Pediatric linaclotide IR tablets comprising components as shown in Table 97 may be prepared as described in Example 75 using histidine as a stabilizing agent. The composition of resulting linaclotide IR tablets of different strengths is shown in 98.

TABLE 97

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Mannitol | 48 | 640 |
| Histidine | 0.001 | 0.013 |
| Calcium chloride dihydrate | 0.003 | 0.04 |
| Polyvinyl alcohol (PVA) | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

TABLE 96

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Mannitol | 48 | 96 | 336 | 48 | 144 | 288 | 46.3 |
| Glycine | 0.001 | 0.002 | 0.007 | 0.04 | 0.12 | 0.24 | 0.46 |
| Calcium chloride dihydrate | 0.003 | 0.006 | 0.021 | 0.09 | 0.27 | 0.54 | 1.04 |
| Polyvinyl Alcohol | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

TABLE 98

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Mannitol | 48 | 96 | 336 | 48 | 144 | 288 | 46.3 |
| Histidine | 0.001 | 0.002 | 0.007 | 0.04 | 0.12 | 0.24 | 0.46 |
| Calcium chloride dihydrate | 0.003 | 0.006 | 0.021 | 0.09 | 0.27 | 0.54 | 1.04 |
| Polyvinyl Alcohol | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

Example 77

Pediatric linaclotide IR tablets comprising components as shown in Table 99 may be prepared as described in Example 76 using tyrosine as a stabilizing agent. The composition of resulting linaclotide IR tablets of different strengths is shown in 100.

TABLE 99

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Mannitol | 48 | 640 |
| Tyrosine | 0.001 | 0.013 |
| Calcium chloride dihydrate | 0.003 | 0.04 |
| Polyvinyl alcohol (PVA) | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

TABLE 100

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Mannitol | 48 | 96 | 336 | 48 | 144 | 288 | 46.3 |
| Tyrosine | 0.001 | 0.002 | 0.007 | 0.04 | 0.12 | 0.24 | 0.46 |
| Calcium chloride dihydrate | 0.003 | 0.006 | 0.021 | 0.09 | 0.27 | 0.54 | 1.04 |
| Polyvinyl Alcohol | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

Example 78

Pediatric linaclotide IR tablets comprising components as shown in Table 101 may be prepared as described in Example 77 using lysine as a stabilizing agent. The composition of resulting linaclotide IR tablets of different strengths is shown in 102.

TABLE 101

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Mannitol | 48 | 640 |
| Lysine | 0.001 | 0.013 |
| Calcium chloride dihydrate | 0.003 | 0.04 |
| Polyvinyl alcohol (PVA) | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

TABLE 102

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Mannitol | 48 | 96 | 336 | 48 | 144 | 288 | 46.3 |
| Lysine | 0.001 | 0.002 | 0.007 | 0.04 | 0.12 | 0.24 | 0.46 |
| Calcium chloride dihydrate | 0.003 | 0.006 | 0.021 | 0.09 | 0.27 | 0.54 | 1.04 |
| Polyvinyl Alcohol | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

Example 79

Pediatric linaclotide IR tablets comprising components as shown in Table 103 may be prepared as described in Example 78 using cystine as a stabilizing agent. The composition of resulting linaclotide IR tablets of different strengths is shown in 104.

TABLE 103

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Mannitol | 48 | 640 |
| Cystine | 0.001 | 0.013 |
| Calcium chloride dihydrate | 0.003 | 0.04 |
| Polyvinyl alcohol (PVA) | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

Example 80

Pediatric linaclotide IR tablets comprising components as shown in Table 105 may be prepared as described in Example 79 using alanine as a stabilizing agent. The composition of resulting linaclotide IR tablets of different strengths is shown in 106.

TABLE 105

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Mannitol | 48 | 640 |
| Alanine | 0.001 | 0.013 |
| Calcium chloride dihydrate | 0.003 | 0.04 |
| Polyvinyl alcohol (PVA) | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

TABLE 104

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Mannitol | 48 | 96 | 336 | 48 | 144 | 288 | 46.3 |
| Cystine | 0.001 | 0.002 | 0.007 | 0.04 | 0.12 | 0.24 | 0.46 |
| Calcium chloride dihydrate | 0.003 | 0.006 | 0.021 | 0.09 | 0.27 | 0.54 | 1.04 |
| Polyvinyl Alcohol | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

TABLE 106

Linaclotide IR tablets of different strengths

| | Tablet composition of strength (mcg) | | | | | | |
|---|---|---|---|---|---|---|---|
| Components | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Mannitol | 48 | 96 | 336 | 48 | 144 | 288 | 46.3 |
| Alanine | 0.001 | 0.002 | 0.007 | 0.04 | 0.12 | 0.24 | 0.46 |
| Calcium chloride dihydrate | 0.003 | 0.006 | 0.021 | 0.09 | 0.27 | 0.54 | 1.04 |
| Polyvinyl Alcohol | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

Example 81

Pediatric linaclotide IR tablets comprising components as shown in Table 107 may be prepared as described in Example 80 using serine as a stabilizing agent. The composition of resulting linaclotide IR tablets of different strengths is shown in 108.

TABLE 107

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Mannitol | 48 | 640 |
| Serine | 0.001 | 0.013 |
| Calcium chloride dihydrate | 0.003 | 0.04 |
| Polyvinyl alcohol (PVA) | 2 | 26.7 |
| Isomalt (granulated) | 20.27 | 270.3 |
| Croscarmellose sodium | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

Example 82

Pediatric linaclotide IR tablets comprising components as shown in Table 109 may be prepared as described in Example 81 using threonine as a stabilizing agent. The composition of resulting linaclotide IR tablets of different strengths is shown in 110.

TABLE 109

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Mannitol | 48 | 640 |
| Threonine | 0.001 | 0.013 |
| Calcium chloride dihydrate | 0.003 | 0.04 |
| Polyvinyl alcohol (PVA) | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

TABLE 108

Linaclotide IR tablets of different strengths

| | Tablet composition of strength (mcg) | | | | | | |
|---|---|---|---|---|---|---|---|
| Components | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Mannitol | 48 | 96 | 336 | 48 | 144 | 288 | 46.3 |
| Serine | 0.001 | 0.002 | 0.007 | 0.04 | 0.12 | 0.24 | 0.46 |
| Calcium chloride dihydrate | 0.003 | 0.006 | 0.021 | 0.09 | 0.27 | 0.54 | 1.04 |
| Polyvinyl Alcohol | 2 | 4 | 14 | 2 | 6 | 12 | 2 |
| Isomalt | 20.27 | 40.54 | 141.89 | 20.27 | 60.81 | 121.6 | 43.75 |
| Croscarmellose sodium | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

TABLE 110

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Mannitol | 48 | 96 | 336 | 48 | 144 | 288 | 46.3 |
| Threonine | 0.001 | 0.002 | 0.007 | 0.04 | 0.12 | 0.24 | 0.46 |
| Calcium chloride dihydrate | 0.003 | 0.006 | 0.021 | 0.09 | 0.27 | 0.54 | 1.04 |
| Polyvinyl Alcohol | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

Example 83

Pediatric linaclotide IR tablets comprising components as shown in Table 111 may be prepared as described in Example 82 using proline as a stabilizing agent. The composition of resulting linaclotide IR tablets of different strengths is shown in 112.

TABLE 111

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Mannitol | 48 | 640 |
| Proline | 0.001 | 0.013 |
| Calcium chloride dihydrate | 0.003 | 0.04 |
| Polyvinyl alcohol (PVA) | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

Example 84

Pediatric linaclotide IR tablets comprising components as shown in Table 113 may be prepared as described in Example 83 using tryptophan as a stabilizing agent. The composition of resulting linaclotide IR tablets of different strengths is shown in 114.

TABLE 113

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Mannitol | 48 | 640 |
| Tryptophan | 0.001 | 0.013 |
| Calcium chloride dihydrate | 0.003 | 0.04 |
| Polyvinyl alcohol (PVA) | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

TABLE 112

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Mannitol | 48 | 96 | 336 | 48 | 144 | 288 | 46.3 |
| Proline | 0.001 | 0.002 | 0.007 | 0.04 | 0.12 | 0.24 | 0.46 |
| Calcium chloride dihydrate | 0.003 | 0.006 | 0.021 | 0.09 | 0.27 | 0.54 | 1.04 |
| Polyvinyl Alcohol | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

TABLE 114

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Mannitol | 48 | 96 | 336 | 48 | 144 | 288 | 46.3 |
| Tryptophan | 0.001 | 0.002 | 0.007 | 0.04 | 0.12 | 0.24 | 0.46 |
| Calcium chloride dihydrate | 0.003 | 0.006 | 0.021 | 0.09 | 0.27 | 0.54 | 1.04 |
| Polyvinyl Alcohol | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

Example 85

Pediatric linaclotide IR tablets comprising components as shown in Table 115 may be prepared as described in Example 84 using leucine and potassium chloride as stabilizing agents. The composition of resulting linaclotide IR tablets of different strengths is shown in 116.

TABLE 115

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Mannitol | 48 | 640 |
| Leucine | 0.001 | 0.013 |
| Potassium chloride | 0.003 | 0.04 |
| Polyvinyl alcohol (PVA) | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

Example 86

Pediatric linaclotide IR tablets comprising components as shown in Table 117 may be prepared as described in Example 85 using sodium chloride as a stabilizing agent. The composition of resulting linaclotide IR tablets of different strengths is shown in 118.

TABLE 117

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Mannitol | 48 | 640 |
| Leucine | 0.001 | 0.013 |
| Sodium chloride | 0.003 | 0.04 |
| Polyvinyl alcohol (PVA) | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

TABLE 116

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Mannitol | 48 | 96 | 336 | 48 | 144 | 288 | 46.3 |
| Leucine | 0.001 | 0.002 | 0.007 | 0.04 | 0.12 | 0.24 | 0.46 |
| Potassium chloride | 0.003 | 0.006 | 0.021 | 0.09 | 0.27 | 0.54 | 1.04 |
| Polyvinyl Alcohol | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

TABLE 118

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Mannitol | 48 | 96 | 336 | 48 | 144 | 288 | 46.3 |
| Leucine | 0.001 | 0.002 | 0.007 | 0.04 | 0.12 | 0.24 | 0.46 |
| Sodium chloride | 0.003 | 0.006 | 0.021 | 0.09 | 0.27 | 0.54 | 1.04 |
| Polyvinyl Alcohol | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

Example 87

Pediatric linaclotide IR tablets comprising components as shown in Table 119 may be prepared as described in Example 86 using magnesium chloride as a stabilizing agent. The composition of resulting linaclotide IR tablets of different strengths is shown in 120.

TABLE 119

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Mannitol | 48 | 640 |
| Leucine | 0.001 | 0.013 |
| Magnesium chloride | 0.003 | 0.04 |
| Polyvinyl alcohol (PVA) | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

Example 88

Pediatric linaclotide IR tablets comprising components as shown in Table 121 may be prepared as described in Example 87 using iron chloride as a stabilizing agent. The composition of resulting linaclotide IR tablets of different strengths is shown in 122.

TABLE 121

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Mannitol | 48 | 640 |
| Leucine | 0.001 | 0.013 |
| Iron chloride | 0.003 | 0.04 |
| Polyvinyl alcohol (PVA) | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

TABLE 120

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Mannitol | 48 | 96 | 336 | 48 | 144 | 288 | 46.3 |
| Leucine | 0.001 | 0.002 | 0.007 | 0.04 | 0.12 | 0.24 | 0.46 |
| Magnesium chloride | 0.003 | 0.006 | 0.021 | 0.09 | 0.27 | 0.54 | 1.04 |
| Polyvinyl Alcohol | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

TABLE 122

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Mannitol | 48 | 96 | 336 | 48 | 144 | 288 | 46.3 |
| Leucine | 0.001 | 0.002 | 0.007 | 0.04 | 0.12 | 0.24 | 0.46 |
| Iron chloride | 0.003 | 0.006 | 0.021 | 0.09 | 0.27 | 0.54 | 1.04 |
| Polyvinyl Alcohol | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

Example 89

Pediatric linaclotide IR tablets comprising components as shown in Table 123 may be prepared as described in Example 88 using copper chloride as a stabilizing agent. The composition of resulting linaclotide IR tablets of different strengths is shown in 124.

TABLE 123

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Mannitol | 48 | 640 |
| Leucine | 0.001 | 0.013 |
| Copper chloride | 0.003 | 0.04 |
| Polyvinyl alcohol (PVA) | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

Example 90

Pediatric linaclotide IR tablets comprising components as shown in Table 125 may be prepared as described in Example 89 using zinc chloride as a stabilizing agent. The composition of resulting linaclotide IR tablets of different strengths is shown in 126.

TABLE 125

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Mannitol | 48 | 640 |
| Leucine | 0.001 | 0.013 |
| Zinc chloride | 0.003 | 0.04 |
| Polyvinyl alcohol (PVA) | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

TABLE 124

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Mannitol | 48 | 96 | 336 | 48 | 144 | 288 | 46.3 |
| Leucine | 0.001 | 0.002 | 0.007 | 0.04 | 0.12 | 0.24 | 0.46 |
| Copper chloride | 0.003 | 0.006 | 0.021 | 0.09 | 0.27 | 0.54 | 1.04 |
| Polyvinyl Alcohol | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

TABLE 126

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Mannitol | 48 | 96 | 336 | 48 | 144 | 288 | 46.3 |
| Leucine | 0.001 | 0.002 | 0.007 | 0.04 | 0.12 | 0.24 | 0.46 |
| Zinc chloride | 0.003 | 0.006 | 0.021 | 0.09 | 0.27 | 0.54 | 1.04 |
| Polyvinyl Alcohol | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

Example 91

Pediatric linaclotide IR tablets comprising components as shown in Table 127 may be prepared as described in Example 90 using aluminum chloride as a stabilizing agent. The composition of resulting linaclotide IR tablets of different strengths is shown in 128.

TABLE 127

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Mannitol | 48 | 640 |
| Leucine | 0.001 | 0.013 |
| Aluminum chloride | 0.003 | 0.04 |
| Polyvinyl alcohol (PVA) | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

Example 92

Pediatric linaclotide IR tablets comprising components as shown in Table 129 may be prepared as described in Example 91 using barium chloride as a stabilizing agent. The composition of resulting linaclotide IR tablets of different strengths is shown in 130.

TABLE 129

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Mannitol | 48 | 640 |
| Leucine | 0.001 | 0.013 |
| Barium chloride | 0.003 | 0.04 |
| Polyvinyl alcohol (PVA) | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

TABLE 128

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Mannitol | 48 | 96 | 336 | 48 | 144 | 288 | 46.3 |
| Leucine | 0.001 | 0.002 | 0.007 | 0.04 | 0.12 | 0.24 | 0.46 |
| Aluminum chloride | 0.003 | 0.006 | 0.021 | 0.09 | 0.27 | 0.54 | 1.04 |
| Polyvinyl Alcohol | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

TABLE 130

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Mannitol | 48 | 96 | 336 | 48 | 144 | 288 | 46.3 |
| Leucine | 0.001 | 0.002 | 0.007 | 0.04 | 0.12 | 0.24 | 0.46 |
| Barium chloride | 0.003 | 0.006 | 0.021 | 0.09 | 0.27 | 0.54 | 1.04 |
| Polyvinyl Alcohol | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

Example 93

Pediatric linaclotide IR tablets comprising components as shown in Table 131 may be prepared as described in Example 92 using Manganese chloride as a stabilizing agent. The composition of resulting linaclotide IR tablets of different strengths is shown in 132.

TABLE 131

Linaclotide Table 11 Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Mannitol | 48 | 640 |
| Leucine | 0.001 | 0.013 |
| Manganese chloride | 0.003 | 0.04 |
| Polyvinyl alcohol (PVA) | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

TABLE 132

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Mannitol | 48 | 96 | 336 | 48 | 144 | 288 | 46.3 |
| Leucine | 0.001 | 0.002 | 0.007 | 0.04 | 0.12 | 0.24 | 0.46 |
| Manganese chloride | 0.003 | 0.006 | 0.021 | 0.09 | 0.27 | 0.54 | 1.04 |
| Polyvinyl Alcohol | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

Example 94

Pediatric linaclotide IR tablets comprising components as shown in Table 133 may be prepared as described in Example 64 using Pluronic as a stabilizing agent. The composition of resulting linaclotide IR tablets of different strengths is shown in 134.

TABLE 133

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Mannitol | 48 | 640 |
| Leucine | 0.001 | 0.013 |
| Calcium chloride dihydrate | 0.003 | 0.04 |
| Pluronic | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

TABLE 134

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Mannitol | 48 | 96 | 336 | 48 | 144 | 288 | 46.3 |
| Leucine | 0.001 | 0.002 | 0.007 | 0.04 | 0.12 | 0.24 | 0.46 |
| Calcium chloride dihydrate | 0.003 | 0.006 | 0.021 | 0.09 | 0.27 | 0.54 | 1.04 |
| Pluronic | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

Example 95

Pediatric linaclotide IR tablets comprising components as shown in Table 135 may be prepared as described in Example 94 using gelatin as a stabilizing agent. The composition of resulting linaclotide IR tablets of different strengths is shown in 136.

TABLE 135

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Mannitol | 48 | 640 |
| Leucine | 0.001 | 0.013 |
| Calcium chloride dihydrate | 0.003 | 0.04 |
| Gelatin | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

Example 96

Pediatric linaclotide IR tablets comprising components as shown in Table 137 may be prepared as described in Example 95 using chitosan as a stabilizing agent. The composition of resulting linaclotide IR tablets of different strengths is shown in 138.

TABLE 137

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Mannitol | 48 | 640 |
| Leucine | 0.001 | 0.013 |
| Calcium chloride dihydrate | 0.003 | 0.04 |
| Chitosan | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

TABLE 136

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Mannitol | 48 | 96 | 336 | 48 | 144 | 288 | 46.3 |
| Leucine | 0.001 | 0.002 | 0.007 | 0.04 | 0.12 | 0.24 | 0.46 |
| Calcium chloride dihydrate | 0.003 | 0.006 | 0.021 | 0.09 | 0.27 | 0.54 | 1.04 |
| Gelatin | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

TABLE 138

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Mannitol | 48 | 96 | 336 | 48 | 144 | 288 | 46.3 |
| Leucine | 0.001 | 0.002 | 0.007 | 0.04 | 0.12 | 0.24 | 0.46 |
| Calcium chloride dihydrate | 0.003 | 0.006 | 0.021 | 0.09 | 0.27 | 0.54 | 1.04 |
| Chitosan | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

Example 97

Pediatric linaclotide IR tablets comprising components as shown in Table 139 may be prepared as described in Example 96 using cyclodextrin as a stabilizing agent. The composition of resulting linaclotide IR tablets of different strengths is shown in 140.

TABLE 139

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Mannitol | 48 | 640 |
| Leucine | 0.001 | 0.013 |
| Calcium chloride dihydrate | 0.003 | 0.04 |
| Cyclodextrin | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

Example 98

Pediatric linaclotide IR tablets comprising components as shown in Table 141 may be prepared as described in Example 97 using guar gum as a stabilizing agent. The composition of resulting linaclotide IR tablets of different strengths is shown in 142.

TABLE 141

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Mannitol | 48 | 640 |
| Leucine | 0.001 | 0.013 |
| Calcium chloride dihydrate | 0.003 | 0.04 |
| Guar gum | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

TABLE 140

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Mannitol | 48 | 96 | 336 | 48 | 144 | 288 | 46.3 |
| Leucine | 0.001 | 0.002 | 0.007 | 0.04 | 0.12 | 0.24 | 0.46 |
| Calcium chloride dihydrate | 0.003 | 0.006 | 0.021 | 0.09 | 0.27 | 0.54 | 1.04 |
| Cyclodextrin | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

TABLE 142

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Mannitol | 48 | 96 | 336 | 48 | 144 | 288 | 46.3 |
| Leucine | 0.001 | 0.002 | 0.007 | 0.04 | 0.12 | 0.24 | 0.46 |
| Calcium chloride dihydrate | 0.003 | 0.006 | 0.021 | 0.09 | 0.27 | 0.54 | 1.04 |
| Guar gum | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

Example 99

Pediatric linaclotide IR tablets comprising components as shown in Table 143 may be prepared as described in Example 98 using Xanthan gum as a stabilizing agent. The composition of resulting linaclotide IR tablets of different strengths is shown in 144.

TABLE 143

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Mannitol | 48 | 640 |
| Leucine | 0.001 | 0.013 |
| Calcium chloride dihydrate | 0.003 | 0.04 |
| Xanthan gum | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

Example 100

Pediatric linaclotide IR tablets comprising components as shown in Table 145 may be prepared as described in Example 99 using Dextran as a stabilizing agent. The composition of resulting linaclotide IR tablets of different strengths is shown in 146.

TABLE 145

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Mannitol | 48 | 640 |
| Leucine | 0.001 | 0.013 |
| Calcium chloride dihydrate | 0.003 | 0.04 |
| Dextran | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

TABLE 144

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Mannitol | 48 | 96 | 336 | 48 | 144 | 288 | 46.3 |
| Leucine | 0.001 | 0.002 | 0.007 | 0.04 | 0.12 | 0.24 | 0.46 |
| Calcium chloride dihydrate | 0.003 | 0.006 | 0.021 | 0.09 | 0.27 | 0.54 | 1.04 |
| Xanthan gum | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

TABLE 146

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Mannitol | 48 | 96 | 336 | 48 | 144 | 288 | 46.3 |
| Leucine | 0.001 | 0.002 | 0.007 | 0.04 | 0.12 | 0.24 | 0.46 |
| Calcium chloride dihydrate | 0.003 | 0.006 | 0.021 | 0.09 | 0.27 | 0.54 | 1.04 |
| Dextran | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

Example 101

Pediatric linaclotide IR tablets comprising components as shown in Table 147 may be prepared as described in Example 100 using Dextrin as a stabilizing agent. The composition of resulting linaclotide IR tablets of different strengths is shown in 148.

TABLE 147

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Mannitol | 48 | 640 |
| Leucine | 0.001 | 0.013 |
| Calcium chloride dihydrate | 0.003 | 0.04 |
| Dextrin | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

TABLE 148

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Mannitol | 48 | 96 | 336 | 48 | 144 | 288 | 46.3 |
| Leucine | 0.001 | 0.002 | 0.007 | 0.04 | 0.12 | 0.24 | 0.46 |
| Calcium chloride dihydrate | 0.003 | 0.006 | 0.021 | 0.09 | 0.27 | 0.54 | 1.04 |
| Dextrin | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

Example 102

Pediatric linaclotide IR tablets comprising components as shown in Table 149 may be prepared as described in Example 101 using Polyethylene polypropylene oxide as a stabilizing agent. The composition of resulting linaclotide IR tablets of different strengths is shown in 150.

TABLE 149

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Mannitol | 48 | 640 |
| Leucine | 0.001 | 0.013 |
| Calcium chloride dihydrate | 0.003 | 0.04 |
| Polyethylene polypropylene oxide | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

TABLE 150

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Mannitol | 48 | 96 | 336 | 48 | 144 | 288 | 46.3 |
| Leucine | 0.001 | 0.002 | 0.007 | 0.04 | 0.12 | 0.24 | 0.46 |
| Calcium chloride dihydrate | 0.003 | 0.006 | 0.021 | 0.09 | 0.27 | 0.54 | 1.04 |
| Polyethylene polypropylene oxide | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

Example 103

Pediatric linaclotide IR tablets comprising components as shown in Table 151 may be prepared as described in Example 102 using polyacrylic acid as a stabilizing agent. The composition of resulting linaclotide IR tablets of different strengths is shown in 152.

TABLE 151

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Mannitol | 48 | 640 |
| Leucine | 0.001 | 0.013 |
| Calcium chloride dihydrate | 0.003 | 0.04 |
| Polyacrylic acid | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

TABLE 152

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Mannitol | 48 | 96 | 336 | 48 | 144 | 288 | 46.3 |
| Leucine | 0.001 | 0.002 | 0.007 | 0.04 | 0.12 | 0.24 | 0.46 |
| Calcium chloride dihydrate | 0.003 | 0.006 | 0.021 | 0.09 | 0.27 | 0.54 | 1.04 |
| Polyacrylic acid | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

Example 104

Pediatric linaclotide IR tablets comprising components as shown in Table 153 may be prepared as described in Example 103 using Hydroxypropyl cellulose as a stabilizing agent. The composition of resulting linaclotide IR tablets of different strengths is shown in 154.

TABLE 153

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Mannitol | 48 | 640 |
| Leucine | 0.001 | 0.013 |
| Calcium chloride dihydrate | 0.003 | 0.04 |

TABLE 153-continued

Linaclotide IR tablet, 0.0005 mg/75 mg

| Ingredients | Weight/tablet (mg) | Theoretical Weight mg/g |
|---|---|---|
| Hydroxypropyl cellulose (HPC) | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

TABLE 154

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Mannitol | 48 | 96 | 336 | 48 | 144 | 288 | 46.3 |
| Leucine | 0.001 | 0.002 | 0.007 | 0.04 | 0.12 | 0.24 | 0.46 |
| Calcium chloride dihydrate | 0.003 | 0.006 | 0.021 | 0.09 | 0.27 | 0.54 | 1.04 |
| Hydroxypropyl cellulose (HPC) | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

Example 105

Pediatric linaclotide IR tablets comprising components as shown in Table 155 may be prepared as described in Example 104 using methyl cellulose as a stabilizing agent. The composition of resulting linaclotide IR tablets of different strengths is shown in 156.

TABLE 155

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Mannitol | 48 | 640 |
| Leucine | 0.001 | 0.013 |
| Calcium chloride dihydrate | 0.003 | 0.04 |
| Methyl cellulose | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

TABLE 156

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Mannitol | 48 | 96 | 336 | 48 | 144 | 288 | 46.3 |
| Leucine | 0.001 | 0.002 | 0.007 | 0.04 | 0.12 | 0.24 | 0.46 |
| Calcium chloride dihydrate | 0.003 | 0.006 | 0.021 | 0.09 | 0.27 | 0.54 | 1.04 |
| Methyl cellulose | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

Example 106

Pediatric linaclotide IR tablets comprising components as shown in Table 157 may be prepared as described in Example 105 using Poly(sodium vinylsulfonate) as a stabilizing agent. The composition of resulting linaclotide IR tablets of different strengths is shown in 158.

TABLE 157

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Mannitol | 48 | 640 |
| Leucine | 0.001 | 0.013 |
| Calcium chloride dihydrate | 0.003 | 0.04 |
| Poly(sodium vinylsulfonate) | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

TABLE 158

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Mannitol | 48 | 96 | 336 | 48 | 144 | 288 | 46.3 |
| Leucine | 0.001 | 0.002 | 0.007 | 0.04 | 0.12 | 0.24 | 0.46 |
| Calcium chloride dihydrate | 0.003 | 0.006 | 0.021 | 0.09 | 0.27 | 0.54 | 1.04 |
| Poly(sodium vinylsulfonate) | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

Example 107

Pediatric linaclotide IR tablets comprising components as shown in Table 159 may be prepared as described in Example 106 using polyethylene glycol as a stabilizing agent. The composition of resulting linaclotide IR tablets of different strengths is shown in 160.

TABLE 159

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Mannitol | 48 | 640 |
| Leucine | 0.001 | 0.013 |
| Calcium chloride dihydrate | 0.003 | 0.04 |
| Polyethylene glycol | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

TABLE 160

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Mannitol | 48 | 96 | 336 | 48 | 144 | 288 | 46.3 |
| Leucine | 0.001 | 0.002 | 0.007 | 0.04 | 0.12 | 0.24 | 0.46 |
| Calcium chloride dihydrate | 0.003 | 0.006 | 0.021 | 0.09 | 0.27 | 0.54 | 1.04 |
| Polyethylene glycol | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

Example 108

Pediatric linaclotide IR tablets comprising components as shown in Table 161 may be prepared as described in Example 107 using Polycarbophil as a stabilizing agent. The composition of resulting linaclotide IR tablets of different strengths is shown in 162.

TABLE 161

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Mannitol | 48 | 640 |
| Leucine | 0.001 | 0.013 |
| Calcium chloride dihydrate | 0.003 | 0.04 |
| Polycarbophil | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

TABLE 162

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Mannitol | 48 | 96 | 336 | 48 | 144 | 288 | 46.3 |
| Leucine | 0.001 | 0.002 | 0.007 | 0.04 | 0.12 | 0.24 | 0.46 |
| Calcium chloride dihydrate | 0.003 | 0.006 | 0.021 | 0.09 | 0.27 | 0.54 | 1.04 |
| polycarbophil | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

Example 109

Pediatric linaclotide IR tablets comprising components as shown in Table 163 may be prepared as described in Example 108 using Polyvinyl pyrrolidone-co vinyl acetate as a stabilizing agent. The composition of resulting linaclotide IR tablets of different strengths is shown in 164.

TABLE 163

Linaclotide IR tablet, 0.0005 mg/75 mg

| Ingredients | Weight/tablet (mg) | Theoretical Weight mg/g |
|---|---|---|
| Linaclotide | 0.0005 | 0.007 |
| Mannitol | 48 | 640 |
| Leucine | 0.001 | 0.013 |
| Calcium chloride dihydrate | 0.003 | 0.04 |
| Polyvinyl pyrrolidone-co vinyl acetate | 2 | 26.7 |
| Isomalt (granulated) | 20.27 | 270.3 |
| Crospovidone | 3.75 | 50 |
| Magnesium stearate | 0.6 | 7.5 |
| Talc | 0.38 | 5 |
| 0.0001N HCl* | — | — |
| Total dry weight | 75 | 1000 |

*Water is removed during the manufacturing process

TABLE 164

Linaclotide IR tablets of different strengths

| Components | Tablet composition of strength (mcg) | | | | | | |
|---|---|---|---|---|---|---|---|
| | 0.5 single dose | 1 single dose | 3.5 7 day supply | 15 1 month supply | 45 3 month supply | 90 6 month supply | 180 1 year supply |
| linaclotide | 0.0005 | 0.001 | 0.0035 | 0.015 | 0.045 | 0.09 | 0.18 |
| Mannitol | 48 | 96 | 336 | 48 | 144 | 288 | 46.3 |
| Leucine | 0.001 | 0.002 | 0.007 | 0.04 | 0.12 | 0.24 | 0.46 |
| Calcium chloride dihydrate | 0.003 | 0.006 | 0.021 | 0.09 | 0.27 | 0.54 | 1.04 |
| Polyvinyl pyrrolidone-co vinyl acetate | 2 | 4 | 14 | 2 | 6 | 12 | 2 |
| Isomalt | 20.27 | 40.54 | 141.89 | 20.27 | 60.81 | 121.6 | 43.75 |
| Crospovidone | 3.75 | 7.5 | 26.25 | 3.75 | 11.25 | 22.5 | 5 |
| Magnesium stearate | 0.6 | 1.2 | 4.2 | 0.6 | 1.8 | 3.6 | 0.75 |
| Talc | 0.38 | 0.76 | 2.66 | 0.38 | 1.14 | 2.28 | 0.5 |
| 0.0001N HCl* | — | — | — | — | — | — | — |
| Total (mg) | 75 | 150 | 525 | 75 | 225 | 450 | 100 |

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It is further to be understood that all values are approximate, and are provided for description.

All patents, patent applications, publications, product descriptions, and protocols are cited throughout this application, the disclosures of which are incorporated herein by reference in their entireties for all purposes.

What is claimed is:

1. A method of treating chronic constipation or constipation-predominant irritable bowel syndrome in a patient in need thereof, comprising administering to the patient an oral, solid pharmaceutical dosage form comprising:
   between 100 μg and 300 μg of a peptide consisting of the amino acid sequence $Cys_1$ $Cys_2$ $Glu_3$ $Tyr_4$ $Cys_5$ $Cys_6$ $Asn_7$ $Pro_8$ $Ala_9$ $Cys_{10}$ $Thr_{11}$ $Gly_{12}$ $Cys_{13}$ $Tyr_{14}$ (SEQ ID NO:1) or a pharmaceutically acceptable salt thereof, wherein the peptide includes disulfide bonds between $Cys_1$ and $Cys_6$, $Cys_2$ and $Cys_{10}$, and $Cys_5$ and $Cys_{13}$;
   leucine in a molar ratio of leucine to the peptide between 40:1 and 20:1; and
   $Ca^{2+}$ or a salt thereof in a molar ratio of $Ca^{2+}$ the peptide between 70:1 and 50:1.

2. The method of claim 1, wherein the oral, solid pharmaceutical dosage form further comprises a polymer selected from polyvinyl pyrrolidone, polyvinyl alcohol, hydroxylpropyl methyl cellulose and mixtures thereof in an amount between 0.01 wt. % and 2 wt. % relative to the total weight of the oral dosage form.

3. A method of treating chronic constipation or constipation-predominant irritable bowel syndrome in a patient in need thereof, comprising administering to the patient an oral, solid pharmaceutical dosage form comprising a peptide consisting of the amino acid sequence $Cys_1$ $Cys_2$ $Glu_3$ $Tyr_4$ $Cys_5$ $Cys_6$ $Asn_7$ $Pro_8$ $Ala_9$ $Cys_{10}$ $Thr_{11}$ $Gly_{12}$ $Cys_{13}$ $Tyr_{14}$ (SEQ ID NO:1) or a pharmaceutically acceptable salt thereof, wherein the peptide includes disulfide bonds between $Cys_1$ and $Cys_6$, $Cys_2$ and $Cys_{10}$, and $Cys_5$ and $Cys_{13}$ in an amount between 0.2% by weight and 0.4% by weight, leucine in an amount between 0.5% by weight and 0.8% by weight, and a $Ca^{2+}$ salt in an amount between 1.4% by weight and 1.65% by weight relative to the total weight of the oral dosage form.

4. The method of claim 3, wherein the leucine is present in the oral pharmaceutical dosage form in an amount between 0.6% by weight and 0.75% by weight, and the $Ca^{2+}$ salt is present in the oral pharmaceutical dosage form in an amount between in an amount between 1.45% by weight and 1.65% by weight relative to the total weight of the oral dosage form.

5. The method of claim 3, wherein the amino acid is leucine and wherein the $Ca^{2+}$ salt is in the form of calcium chloride.

6. The method of claim 1, wherein the amino acid is leucine and wherein $Ca^{2+}$ is in the form of calcium chloride.

7. The method of claim 3, wherein the oral, solid pharmaceutical dosage form further comprises a polymer selected from polyvinyl pyrrolidone, polyvinyl alcohol, hydroxylpropyl methyl cellulose and mixtures thereof in an amount between 0.01 and 2 wt. % relative to the total weight of the oral dosage form.

8. The method of claim 1, wherein the $Ca^{2+}$ or salt thereof and leucine are present in a molar ratio of at least 1.5:1.

9. The method of claim 1, wherein the dosage form further comprises a hydrolysis product of linaclotide at a concentration between 0.1 and 4 wt. %.

10. The method of claim 3, wherein the dosage form further comprises a hydrolysis product of linaclotide at a concentration between 0.1 and 4 wt. %.

* * * * *

```
                        SEQUENCE LISTING

<160> NUMBER OF SEQ ID NOS: 5

<210> SEQ ID NO 1
<211> LENGTH: 14
<212> TYPE: PRT
<213> ORGANISM: Artificial Sequence
<220> FEATURE:
<223> OTHER INFORMATION: Synthetically generated peptide

<400> SEQUENCE: 1

Cys Cys Glu Tyr Cys Cys Asn Pro Ala Cys Thr Gly Cys Tyr
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: DISULFID
<222> LOCATION: (1)..(6)
<220> FEATURE:
<221> NAME/KEY: DISULFID
<222> LOCATION: (2)..(10)
<220> FEATURE:
<221> NAME/KEY: DISULFID
<222> LOCATION: (5)..(13)

<400> SEQUENCE: 2

Cys Cys Glu Tyr Cys Cys Asp Pro Ala Cys Thr Gly Cys Tyr
1               5                   10

<210> SEQ ID NO 3
<211> LENGTH: 14
<212> TYPE: PRT
<213> ORGANISM: Artificial Sequence
<220> FEATURE:
```

```
<223> OTHER INFORMATION: Synthetically generated peptide
<220> FEATURE:
<221> NAME/KEY: MOD_RES
<222> LOCATION: (1)..(1)
<223> OTHER INFORMATION: Formaldehyde bonded to Cys1
<220> FEATURE:
<221> NAME/KEY: DISULFID
<222> LOCATION: (1)..(6)
<220> FEATURE:
<221> NAME/KEY: DISULFID
<222> LOCATION: (2)..(10)
<220> FEATURE:
<221> NAME/KEY: DISULFID
<222> LOCATION: (5)..(13)

<400> SEQUENCE: 3

Cys Cys Glu Tyr Cys Cys Asn Pro Ala Cys Thr Gly Cys Tyr
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: DISULFID
<222> LOCATION: (1)..(6)
<223> OTHER INFORMATION: Cys1 is oxidized.
<220> FEATURE:
<221> NAME/KEY: DISULFID
<222> LOCATION: (2)..(10)
<220> FEATURE:
<221> NAME/KEY: DISULFID
<222> LOCATION: (5)..(13)

<400> SEQUENCE: 4

Cys Cys Glu Tyr Cys Cys Asn Pro Ala Cys Thr Gly Cys Tyr
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Synthetically generated peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: DISULFID
<222> LOCATION: (1)..(6)
<220> FEATURE:
<221> NAME/KEY: DISULFID
<222> LOCATION: (2)..(10)
<220> FEATURE:
<221> NAME/KEY: DISULFID
<222> LOCATION: (5)..(13)

<400> SEQUENCE: 5

Cys Cys Glu Tyr Cys Cys Asn Pro Ala Cys Thr Gly Cys Tyr
1               5                   10
```